(12) United States Patent
Lundgren-Akerlund

(10) Patent No.: US 10,081,666 B2
(45) Date of Patent: Sep. 25, 2018

(54) INTEGRIN HETERODIMER AND A SUBUNIT THEREOF

(71) Applicant: Xintela AB, Bjarred (SE)

(72) Inventor: Evy Lundgren-Akerlund, Bjarred (SE)

(73) Assignee: Xintela AB, Bjarred (SE)

( * ) Notice: Subject to any disclaimer, the term of this patent is extended or adjusted under 35 U.S.C. 154(b) by 420 days.

(21) Appl. No.: 14/552,308

(22) Filed: Nov. 24, 2014

(65) Prior Publication Data

US 2017/0121386 A1 May 4, 2017
US 2018/0079795 A9 Mar. 22, 2018

Related U.S. Application Data

(63) Continuation of application No. 13/651,602, filed on Oct. 15, 2012, now Pat. No. 8,895,253, which is a continuation of application No. 13/226,323, filed on Sep. 6, 2011, which is a continuation of application No. 11/347,179, filed on Feb. 6, 2006, now Pat. No. 8,048,991, which is a continuation of application No. 09/647,544, filed as application No. PCT/SE99/00544 on Mar. 31, 1999, now Pat. No. 7,029,858.

(30) Foreign Application Priority Data

Apr. 2, 1998 (SE) .................................... 9801164-6
Jan. 28, 1999 (SE) .................................... 9900319-6

(51) Int. Cl.
*C07K 14/705* (2006.01)

(52) U.S. Cl.
CPC .............................. *C07K 14/70546* (2013.01)

(58) Field of Classification Search
None
See application file for complete search history.

(56) References Cited

U.S. PATENT DOCUMENTS

| | | | |
|---|---|---|---|
| 5,506,126 A | 4/1996 | Seed et al. | 435/6 |
| 5,654,403 A | 8/1997 | Smith et al. | 530/387.3 |
| 5,686,059 A | 11/1997 | Goetinck et al. | 424/9.1 |
| 5,843,436 A | 12/1998 | Loike et al. | |
| 6,046,316 A | 4/2000 | Trikha et al. | 536/23.5 |
| 7,029,858 B1 | 4/2006 | Lundgren-Akerlund | 435/7.1 |
| 7,452,677 B2 | 11/2008 | Lundgren-Akerlund | 435/7.1 |
| 7,749,710 B2 | 7/2010 | Lundgren-Akerlund | |
| 8,012,696 B2 | 9/2011 | Lundgren-Akerlund | |
| 8,048,991 B2 | 11/2011 | Lundgren-Akerlund | 530/387.1 |
| 8,105,791 B2 | 1/2012 | Lundgren-Akerlund | |
| 8,895,253 B2 * | 11/2014 | Lundgren-Akerlund | C07K 14/70546 435/7.1 |
| 2006/0127398 A1 | 6/2006 | Lundgren-Akerlund | |

FOREIGN PATENT DOCUMENTS

| | | |
|---|---|---|
| JP | 2001-354699 | 12/2001 |
| WO | WO 99/51639 | 10/1999 |
| WO | WO 02/072030 | 11/2002 |
| WO | WO 03/101497 | 12/2003 |
| WO | WO 03/106492 | 12/2003 |
| WO | WO 2004089990 | 10/2004 |

OTHER PUBLICATIONS

Holmvall et al. Chondrocyte and chondrosarcoma cell integrins with affinity for collagen type II and their response to mechanical stress. Exp Cell Res. Dec. 1995;221(2):496-503.
Camper et al. Isolation, Cloning, and Sequence Analysis of the Integrin Subunit α10, a β1-associated Collagen Binding Integrin Expressed on Chondrocytes. J. Biol. Chem. 1998 273:20383-20389.
Takada et al. Molecular cloning and expression of the cDNA for alpha 3 subunit of human alpha 3 beta 1 (VLA-3), an integrin receptor for fibronectin, laminin, and collagen. J Cell Biol. Oct. 1991;115(1):257-66.
Belkin et al., "Isolation and Characteristics of Ligand Specificity of VLA-1 Integrin from Human Smooth Muscles," Biokhimila, 56(12): 2198-206 (1991) (Abstract only).
Palmer et al., "Sequence and Tissue Distribution of the Integrin α9 Subunit, a Novel Partner of β1 that is Widely Distributed in Epithelia and Muscle," The Journal of Cell Biology, 123(5): 1289-1297 (1993).
Schnapp et al., "Sequence and Tissue Distribution of the Human Integrin $α_8$ Subunit: a $β_1$-associated α Subunit Expressed in Smooth Muscle Cells," Journal of Cell Science, 108:537-544 (1995).
Smith et al., "Purification and Functional Characterization of Integrin $α_rβ_5$," The Journal of Biological Chemistry, 265(19): 11008-11013 (1990).
Song et al., "H36-α7 is a Novel Integrin Alpha Chain that is Developmentally Regulated During Skeletal Myogenesis," The Journal of Cell Biology, 117(3): 643-657 (1992).
Takada et al., "The Primary Structure of the $α^4$ Subunit of VLA-4: Homology to Other Integrins and a Possible Cell—Cell Adhesion Function," The EMBO Journal, 8(5): 1361-1368 (1989).
Takada et al., "The Primary Structure of the VLA-2/ Collegen Receptor $α^2$ Subunit (Platelet Cpla): Homology to Other Integrins and the Presence of a Possible Collagen-Binding Domain," The Journal of Cell Biology, 109: 397-407 (1989).

(Continued)

*Primary Examiner* — Nancy A Treptow
(74) *Attorney, Agent, or Firm* — McNeill Baur PLLC

(57) ABSTRACT

A recombinant or isolated integrin heterodimer comprising a novel subunit α10 in association with a subunit β is described. The α10 integrin may be purified from bovine chondrocytes on a collagen-type-II affinity column. The integrin or the subunit of α10 can be used as a marker or target of all types of cells, e.g. of chondrocytes, osteoblasts, and fibroblasts. The integrin or the subunit α10 thereof can be used as a marker or target in different physiological or therapeutic methods. They can also be used as active ingredients in pharmaceutical compositions and vaccines.

12 Claims, 22 Drawing Sheets

Specification includes a Sequence Listing.

(56) References Cited

OTHER PUBLICATIONS

Tamura et al., "Epithelial Integrin $\alpha_6\beta_4$: Complete Primary Structure of $\alpha_6$ and Variant Forms of $\beta_4$," The Journal of Cell Biology, 111: 1593-1604 (1990).
Briesewitz et al., "Expression of Native and Truncated Fortis of the Human Integrin Alpha 1 Subunit," J. Biol. Chem., vol. 268, No. 4, 1993, pp. 2989-2996.
Matsuura et al., "Subclassification, Molecular Structure, Function and Ligand in Integrin Superfamily," Nippon Rinsho, vol. 53, No. 7, 1995, pp. 1623-1630.
Weir et al., Handbook of Experimental Immunology vol. 1: Immunochemistry, 1986, pp. 8.14-8.15.
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J. Protein Chem. Oct. 1992; 11(5): 433-44.
Lederman S, et al., "A single amino acid substitution in a common african allele of the CD4 molecule ablates binding of the monoclonal antibody, OKT4," Mol. Immunol. 28(11):1171-81, 1991.
Li CH, Yamashiro D, Tseng LF, Cheng WC, Ferrara P. "Beta-Endorphin ommision analogs: dissociation of immunoreactivity from other biological activities," Proc. Natl. Acad. Sci. USA. 77(6):3211-3214, 1980.
Coleman PM. "Effects of amino acid sequence changes on antibody-antigen interactions," Res. Immunol. 145(1): 33-36, 1994.
Lenter et al., "A monoclonal antibody against an activation epitope on mouse integrin chain beta 1 blocks adhesion of lymphocytes to the endothelial integrin alpha 6 beta 1," Proc. Natl. Acad. Sci. USA. 90:9051-9055.
Kern et al., "The role of the I domain in ligand binding of the human integrin alpha 1 beta 1," J. Biol. Chem., vol. 269, Issue 36, 22811-22816, Sep. 1994.
Yednock et al., "Alpha 4 beta 1 integrin-dependent cell adhesion is regulated by a low affinity receptor pool that is confaimationally responsive to ligand," J. Biol. Chem., vol. 270, pp. 28740-28750, Dec. 1995.
International Search Report for Application No. PCT/SE2004/000580, dated Jul. 14, 2004.
Written Opinion of the International Searching Authority for Application No. PCT/SE2004/000580, dated Jul. 14, 2004.
International Preliminary Report on Patentability for Application No. PCT/SE2004/000580, dated Jul. 15, 2005.
Coller B.S., "Platelet Gpllb/11a antagonists: the first anti-integrin receptor therapeutics," J. Clin. Invest. Apr. 1997; 99(7): 1467-71.

* cited by examiner

| Peptide | Amino acid sequence |
|---------|---------------------|
| 1 | DNTAQTSAYIQYEPHHSI |
| 2 | GPGHWDR |
| 3 | AAFDGSGQR |
| 4 | FAMGALPD |
| 5 | FTASLDEWTTAAR |
| 6 | VDASFRPQGXLAP |

FIGURE 2

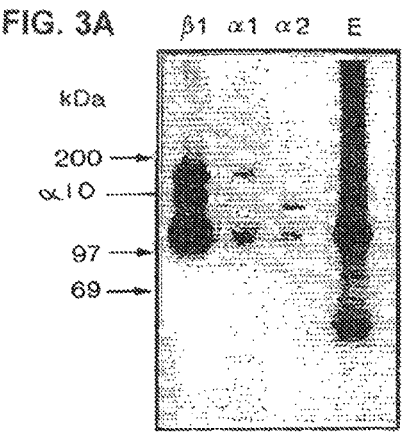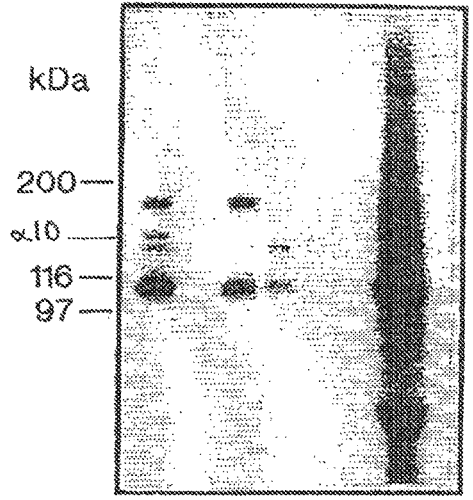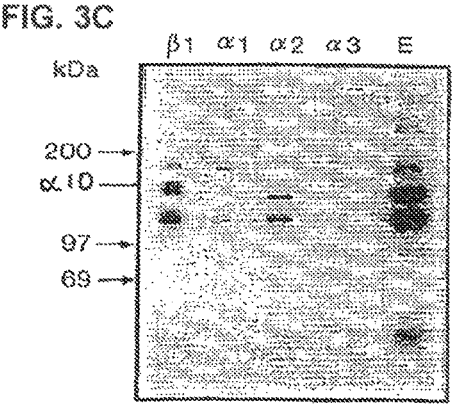

Figure 6

Human RNA Master blot

| Tissue | α10 expression | Tissue | α10 expression |
| --- | --- | --- | --- |
| Aorta | ++++ | Thyroid gland | - |
| Trachea | + | Salivary gland | - |
| Lung | ++ | Spleen | - |
| Fetal lung | ++ | Fetal spleen | - |
| Kidney | ++ | Thymus | - |
| Fetal kidney | (+) | Fetal thymus | - |
| Heart | (+) | Peripherial leucocyte | - |
| Fetal heart | ++ | Lymph node | - |
| Spinal cord | ++ | Appendix | - |
| Mammary gland | (+) | Placenta | - |
| Bone marrow | (+) | Whole brain | - |
| Small intestine | (+) | Fetal brain | - |
| Skeletal muscle | - | Amygdala | - |
| Liver | - | Caudate nucleus | - |
| Fetal liver | - | Cerebellum | - |
| Colon | - | Cerebral cortex | - |
| Bladder | - | Frontal lobe | - |
| Uterus | - | Hippocampus | - |
| Prostate | - | Medulla oblongata | - |
| Stomach | - | Occipitial lobe | - |
| Testis | - | Putamen | - |
| Ovary | - | Substantia nigra | - |
| Pancreas | - | Temporal lobe | - |
| Piutiatary gland | - | Thalamus | - |
| Adrenal gland | - | Subthalamic nucleus | - |

```
TGNTMMMKCMCACGAKMGWSAKGNCCGAKGGTKGKGVAAVGTGACARAGCTNGMNAAAARANGAAGTATGACCWGTGGGC  80
  ?  ?  ?  ?  R  ?  ?  ?  ?  P  ?  V  ?  ?  ?  D  ?  A  ?  ?  K  ?  K  Y  D  ?  W  A
   ?  ?  ?  H  ?  ?  ?  ?  R  ?  ?  ?  ?  V  T  ?  L  ?  K  ?  ?  S  M  T  ?  G
 V  ?  ?  ?  ?  T  ?  ?  ?  ?  ?  G  ?  ?  ?  .  Q  S  ?  ?  K  ?  E  V  .  P  V  G

CRAGATAGMKAMDAAGCNGMSAGKTRAMGGACGATGGNCCMGCCAAVCGABWGGNAAHTBCGGCNWDCARNGTCCAAATK  160
  ?  I  ?  ?  ?  K  ?  ?  ?  ?  G  R  W  ?  ?  Q  ?  ?  G  ?  ?  G  ?  Q  ?  P  N
 P  R  .  ?  ?  ?  S  ?  ?  ?  ?  D  D  G  P  A  ?  R  ?  ?  ?  ?  A  ?  ?  V  Q  ?
  ?  D  ?  ?  ?  ?  A  ?  ?  .  R  T  M  ?  ?  P  ?  ?  ?  ?  ?  R  ?  ?  ?  S  K  ?

SANKTCSCAGGAACCMACGGAMTGGCTCGCARCCCDTAGGGATCAGGKACGATGRCTCSCCGRNSKACTCSGNKTGATWA  240
  ?  ?  ?  R  N  ?  R  ?  G  S  Q  P  ?  G  I  R  ?  D  ?  S  P  ?  ?  S  ?  .  ?
    ?  ?  ?  G  T  ?  G  ?  ?  A  R  ?  P  .  G  S  G  T  M  ?  ?  R  ?  ?  T  ?  ?  D  ?
    ?  S  Q  E  P  T  ?  W  L  A  ?  ?  R  D  Q  ?  R  ?  L  ?  ?  ?  L  ?  ?  I

ATCGMNWGTMGGMAGGCGGMGGAATTRWAAAGTANTGGTMGAMAKATGWGVMGGAWATGATRRGTMGACTVTMVMGGVAK  320
  I  ?  ?  R  ?  A  ?  E  L  ?  S  ?  G  R  ?  M  ?  R  ?  .  ?  V  D  ?  ?  G  ?
   S  ?  V  G  R  R  R  N  ?  K  V  ?  V  ?  ?  ?  ?  G  ?  D  ?  ?  T  ?  ?  ?
 N  R  ?  ?  ?  ?  G  G  G  I  ?  K  ?  W  ?  ?  ?  ?  ?  M  ?  ?  R  L  ?  R  ?

VTAKSGGTACAGGCGAAKACARGRAKGTGTCTGAGGAADTCAGNAGGACAAMMTTGCCGAAGTCMGGACTTAGKATRGAT  400
  ?  ?  Y  R  R  ?  Q  ?  ?  V  .  G  ?  Q  ?  D  ?  ?  A  E  V  R  T  .  ?  ?
 ?  ?  G  T  G  E  ?  ?  ?  ?  V  S  E  E  ?  ?  R  T  ?  L  P  K  S  G  L  ?  ?  D
  ?  ?  V  Q  A  ?  T  ?  ?  C  L  R  ?  S  ?  G  Q  ?  C  R  S  ?  D  L  ?  ?  I

ACGAANCKTRGATCTTAMADGGGGGNKAGCGAGTGCSTAAACGVARATRGGNSWGTCTACTTMAACNCCAAGNGDGGACA  480
 Y  E  ?  ?  I  L  ?  G  G  ?  R  V  ?  K  R  ?  ?  ?  ?  L  L  ?  ?  Q  ?  ?  T
  T  ?  ?  ?  S  ?  ?  G  ?  S  E  C  ?  N  ?  ?  ?  ?  V  Y  ?  N  ?  K  ?  G  H
   R  ?  ?  D  L  ?  ?  G  ?  A  S  A  .  T  ?  ?  G  ?  S  T  ?  T  P  ?  ?  D

TTTACTAGASGAGGAGAGTAGCCAGATCACDTGAGATGATCTAAKGTGGGGTCCCGTTGCCAGTATATGAGAGGACTGGT  560
   F  T  R  ?  G  E  .  P  D  H  ?  R  .  S  ?  V  G  S  R  C  Q  Y  M  R  G  L  V
  L  L  ?  E  E  S  S  Q  I  T  .  D  D  L  ?  W  G  P  V  A  S  I  .  E  D  W
 I  Y  .  ?  R  R  V  A  R  S  ?  E  M  I  .  ?  G  V  P  L  P  V  Y  E  R  T  G

TCGGCAGACATWGATGCTCTTTGCTGACTCACATATTGTTGCCVTGAGKATGATCAGATACGATCTGWTGTCCCTCATCA  640
    R  Q  T  ?  M  L  F  A  D  S  H  I  V  A  ?  ?  M  I  R  Y  D  L  ?  S  L  I
 F  G  R  H  ?  C  S  L  L  T  H  I  L  L  P  .  ?  .  S  D  T  I  ?  C  P  S  S
  S  A  D  I  D  A  L  C  .  L  T  Y  C  C  ?  E  ?  D  Q  I  R  S  ?  V  P  H  H

TGAATSTGRGCCGTGATGCTAATGAGATTCGCCTATGATGGAACAAGAGACTTMTGCTACAGCAGGCGAATGAAGGTTTC  720
 M  N  ?  ?  R  D  A  N  E  I  R  L  .  W  N  K  R  L  ?  L  Q  Q  A  N  E  G  F
  .  ?  ?  ?  A  V  M  L  M  R  F  A  Y  D  G  T  R  D  ?  C  Y  S  R  R  M  K  V  S
   E  ?  ?  ?  P  .  C  .  .  D  S  P  M  M  E  Q  E  T  ?  A  T  A  G  E  .  R  F

TAGAGTAGGAGTCTCAGGAGGAGAGAAACTGTGGACCTGGAGGACCAGGGACTCCAGGAGGAAGTWGCCACAACTGGCTT  800
    .  S  R  S  L  R  R  R  E  T  V  D  L  E  D  Q  G  L  Q  E  E  V  A  T  T  G  L
   R  V  G  V  S  G  G  E  K  L  W  T  W  R  T  R  D  S  R  R  K  ?  P  Q  L  A
 L  E  .  E  S  Q  E  E  R  N  C  G  P  G  G  P  G  T  P  G  G  S  ?  H  N  W  L

GMAGTTTCGGCTCCGATCCTGATACWGGCTCGTCCTTVGAGTTATCCCCCTCTCTTGCTGGATGGCTCAGAAATGCCTGG  880
  ?  F  R  L  R  S  .  Y  ?  L  V  L  ?  V  I  P  L  S  C  W  M  A  Q  K  C  L
 ?  S  F  G  S  D  P  D  T  G  S  S  ?  E  L  S  ?  S  L  A  G  W  L  R  N  A  W
  ?  V  S  A  F  I  L  I  ?  A  R  P  ?  S  Y  P  P  L  L  D  G  S  E  M  P  G

ACCTTTTCATCCCCACTGGACAAACTAGGCGTCTGGCGTTGTGGCCCTGGGATTGTGGGGCTGTGTGGCCTCATATCCTC  960
 D  L  F  I  P  T  G  Q  T  R  R  L  A  L  W  P  W  D  C  G  A  V  W  P  H  I  L
  T  F  S  S  P  L  D  K  L  G  V  W  R  C  G  P  G  I  V  G  L  C  G  L  I  S  S
   P  F  H  P  H  W  T  N  .  A  S  G  V  V  A  L  G  L  W  G  C  V  A  S  Y  P

CATTCTGTCTATTCTCACCCTAATCTGTCCCTGGNTACGACTCAAGCCCYGACTGACAMTGTGGTACAAGATAAGGAGGG  1040
 H  S  V  Y  S  H  P  N  L  S  L  ?  T  T  Q  A  ?  T  D  ?  V  V  Q  D  K  E  G
   I  L  S  I  L  T  L  I  C  P  W  ?  R  L  K  P  ?  L  T  ?  ?  W  Y  K  I  R  R
 P  F  C  L  F  S  P  .  S  V  P  G  Y  D  S  S  P  D  .  ?  C  G  T  R  .  G  G

AGCCCAGGTGGGTGAGATGGAAGCTGAGATGGTNCACTGTGTGCCMACCTCATTGTAATTCAACTNCCTTGACTGAAGTT  1120
   A  Q  V  G  E  M  E  A  E  M  V  H  C  V  P  T  S  L  .  F  N  ?  L  D  .  S
 E  P  R  W  V  R  W  K  L  R  W  ?  T  V  C  ?  P  H  C  N  S  T  ?  L  T  E  V
  S  P  G  G  .  D  G  S  .  D  G  ?  L  C  A  ?  L  I  V  I  Q  L  P  .  L  K  L

AAAATCCAGATCCYTAGGGATGAGGGGAAGAACCTGCCAAAGACGGGTCAGGAAGGCAGTGCTAAGGGAAGGCTCCTGCA  1200
  .  N  P  D  P  .  G  .  G  E  E  P  A  K  D  G  S  G  R  Q  C  .  G  K  A  P  A
   K  I  Q  I  ?  R  D  E  G  K  N  L  P  K  T  G  E  G  S  A  K  G  R  L  L  Q
    K  S  R  S  L  G  M  R  G  R  T  C  Q  R  R  V  R  K  A  V  L  R  E  G  S  C

GGCCTCTGCAGTTGGACTTCATTCAGTCCCATTGCCAGAATCTCATAGCTCTTCCCYYTATCTCTCTGTCTTGAGTCTAG  1280
   G  L  C  S  W  T  S  F  S  P  I  A  R  I  S  .  L  F  P  L  S  L  C  L  E  S  S
    A  S  A  V  G  L  H  S  V  P  L  P  E  S  H  S  S  S  ?  Y  L  S  V  L  S  L
 R  P  L  Q  L  D  F  I  Q  S  H  C  Q  N  L  I  A  L  P  ?  I  S  L  S  .  V  .

TTAAGAATTTGTTACCGGAGACAGAATTCTCTTTCTTAGCCTCCTGGCCAGATATTTAAAAGGAGGGGGGTGGGTTACTT  1360
   .  E  F  V  T  G  D  R  I  L  F  L  S  L  L  A  R  Y  L  K  G  G  G  W  V  T
  V  K  N  L  L  P  E  T  E  F  S  F  L  A  S  W  P  D  I  .  K  E  G  G  G  L  L
   L  R  I  C  Y  R  R  Q  N  S  L  S  .  P  P  G  Q  I  F  K  R  R  G  V  G  Y  F
```

```
CAGGTGAGGGAAGCAAACTTGGTTTCTGCTGGGAATGGAAGTTATGTGGATTGTTTATAATTGGGACCATTATGGCTAAA 2800
   R . G K Q T W F L L G M E V M W I V Y N W D H Y G .
  T G E G S K L G F C W E W K L C G L F I I G T I M A K
   Q V R E A N L V S A G N G S Y V D C L . L G P L W L K

ATCTTGCGGGCGCTCAGGTCGGAGGTTAATACCGATGCTATATTTCCTGTGTGCACTCATGTTCTTAGACACCCAAATGG 2880
 N L A G A Q V G G . Y R C Y I S C V H S C S . T P K W
  I ? R A L R S E V N T D A I F P V C T H V L R H P N G
   S ? G R S G R R L I P M L Y F L C A L M F L D T Q M

CAGTGGCCAAAACTTCCTCTGGCTTGTACCTCATTATCTAAACCTTTGTACCTAATTATCTAAAACCTTGGTCCTAAACT 2960
 Q W P K L P L A C T S L S K P L Y L I I . N L G P K L
  S G Q N F L W L V P H Y L N L C T . L S K T L V L N
   A V A K T S S G L Y L I I . T F V P N Y L K P W S . T

CCACAGACATGAGGGCACAGAAAAGAGACGTGTCTCTCATCTTCCATTCGGTTACACTGATTCCTACCTTCCCTGCTTCT 3040
  H R H E G T E K R R V S H L P F G Y T D S Y L P C F
  S T D M R A Q K R D V S L I F H S V T L I P T F P A S
   P Q T . G H R K E T C L S S I R L H . F L P S L L L

CCCTGCCATTGGTGCTCCTTGGTGCCTGAGGCATAATTGCCTTACTATGTGGTCAGAACTCTGGGTTCGCCTAACGACCG 3120
 S L P L V L L G A . G I I A L L C G Q N S G F A . R P
  P C H W C S L V P E A . L P Y Y V V R T L G S P N D R
   P A I G A P W C L R H N C L T M W S E L W V R L T T

AGCTACAGTTTCTGGTCTCATAGCCCTGCCAATTTCCTGGATTAAAAAAAAAAAGGCTCACATATAAAATACCTTTTCTGA 3200
 S Y S F W S H S P A N F L D . K K K A H I . N T F S E
  A T V S G L I A L P I S W I K K K R L T Y K I P F L
   E L Q F L V S . P C Q F P G L K K K G S H I K Y L F -

AAATGAGCACAGTGTGAGTTGAAGTTAGATTTTGGGGGATGGAGGGTTGCTTGGATGCAAAGAGCAAGACAGTAGAGAAG 3280
 N E H S V S . S . I L G D G G L L G C K E Q D S R E
  K M S T V . V E V R F W G M E G C L D A K S K T V E K
   K . A Q C E L K L D F G G W R V A W M Q R A R Q . R R

AGAATCATGGGAGGGATAAGAGGCTGGAATTTTTCCCTGCTAGTGCCCTATAATCTTTGTTTCCTAAAATAACAGCTCTG 3360
 E N H G R D K R L E F F P A S A L . S L F P K I T A L
  R I M G G I R G W N F S L L V P Y N L C F L K . Q L .
   E S W E G . E A G I F P C . C P I I F V S . N N S S

ATTTTATGGGAATTGGGGTCAGGAGAAAGGAATCAGTAGGCACAGATGGGACCCCAAGCGTGGACTAAAGTTTGAGGAAA 3440
 I L W E L G S G E R N Q . A Q M G P P Q A W T K V . G N
  F Y G N W G Q E K G I S R H R W D P K R G L K F E E
   D F M G I G V R R K E S V G T D G T P S V D . S L R K

CTATGGGAGTAGGCAAGGGGTGTTTGTAAGGTGGATGAGATGAGGAGATTGTGGTGGGGGGAGTCTTGGGGGTGATAGG 3520
 Y G S R Q G V F V R W M R . G D C G G G E S W G . .
  T M G V V G K G C L . G G . D E E I V V G G S L G G D R
   L W E . A R G V C K V D E M R R L W W G G V L G V I G

ACCCTTAACAGGGATAGATGGCAAACTGTGTGTGGGCAGGCCGGTGGTTCCACCCACTTAATTAGCGTTGAGGTTGGCAG 3600
 D P . Q G . M A N C V W A G R W F H P L N . R . G W Q
  T L N R D K Q T V C G Q A G G S T H L I S V R V G R
   P L T G I D G K L C V G R P V V P P T . L A L R L A

GGCTGGAAGGAGCCAGCACTCTCAACCTTGGAGAAAGTGCAAGTGTGACAAGAAGAAACAGAAAGAGGAGACACCCGGGC 3680
 G W K E P A L S T L E K V Q V . Q E E T E R G D T R A
  A G R S Q H S Q P W R K C K C D K K K Q K E E T P G
   G L E G A S T L N L G E S A S V T R R N R K R R H P G

AGGGAGCTCCTTGCCATCGTTTCTTCCCATGGCCCTGGCTTTGGGAAGAATTAGGAAAGGGTGGTGACTCTGCATCCTCA 3760
   G S S L P S F L P M A L A L G R I R K G W . L C I L
  Q G A P C H R F F P W P W L W E E L G K G G D S A S S
   R E L L A I V S S H G P G F G K N . E R V V T L H P Q

GAAAAGCCCTCTCTCCCTCTTTGGACTCTCGAGGCTTAGAGAGGAGAATGTGTAGGAGGAATGATGTGGAAAGAGTAACT 3840
 R K A L S P S L D S R G L E R R M C R R N D V E R V T
  E K P S L P L W T L E A . R G E C V G G M M W K E . L
   K S P L S L F G L S R L R E E N V . E E . C G K S N

TGACCTATCCAGATGTGTCTGTGAATGAGATTTCAGGAATGAGAATGGAAATACAGCTGTGCTTCAGCATGGCCGAGGGC 3920
 . P I Q M C L . M R F Q E . E W K Y S C A S A W P R A
  D L S R C V C E . D F R N E N G N T A V L Q H G R G
   L T Y P D V S V N E I S G M R M E I Q L C F S M A E G

CTTAGGATCCCTCACCCCCACCCCACAGGAAGAGAATCATCCAATCATCCCACCTGGGGTTCTGAGGACATGACATTGAC 4000
 L G S L T P T P Q E E N H P I I P F G V L R T . H .
  P . D P S P P H R K R R I I Q S S H L G F . G H D I D
   L R I P H P H P T G R E S S N H P T W G S E D M T L T

ACAGAGCAGGAGAGCTGAGATAGAAACACTCCCTCCTGTCTTGTCTCCCACTAAGCCTCACCAGTCCTTCATTAACTGAT 4080
 H R A G E L R . K H S L L S C L P L S L T S P S L T D
  T E Q E S . D R N T P S C L V S H . A S P V L H . L I
   Q S R R A E I E T L P P V L S P T K P H Q S F I N -
```

```
CTGGTTTTACCAACTTAAAAACAAAACAAAACAGCATATCCTGTGCACAGCCTATCCCTCATCCATCACGTGTCCTCCAT 5520
  S  G  F  T  N  L  K  T  K  Q  N  S  I  S  C  A  Q  P  I  P  H  P  S  R  V  L  H
   L  V  L  P  T  .  K  Q  N  K  T  A  Y  P  V  H  S  L  S  L  I  H  H  V  S  S  I
    W  F  Y  Q  L  K  N  K  T  K  Q  H  I  L  C  T  A  Y  P  S  S  I  T  C  P  P

ATCTTATTTTTGTGGGTCTTATAGATGCCAAGTCAGCACTCAGTTATTGGGTTCTCCCCTCATGCCTTTCATATACTTTC 5600
  I  L  F  L  W  V  L  .  M  P  S  Q  H  S  V  I  G  F  S  P  H  A  F  H  I  L  S
   S  Y  F  C  G  S  Y  R  C  Q  V  S  T  Q  L  L  G  S  P  L  M  P  F  I  Y  F
    Y  L  I  F  V  G  L  I  D  A  K  S  A  L  S  Y  W  V  L  P  S  C  L  S  Y  T  F

TTATCTACTGCCTTTTGGGAGATAGTCTTATGTAGCCCAGGCTGTCCTTGATCTTGGAATTTGCTTGCCTCAGCTTCTCA 5680
  Y  L  L  P  F  G  R  .  S  Y  V  A  Q  A  V  L  D  L  G  I  C  L  P  Q  L  L
   L  I  Y  C  L  L  G  D  S  L  M  .  P  R  L  S  L  I  L  E  F  A  C  L  S  F  S
    L  S  T  A  F  W  E  I  V  L  C  S  P  G  C  P  .  S  W  N  L  L  A  S  A  S  Q

GTCTCAAGTACTGGGATAATAGGCATGCATTGTCTGCCTGGCCTTTGCTGAACATGCCCTCTGTGGCCATTGGTAGGGCA 5760
  S  L  K  Y  W  D  N  R  H  A  L  S  A  W  P  L  L  N  M  P  S  V  A  I  G  R  A
   V  S  S  T  G  I  I  G  M  H  C  L  P  G  L  C  .  T  C  P  L  W  P  L  V  G  H
    S  Q  V  L  G  .  .  A  C  I  V  C  L  A  F  A  E  H  A  L  C  G  H  W  .  G

TGAGTCAAATACTGCCCTCCCCCACAACACACACACAAACGAAAGTGAGGCTCTCTAAGTGTTCCATAGCACAGGGTAGT 5840
  .  V  K  Y  C  P  P  P  Q  H  T  H  K  R  K  .  G  S  L  S  V  P  .  H  R  V  V
   E  S  N  T  A  L  P  H  N  T  H  T  N  E  S  E  A  L  .  V  F  H  S  T  G  .
    M  S  Q  I  L  P  S  P  T  T  H  T  Q  T  K  V  R  L  S  K  C  S  I  A  Q  G  S

GGTAGGCCTCTCGCTAGTGCATATTTCATTCTTTTACTCTGCCCATCTCTTCTTTCTTTGATTTCCACACTGGGGACCTG 5920
  V  G  L  S  L  V  H  I  S  F  F  Y  S  A  H  L  F  F  L  .  F  P  H  W  G  F
   W  .  A  S  R  .  C  I  F  H  S  F  T  L  P  I  S  S  F  F  D  F  H  T  G  D  L
    G  R  P  L  A  S  A  Y  F  I  L  L  L  C  P  S  L  L  S  L  I  S  T  L  G  T  W

GCATAGTACTTTCCTGGTAATTAAGAGAGAATTCCCTTTTAAGTGCCTGCATTGCAGCGTCCTCCTGGGACATTCTCCCT 6000
  G  I  V  L  S  W  .  L  R  E  N  S  L  L  S  A  C  I  A  A  S  S  W  D  I  L  P
   A  .  Y  F  P  G  N  .  E  R  I  P  F  .  V  P  A  L  Q  R  P  P  G  T  F  S  L
    H  S  T  F  L  V  I  K  R  E  F  P  F  K  C  L  H  C  S  V  L  L  G  H  S  P

TGCTGACTACACCCCACATCCTTCCATGTTTTTGTTTCCCATCACTATGCCCCCCTTCTAGGCTGTCCCACATACATGG 6080
  G  .  L  H  F  T  S  F  H  V  F  C  F  P  S  L  C  P  P  S  R  L  S  H  I  K  G
   A  D  Y  T  P  H  P  S  M  F  F  V  S  H  H  Y  A  P  L  L  G  C  P  T  Y  M
    L  L  T  T  P  H  I  L  P  C  F  L  P  I  T  M  P  P  F  .  A  V  P  H  T  W

ATGTCGTCATTGTTTTGGATGGCTCCAACAGTATCTATCCCTGGTCAGAAGTTCAGACTTTCCTTCGGAGGCTGGTAGGA 6160
  C  R  H  C  F  G  W  L  Q  Q  Y  L  S  L  V  R  S  S  D  F  P  S  E  A  G  R
   D  V  V  I  V  L  D  G  S  N  S  I  Y  P  W  S  E  V  Q  T  F  L  R  R  L  V  G
    M  S  S  L  F  W  M  A  P  T  V  S  I  P  G  Q  K  F  R  L  S  F  G  G  W  .  E

AGACTGTTCATCGATCCGGAGCAGATACAGGTAAGAGAAAGATATGTGGATAGGATTGGAGGGAAAGAAGTAAACACTCC 6240
  K  T  V  H  R  S  G  A  D  T  G  K  R  K  I  C  G  .  D  W  R  E  R  S  K  H  S
   R  L  F  I  D  P  E  Q  I  Q  V  R  E  R  Y  V  D  R  I  G  G  K  E  V  N  T  P
    D  C  S  S  I  R  S  R  Y  R  .  E  K  D  M  W  I  G  L  E  G  K  K  .  T  L

TGGACCCTTGGATGTAAGCAGCCATGTCCAGCCTCTTGATGACACCCTGGGACATTGTCTTCTACAGAACTCATGCTCAA 6320
  W  T  L  G  C  K  Q  P  C  P  A  S  .  .  H  P  G  T  L  S  S  T  E  L  M  L  K
   G  P  L  D  V  S  S  H  V  Q  P  L  D  D  T  L  G  H  C  L  L  Q  N  S  C  S
    L  D  P  W  M  .  A  A  M  S  S  L  L  M  T  P  W  D  I  V  F  Y  R  T  H  A  Q

GAACTGTGCAATTAACTTACCAAAAAGTCACAAAAATTTCATAATGTTTGAAGTAAGTTTATGATTGTGTGGGGGGCCAC 6400
  N  C  A  I  N  L  P  K  S  H  K  N  F  I  M  F  E  V  S  L  .  L  C  G  G  P
   R  T  V  Q  L  T  Y  Q  K  V  T  K  I  S  .  C  L  K  .  V  Y  D  C  V  G  G  H
    E  L  C  N  .  L  T  K  K  S  Q  K  F  H  N  V  .  S  K  F  M  I  V  W  G  A  T

ACTCAGAGCTTCCCTTTGCTGCTTGTAGTTGCTTGGGCAATGCATGCCATGAGCTGCAAGTTAGACACACCTGTTCACTT 6480
  H  S  E  L  P  F  A  A  C  S  C  L  G  N  A  C  H  E  L  Q  V  R  H  T  C  S  L
   T  Q  S  F  P  L  L  L  V  V  A  W  A  M  H  A  M  S  C  K  L  D  T  P  V  H  F
    L  R  A  S  L  C  C  L  .  L  L  G  Q  C  M  P  .  A  A  S  .  T  H  L  F  T

CCCCTTCATCGTGCTGCAGGTTGGACACACCTGTTAGGGGTTCACTTCCCCTTCATCCTTTGTGCTCCATCTTCTCTACG 6560
  P  L  H  R  A  A  G  W  T  H  L  L  G  V  H  F  P  F  I  L  C  A  P  S  S  L  R
   P  F  I  V  L  Q  V  G  H  T  C  .  G  F  T  S  P  S  S  F  V  L  H  L  L  Y
    S  P  S  S  C  C  R  L  D  T  P  V  R  G  S  L  P  L  H  F  L  C  S  I  F  S  T

CTCTTCATACATCCCATGTGGGCACATGGTCTATTGTTCTCAGGTAGGACTGGTACAGTACGGGGAGAACCCTGTGCATG 6640
  S  S  Y  I  P  C  G  H  M  V  Y  C  S  Q  V  G  L  V  Q  Y  G  E  N  P  V  H
   A  L  H  T  S  H  V  G  T  W  S  I  V  L  R  .  D  W  Y  S  T  G  R  T  L  C  M
    L  F  I  H  P  M  W  A  H  G  L  L  F  S  G  R  T  G  T  V  R  G  E  P  C  A  .

AGTGGTCCCTGGGAGACTTCCGAACAAAGGAAGAAGTTGTGAGAGCAGCAAGGAACCTAAGTCGGAGGGAAGGGCGAGAA 6720
  E  W  S  L  G  D  F  R  T  K  E  E  V  V  R  A  A  R  N  L  S  R  R  E  G  R  E
   S  G  P  W  E  T  S  E  Q  R  K  K  L  .  E  Q  Q  G  T  .  V  G  G  K  G  E  K
    V  V  P  G  R  L  P  N  K  G  R  S  C  E  S  S  K  E  P  K  S  E  G  R  A  R

ACGAGAACCGCCCAAGCGATCATGGTGGCATGGTGAGACATTGTAAAGGGGTCGTGTGAGGGAGGAGGAAGGATCAGCAG 6800
  T  R  T  A  Q  A  I  M  V  A  W  .  D  I  V  K  G  S  C  E  G  G  G  R  I  S  R
   R  E  P  P  K  R  S  W  W  H  G  E  T  L  .  R  G  R  V  R  E  E  E  G  S  A
    N  E  N  R  P  S  D  H  G  G  M  V  R  H  C  K  G  V  V  .  G  R  R  K  D  Q  Q
```

Figure 15F

```
GGAGAGGGAGAGGGTCTGGAGTGTAGTGTATACATCACAAGATGCTCTGGGCGCTTATCTTTATCTGCATGCCAGAAGTT 6880
    E  R  E  R  V  W  S  V  V  Y  T  S  Q  D  A  L  G  A  Y  L  Y  L  H  A  R  S
 G  R  G  R  G  S  G  V  .  C  I  H  H  K  M  L  W  A  L  I  F  I  C  M  P  E  V
  G  E  G  E  G  L  E  C  S  V  V  Y  I  T  R  C  S  G  R  L  S  L  S  A  C  Q  K  F

CGTGGAGGAAGGCTAGGTTGCTGTCACCATACTCTCTCTTACTGTATTTGCATTTTATGGTGTCTGTGGGTGTATCTCTC 6960
    S  W  R  K  A  R  L  L  S  P  Y  S  L  L  L  Y  L  H  F  M  V  S  V  G  V  S  L
 R  G  G  R  L  G  C  C  H  H  T  L  S  Y  C  I  C  I  L  W  C  L  W  V  Y  L  S
  V  E  E  G  .  V  A  V  T  I  L  S  L  T  V  F  A  F  Y  G  V  C  G  C  I  S

CTTGTCTGTTCTGTTTCTGCACACAGAACTCCATCTTTCCTCTTCTACTCCTGCGTCAATTCTGATACCTAGCTTCTCAA 7040
    L  V  C  S  V  S  A  H  R  T  P  S  F  L  F  Y  S  C  V  N  S  D  T  .  L  L  N
 L  S  V  L  F  L  H  T  E  L  H  L  S  S  S  T  P  A  S  I  L  I  P  S  F  S
  P  C  L  F  C  F  C  T  Q  N  S  I  F  P  L  L  L  R  Q  F  .  Y  L  A  S  Q

CCACTCACGCCCTAGTATTCTTTTCAAACATGACTCTAAACCTCTGGGGAGGCTACATGACCTGACTGTCTTTATTCTCC 7120
    H  S  R  P  S  I  L  F  K  H  D  S  K  P  L  G  R  L  H  D  L  T  V  F  I  L
 T  T  H  A  L  V  F  F  S  N  M  T  L  N  L  W  G  G  Y  M  T  .  L  S  L  F  S
  P  L  T  P  .  Y  S  F  Q  T  .  L  .  T  S  G  E  A  T  .  P  D  C  L  Y  S  P

AGTTCCTTGATCTTGTCAACCCAAGTGTTTGCTGAATGAATCTATAAATAAATAATGCTTGTACATATTTACACTGATGA 7200
    Q  F  L  D  L  V  N  P  S  V  C  .  M  N  L  .  I  N  N  A  C  T  Y  L  H  .  .
 S  S  L  I  L  S  T  Q  V  F  A  E  .  I  Y  K  .  I  M  L  V  H  I  Y  T  D  D
  V  P  .  S  C  Q  P  K  C  L  L  N  E  S  I  N  K  .  C  L  Y  I  F  T  L  M

CAGATTATTTTATATGTTCCGTGCCATCTAAACAGTCAAGTTGTGACTCTGTGCCAGTTTGCATGCTAGATACTGTTGGG 7280
    Q  I  I  L  Y  V  P  C  H  L  N  S  Q  V  V  T  L  C  Q  F  A  C  .  I  L  L  G
 R  L  F  Y  M  F  R  A  I  .  T  V  K  L  .  L  C  A  S  L  H  A  R  Y  C  W
  T  D  Y  F  I  C  S  V  F  S  K  Q  S  S  C  D  S  V  P  V  C  M  L  D  T  V  G

GAATGGTGTAGAAGACATCTGACCTCAGTGAACTGCTGACAGTGTTAATACACTATACGGGCATGCCTGCATGCAAGCCT 7360
    N  G  V  E  D  I  .  P  Q  .  T  A  D  S  V  N  T  L  Y  G  H  A  C  M  Q  A
 G  M  V  .  K  T  S  D  L  S  E  L  L  T  V  L  I  H  Y  T  G  M  P  A  C  K  P
  E  W  C  R  R  H  L  T  S  V  N  C  .  Q  C  .  Y  T  I  R  A  C  L  H  A  S  L

GTGTGTATGTGCATGCATATGCACACACATACATATGACCATATAGCATTCTTTTATCTCTCTTCTTAGCACAGAAGGGT 7440
    C  V  Y  V  H  A  Y  A  H  T  Y  I  .  P  Y  S  I  L  L  S  L  F  L  A  Q  K  G
 V  C  M  C  M  H  M  M  H  T  H  T  Y  D  H  I  A  F  F  Y  L  S  S  .  H  R  R  V
  C  V  C  A  C  I  C  T  H  I  H  M  T  I  .  H  S  F  I  S  L  L  S  T  E  G

TCAGTCAGTCCCGGGGGGACGACCAGAGGCCGCTAGGCTGCTGGTAGTTGTCACTGATGGAGAGTCCCATGATGGAGAG 7520
    S  V  S  P  G  G  D  D  Q  R  P  L  G  C  W  .  L  S  L  M  E  S  P  M  M  E  R
 Q  S  V  P  G  G  T  T  R  G  R  .  A  A  G  S  C  H  .  W  R  V  P  .  W  R
  F  S  Q  S  R  G  G  R  P  E  A  A  R  L  L  V  V  V  T  D  G  E  S  H  D  G  E

GAACTTCCAGCAGCGCTAAAGGCCTGTGAGGCTGGCAGAGTGACACGTTATGGGATTGCGGTGAGACTTGATCAAGTCCA 7600
    N  F  Q  Q  R  .  R  P  V  R  L  A  E  .  H  V  M  G  L  R  .  D  L  I  K  S
 G  T  S  S  S  A  K  G  L  .  G  W  Q  S  D  T  L  W  D  C  G  E  T  .  S  S  P
  E  L  P  A  A  L  K  A  C  E  A  G  R  V  T  R  Y  G  I  A  V  R  L  D  Q  V  Q

GTTGTTTTGTTTTGTGTTGTATCGTGTGTGTGTGTGTGTGTGTGTGTGTGTGTGTGTGTATGTGATAT 7680
    S  C  F  V  L  C  C  I  V  C  V  C  V  C  V  C  V  C  V  Y  V  .  Y
 V  V  L  F  C  V  V  S  C  V  C  V  C  V  C  V  C  V  C  V  C  V  C  M  C  D  M
  L  F  C  F  V  L  Y  R  V  C  V  C  V  C  V  C  V  C  V  C  V  C  V  I

GTGTGCATGCATCAGTGCACATACCATAGTGTGTATATGCGGGTCAGAGAACAACCTCAGATGTTGGTCCTCACCTTCCA 7760
    V  C  M  H  Q  C  T  Y  H  S  V  Y  M  R  V  R  E  Q  P  Q  M  L  V  L  T  F  H
  C  A  C  I  S  A  H  T  I  V  C  I  C  G  S  E  N  N  L  R  C  W  S  S  P  S
 C  V  H  A  S  V  H  I  P  .  C  V  Y  A  G  Q  R  T  T  S  D  V  G  P  H  L  P

TCTTGTTCCAAACTGGATATCTTGTTCACTTCGGCATACAATAAGCCAGATTAGCTGACCCACAAGTCTTGGGCAGGTCT 7840
    L  V  P  N  W  I  S  C  S  L  R  H  T  I  S  Q  I  S  .  P  T  S  L  G  Q  V
 I  L  F  Q  T  G  Y  L  V  H  F  G  I  Q  .  A  R  L  A  D  P  Q  V  L  G  R  S
  S  C  S  K  L  D  I  L  F  T  S  A  Y  N  K  P  D  .  L  T  H  K  S  W  A  G  L

TCTGTCTCAGCCTCCTGTCTCTTGGTTTGAGGCATTCTGGAATTTACAGATAAGCTTGATATCGAATTCCTGCAGCCCGG 7920
    F  C  L  S  L  L  S  L  G  L  R  H  S  G  I  Y  R  .  A  .  Y  R  I  P  A  A  R
  S  V  S  A  S  C  L  L  V  .  G  I  L  E  F  T  D  K  L  D  I  E  F  L  Q  P  G
   L  S  Q  P  P  V  S  W  F  E  A  F  W  N  L  Q  I  S  L  I  S  N  S  C  S  P

GGGATCCACTAGTTCTAGAGCGGCCGCCACCAAGGGAG 7958
    G  I  H  .  F  .  S  G  R  H  Q  G  S
     G  S  T  S  S  R  A  A  A  T  K  G
  G  D  P  L  V  L  E  R  P  P  P  R  E
```

INTEGRIN HETERODIMER AND A SUBUNIT THEREOF

CROSS REFERENCE TO RELATED APPLICATIONS

This application is a continuation of U.S. application Ser. No. 13/651,602, filed 15 Oct. 2012, now U.S. Pat. No. 8,895,253, which is a continuation of U.S. application Ser. No. 13/226,323, filed Sep. 6, 2011, now abandoned, which is a continuation of U.S. application Ser. No. 11/347,179, filed Feb. 6, 2006, now U.S. Pat. No. 8,048,991, which is a continuation of U.S. application Ser. No. 09/647,544, filed Oct. 26, 2000, now U.S. Pat. No. 7,029,858, which is a national stage filing under 35 U.S.C. § 371 of International Application No. PCT/SE99/00544, filed Mar. 31, 1999, which claims benefit of Swedish Application Nos. 9801164-6 filed Apr. 2, 1998 and 9900319-6 filed Jan. 28, 1999.

FIELD OF THE INVENTION

The present invention relates to a recombinant or isolated integrin heterodimer comprising a subunit α10 and a subunit β, the subunit α10 thereof, homologues and fragments of said integrin and of said subunit α10 having similar biological activity, processes of producing the same, polynucleotides and oligonucleotides encoding the same, vectors and cells comprising the same, binding entities binding specifically to the same, and the use of the same.

BACKGROUND OF THE INVENTION

The integrins are a large family of transmembrane glycoproteins that mediate cell-cell and cell-matrix interactions (1-5). All known members of this superfamily are non-covalently associated heterodimers composed of an α- and a β-subunit. At present, 8 B-subunits (β1-β8) (6) and 16 α-subunits (α1-α9, αv, αM, αL, αX, αIIb, αE and αD) have been characterized (6-21), and these subunits associate to generate more than 20 different integrins. The β1-subunit has been shown to associate with ten different α-subunits, α1-α9 and αv, and to mediate interactions with extracellular matrix proteins such as collagens, laminins and fibronectin. The major collagen binding integrins are α1β1 and α2β1 (22-25). The integrins α3β1 and α9β1 have also been reported to interact with collagen (26, 27) although this interaction is not well understood (28). The extracellular N-terminal regions of the α and β integrin subunits are important in the binding of ligands (29, 30). The N-terminal region of the α-subunits is composed of a seven-fold repeated sequence (12, 31) containing PG and GAP consensus sequences. The repeats are predicted to fold into a β-propeller domain (32) with the last three or four repeats containing putative divalent cation binding sites. The α-integrin subunits α1, α2, αD, αE, αL, αM and αX contain a ~200 amino acid inserted domain, the I-domain (A-domain), which shows similarity to sequences in von Willebrand factor, cartilage matrix protein and complement factors C2 and B (33, 34). The I-domain is localized between the second and third FG-GAP repeats, it contains a metal ion-dependent adhesion site (MIDAS) and it is involved in binding of ligands (35-38).

Chondrocytes, the only type of cells in cartilage, express a number of different integrins including α1β1, α2β1, α3β1, α5β1, α6β1, αvβ3, and αvβ5 (39-41). It has been shown that α1β1 and α2β1 mediate chondrocyte interactions with collagen type II (25) which is one of the major components in cartilage. It has also been shown that α2β1 is a receptor for the cartilage matrix protein chondroadherin (42).

SUMMARY OF THE INVENTION

The present invention relates to a novel collagen type II binding integrin, comprising a subunit α10 in association with a subunit β, especially subunit β1, but also other β-subunits may be contemplated. In preferred embodiments, this integrin has been isolated from human or bovine articular chondrocytes, and human chondrosarcoma cells.

The invention also encompasses integrin homologues of said integrin, isolated from other species, such as bovine integrin heterodimer comprising a subunit α10 in association with a subunit β, preferably β1, as well as homologues isolated from other types of human cells or from cells originating from other species.

The present invention relates in particular to a recombinant or isolated integrin subunit α10 comprising the amino acid sequence shown in SEQ ID No. 4, and homologues and or fragments thereof having the same biological activity.

The invention further relates to a process of producing a recombinant integrin subunit α10 comprising the amino acid sequence shown in SEQ ID No. 4 or SEQ ID No. 5, or homologues or fragments thereof having similar biological activity, which process comprises the steps of
a) isolating a polynucleotide comprising a nucleotide sequence coding for a integrin subunit α10, or homologues or fragments thereof having similar biological activity,
b) constructing an expression vector comprising the isolated polynucleotide,
c) transforming a host cell with said expression vector,
d) culturing said transformed host cell in a culture medium under conditions suitable for expression of integrin subunit α10, or homologues or fragments thereof having similar biological activity, in said transformed host cell, and, optionally,
e) isolating the integrin subunit α10, or homologues or fragments thereof having the same biological activity, from said transformed host cell or said culture medium.

The integrin subunit α10, or homologues or fragments thereof having the same biological activity, can also be provided by isolation from a cell in which they are naturally present.

The invention also relates to an isolated polynucleotide comprising a nucleotide coding for an integrin subunit α10, or homologues or fragments thereof having similar biological activity, which polynucleotide comprises the nucleotide sequence shown in SEQ ID No. 1 or SEQ ID No. 2, or parts thereof.

The invention further relates to an isolated polynucleotide or oligonucleotide which hybridises to a DNA or RNA encoding an integrin subunit α10, having the amino acid sequence shown in SEQ ID No. 4 or SEQ ID No. 5, or homologues or fragments thereof, wherein said polyoligo nucleotide or oligonucleotide fails to hybridise to a DNA or RNA encoding the integrin subunit α1.

The invention relates in a further aspect to vectors comprising the above polynucleotides, and to cells containing said vectors and cells that have polynucleotides or oligonucleotides as shown in SEQ ID No. 1 or SEQ ID No. 2 integrated in their genome.

The invention also relates to binding entities having the capability of binding specifically to the integrin subunit α10 or to homologues or fragments thereof, such as proteins, peptides, carbohydrates, lipids, natural ligands, polyclonal antibodies or monoclonal antibodies.

In a further aspect, the invention relates to a recombinant or isolated integrin heterodimer comprising a subunit α10 and a subunit β, in which the subunit α10 comprises the amino acid sequence shown in SEQ ID No. 4 or SEQ ID No. 5, or homologues or fragments thereof having similar biological activity.

In a preferred embodiment thereof, the subunit β is β1.

The invention also relates to a process of producing a recombinant integrin heterodimer comprising a subunit α10 and a subunit β, in which the subunit α10 comprises the amino acid sequence shown in SEQ ID No. 4 or SEQ ID No. 5, which process comprises the steps of
   a) isolating one polynucleotide comprising a nucleotide sequence coding for a subunit α10 of an integrin heterodimer and, optionally, another polynucleotide comprising a nucleotide sequence coding for a subunit β of an integrin heterodimer, or for homologues or fragments thereof having similar biological activity,
   b) constructing an expression vector comprising said isolated polynucleotide coding for said subunit α10 in combination with an expression vector comprising said isolated nucleotide coding for said subunit β,
   c) transforming a host cell with said expression vectors,
   d) culturing said transformed host cell in a culture medium under conditions suitable for expression of an integrin heterodimer comprising a subunit α10 and a subunit β, or homologues or fragments thereof having similar biological activity, in said transformed host cell, and, optionally,
   e) isolating the integrin heterodimer comprising a subunit α10 and a subunit β, or homologues or fragments thereof having the same biological activity, from said transformed host cell or said culture medium.

The integrin heterodimer, or homologues or fragments thereof having similar biological activity, can also be provided by isolation from a cell in which they are naturally present.

The invention further relates to a cell containing a first vector, said first vector comprising a polynucleotide coding for a subunit α10 of an integrin heterodimer, or for homologues or parts thereof having similar biological activity, which polynucleotide comprises the nucleotide sequence shown in SEQ ID No. 1 or SEQ ID No. 2 or parts thereof, and, optionally, a second vector, said second vector comprising a polynucleotide coding for a subunit β of an integrin heterodimer, or for homologues or fragments thereof.

In still another aspect, the invention relates to binding entities having the capability of binding specifically to the integrin heterodimer comprising a subunit α10 and a subunit β, or to homologues or fragments thereof having similar biological activity, preferably wherein the subunit β is β1. Preferred binding entities are proteins, peptides, carbohydrates, lipids, natural ligands, polyclonal antibodies and monoclonal antibodies.

In a further aspect, the invention relates to a fragment of the integrin subunit α10, which fragment is a peptide chosen from the group comprising peptides of the cytoplasmic domain, the I-domain and the spliced domain.

In one embodiment, said fragment is a peptide comprising the amino acid sequence KLGFFAHKKIPEEEKREEKLEQ (SEQ ID No: 7).

In another embodiment, said fragment comprises the amino acid sequence from about amino acid no. 974 to about amino acid no. 1008 of SEQ ID No. 4.

In a further embodiment, said fragment comprises the amino acid sequence from about amino acid No. 162 to about amino acid No. 359 in SEQ ID No. 4.

Another embodiment of the invention relates to a polynucleotide or oligonucleotide coding for a fragment of the human integrin subunit α10. In one embodiment this polynucleotide of oligonucleotide codes for a fragment which is a peptide chosen from the group comprising peptides of the cytoplasmic domain, the I-domain and the spliced domain. In further embodiments the polynucleotide or oligonucleotide codes for the fragments defined above.

The invention also relates to binding entities having the capability of binding specifically to a fragment of the integrin subunit α10 as defined above.

The invention also relates to a process of using an integrin subunit α10 comprising the amino acid sequence shown in SEQ ID No. 4 or SEQ ID No. 5, or an integrin heterodimer comprising said subunit α10 and a subunit β, or a homologue or fragment of said integrin or subunit having similar biological activity, as a marker or target molecule of cells or tissues expressing said integrin subunit α10, which cells or tissues are of animal including human origin.

In an embodiment of this process the fragment is a peptide chosen from the group comprising peptides of the cytoplasmic domain, the I-domain and the spliced domain.

In further embodiments of said process the fragment is a peptide comprising the amino acid sequence KLGFFAHK-KIPEEEKREEKLEQ (SEQ ID No: 7), or a fragment comprising the amino acid sequence from about amino acid No. 974 to about amino acid No. 1008 of SEQ ID No. 4, or a fragment comprising the amino acid sequence from about amino acid no. 162 to about amino acid no. 359 of SEQ ID No. 4.

The subunit β is preferably β1. The cells are preferably chosen from the group comprising chondrocytes, smooth muscle cells, endothelial cells, osteoblasts and fibroblasts.

Said process may be used during pathological conditions involving said subunit α10, such as pathological conditions comprising damage of cartilage, or comprising trauma, rheumatoid arthritis and osteoarthritis.

Said process may be used for detecting the formation of cartilage during embryonal development, or for detecting physiological or therapeutic reparation of cartilage.

Said process may also be used for selection and analysis, or for sorting, isolating or purification of chondrocytes.

A further embodiment of said process is a process for detecting regeneration of cartilage or chondrocytes during transplantation of cartilage or chondrocytes.

A still further embodiment of said process is a process for in vitro studies of differentiation of chondrocytes.

The invention also comprises a process of using binding entities having the capability of binding specifically to an integrin subunit α10 comprising the amino acid sequence shown in SEQ ID No. 4 or SEQ ID No. 5, or an integrin heterodimer comprising said subunit α10 and a subunit β, or to homologues or fragments thereof having similar biological activity, as markers or target molecules of cells or tissues expressing said integrin subunit α10, which cells or tissues are of animal including human origin.

The fragment in said process may be a peptide chosen from the group comprising peptides of the cytoplasmic domain, the I-domain and the spliced domain. In preferred embodiments said fragment is a peptide comprising the amino acid sequence (SEQ ID No: 7), or a fragment comprising the amino acid sequence from about amino acid No. 974 to about amino acid No. 1008 of SEQ ID No. 4, or a fragment comprising the amino acid sequence from about amino acid No. 162 to about amino acid no. 359 of SEQ ID No. 4.

The process may also be used for detecting the presence of an integrin subunit α10 comprising the amino acid sequence shown in SEQ ID No. 4 or SEQ ID No. 5, or of an integrin heterodimer comprising said subunit α10 and a subunit β, or of homologues or fragments thereof having similar biological activity.

In a further embodiment said process is a process for determining the differentiation-state of cells during embryonic development, angiogenesis, or development of cancer.

In a still further embodiment this process is a process for detecting the presence of an integrin subunit α10, or of a homologue or fragment of said integrin subunit having similar biological activity, on cells, whereby a polynucleotide or oligonucleotide chosen from the group comprising a polynucleotide or oligonucleotide chosen from the nucleotide sequence shown in SEQ ID No. 1 is used as a marker under hybridisation conditions wherein said polynucleotide or oligonucleotide fails to hybridise to a DNA or RNA encoding an integrin subunit α1. Said cells may be chosen from the group comprising chondrocytes, smooth muscle cells, endothelial cells, osteoblasts and fibroblasts. Said integrin fragment may be a peptide chosen from the group comprising peptides of the cytoplasmic domain, the I-domain and the spliced domain, such as a peptide comprising the amino acid sequence (SEQ ID No: 7), or a fragment comprising the amino acid sequence from about amino acid no. 974 to about amino acid no. 1008 of SEQ ID No. 4, or a fragment comprising the amino acid sequence from about amino acid No. 162 to about amino acid no. 359 of SEQ ID No. 4.

In a still further embodiment the process is a process for determining the differentiation-state of cells during development, in pathological conditions, in tissue regeneration or in therapeutic and physiological reparation of cartilage. The pathological conditions may be any pathological conditions involving the integrin subunit α10, such as rheumatoid arthritis, osteoarthritis or cancer. The cells may be chosen from the group comprising chondrocytes, smooth muscle cells, endothelial cells, osteoblasts and fibroblasts.

The invention also relates to a process for determining the differentiation-state of cells during development, in pathological conditions, in tissue regeneration and in therapeutic and physiological reparation of cartilage, whereby a polynucleotide or oligonucleotide chosen from the nucleotide sequence shown in SEQ ID No. 1 is used as a marker under hybridization conditions wherein said polynucleotide or oligonucleotide fails to hybridise to a DNA or RNA encoding an integrin subunit α1. Embodiments of this aspect comprise a process, whereby said polynucleotide or oligonucleotide is a polynucleotide or oligonucleotide coding for a peptide chosen from the group comprising peptides of the cytoplasmic domain, the I-domain and the spliced domain, such as a polynucleotide or oligonucleotide coding for a peptide comprising the amino acid sequence (SEQ ID No: 7), or comprising the amino acid sequence from about amino acid No. 974 to about amino acid no. 1008 of SEQ ID No. 4, or the amino acid sequence from about amino acid No. 162 to about amino acid No. 359 of SEQ ID No. 4. Said pathological conditions may be any pathological conditions involving the integrin subunit α10, such as rheumatoid arthritis, osteoarthritis or cancer, or atherosclerosis or inflammation. Said cells may be chosen from the group comprising chondrocytes, smooth muscle cells, endothelial cells, osteoblasts and fibroblasts.

In a further aspect the invention relates to a pharmaceutical composition comprising as an active ingredient a pharmaceutical agent or an antibody which is capable of using an integrin heterodimer comprising a subunit α10 and a subunit β, or the subunit α10 thereof, or a homologue or fragment of said integrin or subunit α10 having similar biological activity, as a target molecule. An embodiment of said pharmaceutical composition is intended for use in stimulating, inhibiting or blocking the formation of cartilage, bone or blood vessels. A further embodiment comprises a pharmaceutical composition for use in preventing adhesion between tendon/ligaments and the surrounding tissue after infection, inflammation and after surgical intervention where adhesion impairs the function of the tissue.

The invention is also related to a vaccine comprising as an active ingredient an integrin heterodimer comprising a subunit α10 and a subunit β, or the subunit α10 thereof, or a homologue or fragment of said integrin or subunit α10, or DNA or RNA coding for said integrin subunit α10.

A further aspect of the invention is related to the use of the integrin subunit α10 as defined above as a marker or target in transplantation of cartilage or chondrocytes.

A still further aspect of the invention is related to a method of using binding entities having the capability of binding specifically to an integrin subunit α10 comprising the amino acid sequence shown in SEQ ID No. 4 or SEQ ID No. 5, or an integrin heterodimer comprising said subunit α10 and a subunit β, or to homologues or fragments thereof having similar biological activity, for promoting adhesion of chondrocytes and/or osteoblasts to surfaces of implants to stimulate osseointegration.

The invention is also related to the use of an integrin subunit α10 or an integrin heterodimer comprising said subunit α10 and a subunit β as a target for anti-adhesive drugs or molecules in tendon, ligament, skeletal muscle or other tissues where adhesion impairs the function of the tissue.

The invention also relates to a method of stimulating, inhibiting or blocking the formation of cartilage or bone, comprising administration to a subject a suitable amount of a pharmaceutical agent or an antibody which is capable of using an integrin heterodimer comprising a subunit α10 and a subunit β, or the subunit α10 thereof, or a homologue or fragment of said integrin or subunit α10 having similar biological activity, as a target molecule.

In another embodiment the invention is related to a method of preventing adhesion between tendon/ligaments and the surrounding tissue after infection, inflammation and after surgical intervention where adhesion impairs the function of the tissue, comprising administration to a subject a suitable amount of a pharmaceutical agent or an antibody which is capable of using a integrin heterodimer comprising a subunit α10 and a subunit β, or the subunit α10 thereof, or a homologue or fragment of said integrin or subunit α10 having similar biological activity, as a target molecule.

The invention also relates to a method of stimulating extracellular matrix synthesis and repair by activation or blockage of an integrin heterodimer comprising a subunit α10 and a subunit β, or of the subunit α10 thereof, or of a homologue or fragment of said integrin or subunit α10 having similar biological activity.

In a further aspect the invention relates to a method of in vitro detecting the presence of integrin binding entities, comprising interaction of an integrin heterodimer comprising a subunit α10 and a subunit β, or the subunit α10 thereof, or a homologue or fragment of said integrin or subunit, with a sample, thereby causing said integrin, subunit α10, or homologue or fragment thereof having similar biological activity, to modulate the binding to its natural ligand or other integrin binding proteins present in said sample.

The invention also relates to a method of in vitro studying consequences of the interaction of a human heterodimer integrin comprising a subunit α10 and a subunit β, or the subunit α10 thereof, or a homologue or fragment of said integrin or subunit, with an integrin binding entity and thereby initiate a cellular reaction. Said consequences may be measured as alterations in cellular functions.

A still further aspect of the inventions relates to a method of using DNA or RNA encoding an integrin subunit α10 or homologues or fragments thereof as a molecular target. In an embodiment of this aspect, a polynucleotide or oligonucleotide hybridises to the DNA or RNA encoding an integrin subunit α10 or homologues or fragments thereof, whereby said polynucleotide or oligonucleotide fails to hybridise to a DNA or RNA encoding en integrin subunit α1.

The invention also relates to a method of using a human heterodimer integrin comprising a subunit α10 and a subunit β, or the subunit α10 thereof, or a homologue or fragment of said integrin or subunit, or a DNA or RNA encoding an integrin subunit α10 or homologues or fragments thereof, as a marker or target molecule during angiogenesis.

BRIEF DESCRIPTION OF THE FIGURES

FIG. 2. Amino acid sequences of peptides from the bovine α10 integrin subunit (SEQ ID Nos: 26-31, respectively, in order of appearance).

FIG. 3A. Affinity purification and immunoprecipitation of the integrin subunit α10 from bovine chondrocytes.

FIG. 3B. Affinity purification and immunoprecipitation of the integrin subunit α10 from human chondrocytes.

FIG. 3C. Affinity purification and immunoprecipitation of the integrin subunit α10 from human chondrosarcoma cells.

FIG. 6. Nucleotide sequence (SEQ ID No: 1) and deduced amino acid sequence (SEQ ID No: 4) of the human α10 integrin subunit.

FIG. 12. Hybridisation of α10 mRNA in various human tissues.

FIGS. 15A-F. Partial genomic nucleotide sequence (SEQ ID No: 32) of the human integrin subunit α10 (Top protein sequence disclosed as SEQ ID Nos: 33-127; middle protein sequence disclosed as SEQ ID Nos: 128-206; bottom protein sequence disclosed as SEQ ID Nos: 207-299).

DETAILED DESCRIPTION OF THE INVENTION

Figure 1:
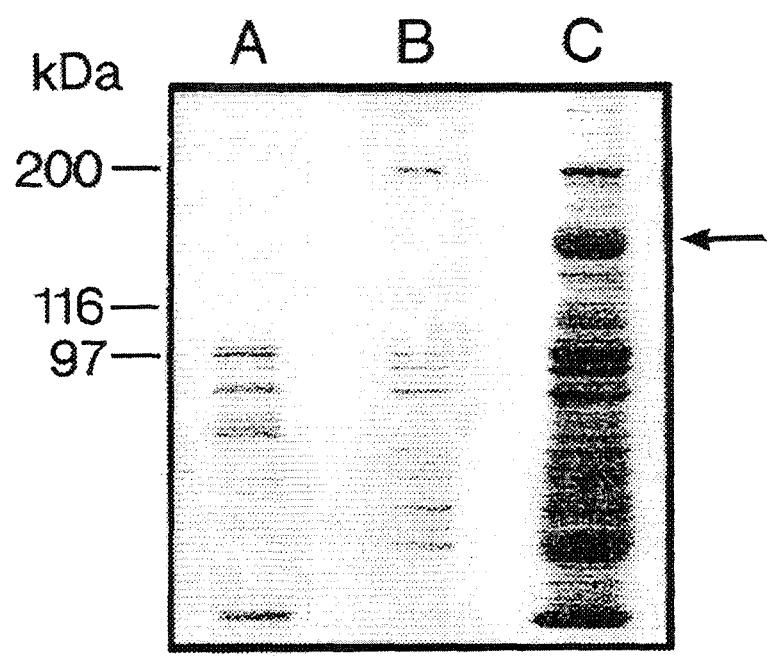
FIG. 1 Affinity purification of the α10 integrin subunit on collagen type II-Sepharose.

The present invention demonstrates that human and bovine chondrocytes express a novel, collagen type II-binding integrin in the β1-family. An earlier study presented some evidence for that human chondrosarcoma cells also express this integrin (25). Immunoprecipitation experiments using antibodies against the integrin subunit β1 revealed that this novel α-integrin subunit had an apparent molecular weight ($M_r$) of approximately 160 kDa under reducing conditions, and was slightly larger than the α2 integrin subunit. To isolate this α-subunit collagen type IT-binding proteins were affinity purified from bovine chondrocytes. The chondrocyte lysate was first applied to a fibronectin-Sepharose precolumn and the flow through was then applied to a collagen type II-Sepharose column. A protein with $M_r$ of approximately 160 kD was specifically eluted with EDTA from the collagen column but not from the fibronectin column. The $M_r$ of this protein corresponded with the $M_r$ of the unidentified β1-related integrin subunit. The 160 kD protein band was excised from the SDS-PAGE gel, digested with trypsin and the amino acid sequences of the isolated peptides were analysed.

Primers corresponding to isolated peptides amplified a 900 bp PCR-fragment from bovine cDNA which was cloned, sequenced and used for screening of a human articular chondrocyte λZapII cDNA library to obtain the human integrin α-subunit homologue. Two overlapping clones, hc1 and hc2 were isolated, subcloned and sequenced. These clones contained ⅔ of the nucleotide sequence including the 3' end of the cDNA. A third clone which contained the 5' end of the α10 cDNA, was obtained using the RACE technique. Sequence analysis of the 160 kD protein sequence showed that it was a member of the integrin α-subunit family and the protein was named α10.

The deduced amino acid sequence of α10 was found to share the general structure of the integrin α subunits described in previously published reports (6-21). The large extracellular N-terminal part of α10 contains a seven-fold repeated sequence which was recently predicted to fold into a β-propeller domain (32). The integrin subunit α10 contains three putative divalent cation-binding sites (DxD/NxD/NxxxD) (53), a single spanning transmembrane domain and a short cytoplasmic domain. In contrast to most α-integrin subunits the cytoplasmic domain of α10 does not contain the conserved sequence KXGFF(R/K)R. The predicted amino acid sequence in α10 is KLGFFAH (SEQ ID No. 8). Several reports indicate that the integrin cytoplasmic domains are crucial in signal transduction (54) and that membrane-proximal regions of both α- and β-integrin cytoplasmic domains are involved in modulating conformation and affinity state of integrins (55-57). It is suggested that the GFFKR motif in α-chains are important for association of integrin subunits and for transport of the integrin to the plasma membrane (58). The KXGFFKR domain has been shown to interact with the intracellular protein calreticulin (59) and interestingly, calreticulin-null embryonic stem cells are deficient in integrin-mediated cell adhesion (60). It is therefore possible that the sequence (SEQ ID No. 8) in α10 has a key function in regulating the affinity between α10β1 and matrix proteins.

Integrin α subunits are known to share an overall identity of 20-40% (61). Sequence analysis showed that the α10 subunit is most closely related to the I-domain containing α-subunits with the highest identity to a α1 (37%) and α2 (35%). The integrins α1β1 and α2β1 are known receptors for both collagens and laminins (24; 62; 63) and we have also recently demonstrated that α2β1 interacts with the cartilage matrix protein chondroadherin (42). Since α10β1 was isolated on a collagen type II-Sepharose, we know that collagen type II is a ligand for α10β1. We have also shown by affinity purification experiments that α10β1 interacts with collagen type I but it remains to be seen whether laminin or chondroadherin are also ligands for this integrin.

The α10 associated β-chain migrated as the β1 integrin subunit both under reducing and non-reducing conditions. To verify that the α10 associated β-chain indeed is β1, chondrocyte lysates were immunoprecipitated with antibodies against α10 or β1 followed by Western blot using antibodies against the β1-subunit. These results clearly demonstrated that α10 is a member of the β1-integrin family. However, the possibility that α10 combine also with other β-chains can not be excluded.

A polyclonal peptide antibody raised against the cytoplasmic domain of α10 precipitated two protein bands with $M_r$ of approximately 160 kD (α10) and 125 kD (β1) under reducing conditions. Immunohistochemistry using the α10-antibody showed staining of the chondrocytes in tissue sections of human articular cartilage. The antibody staining was clearly specific since preincubation of the antibody with the α10-peptide completely abolished the staining. Immunohistochemical staining of mouse limb sections from embryonic tissue demonstrated that α10 is upregulated during condensation of the mesenchyme. This indicates that the integrin subunit α10 is important during the formation of cartilage. In 3 day old mice α10 was found to be the dominating collagen binding integrin subunit which point to that α10 has a key function in maintaining normal cartilage functions.

Expression studies on the protein and mRNA level show that the distribution of α10 is rather restrictive. Immunohistochemistry analyses have shown that α10 integrin subunit is mainly expressed in cartilage but it is also found in perichondrium, periosteum, ossification groove of Ranvier, in fascia surrounding tendon and skeletal muscle and in the tendon-like structures in the heart valves. This distribution point to that α10 integrin subunit is present also on fibroblasts and osteoblasts. PCR amplification of cDNA from different cell types revealed the presence of an alternatively spliced α10 integrin subunit. This spliced α10 was dominating in fibroblasts which suggests that α10 in fibro-blasts may have a different function compared to α10 present on chondrocytes.

Expression of the integrin subunit α10 was found to decrease when chondrocytes were cultured in monolayer. In contrast, the expression of α10 was found to increase when the cells were cultured in alginate beads. Since the latter culturing model is known to preserve the phenotype of chondrocytes the results suggest that α10 can function as marker for a differentiated chondrocyte.

Adhesion between tendon/ligaments and the surrounding tissue is a well-known problem after infection, injury and after surgical intervention. Adhesion between tendon and tendon sheets impairs the gliding function and cause considerable problems especially during healing of tendons in e.g. the hand and fingers leading to functional incapacity. The localisation of the α10 integrin subunit in the fascia of tendon and skeletal muscle makes α10 a possible target for drugs and molecules with anti-adhesive properties that could prevent impairment of the function of tendon/ligament. The integrin subunit α10 can also be a target for drugs or molecules with anti-adhesive properties in other tissues where adhesion is a problem.

EXAMPLES

Example 1

Affinity Purification of the α10 Integrin Subunit on Collagen Type II-Sepharose.

Materials and Methods

Bovine chondrocytes, human chondrocytes or human chondrosarcoma cells were isolated as described earlier [Holmvall et al, Exp Cell Res, 221, 496-503 (1995), Camper et al, JBC, 273, 20383-2D389 (1998)]. A Triton X-100 lysate of bovine chondrocytes was applied to a fibronectin-Sepharose precolumn followed by a collagen type II-Sepharose column and the integrin subunit α10 was eluted from the collagen type II-column by EDTA (Camper et al, JBC, 273, 20383-20389 (1998). The eluted proteins were precipitated by methanol/chloroform, separated by SDS-PAGE under reducing conditions and stained with Coomassie blue. (Camper et al, JBC, 273, 20383-2D389 (1998). Peptides from the α10 protein band were isolated by in-gel digestion with a trypsin and phase liquid chromatography and sequenced by Edman degradation (Camper et al, JBC, 273, 20383-20389 (1998).

Results

FIG. 1 shows EDTA-eluted proteins from the fibronectin-Sepharose (A), flowthrough from the collagen type II-Sepharose column (B) and EDTA-eluted proteins from the collagen type II-Sepharose (C). The α10 integrin subunit (160 kDa) which was specifically eluted from the collagen type II column is indicated with an arrow. FIG. 2 shows the amino acid sequences of six peptides that were isolated from the bovine integrin subunit α10. FIGS. 3 *a, b,* and *c* show that the α10 integrin subunit is present on bovine chondrocytes (3*a*), human chondrocytes (3*b*) and human chondrosarcoma cells (3*c*). The affinity for collagen type II, the coprecipitation with β1-integrin subunit and the molecular weight of 160 kDa under reducing conditions identify the α10 integrin subunit on the different cells. These results show that α10 can be isolated from chondrocytes and from chondrosarcoma cells.

Example 2

Amplification of PCR Fragment Corresponding to Bovine α10 Integrin Subunit.

Materials and Methods

Figure 4:
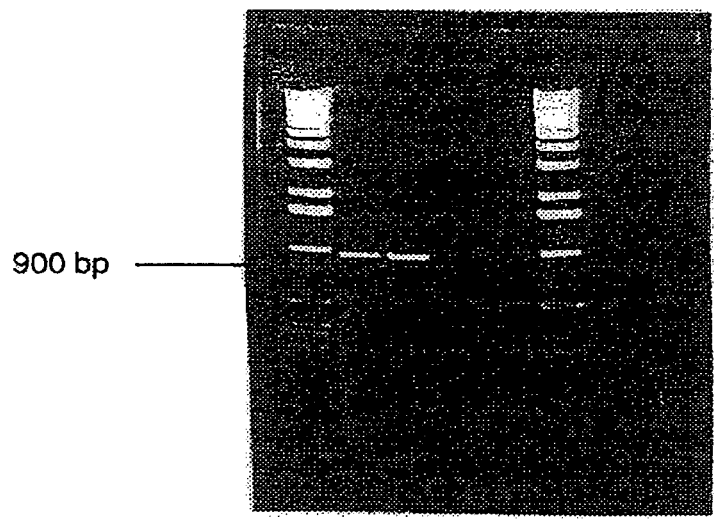
FIG. 4. A 900 bp PCR-fragment corresponding to the bovine integrin subunit α10.

The degenerate primers (SEQ ID No: 9) ((SEQ ID No: 10), forward) and (SEQ ID No: 11) ((SEQ ID No: 12) reverse) were used in PCR (Camper et al, JBC, 273, 2038320389 (1998) to amplify the nucleotide sequence corresponding to the bovine peptide 1 (FIG. 2). A 900 bp PCR-fragment was then amplified from bovine, cDNA using an internal specific primer (SEQ ID No: 13) (SEQ ID No: 14), forward) corresponding to the cloned nucleotide sequence of peptide 1 together with the degenerate primer (SEQ ID No: 15) ((SEQ ID No: 16) PGHWDR, reverse) corresponding to the bovine peptide 2 (FIG. 2). Mixed bases were used in positions that were twofold degenerate and inosines were used in positions that are three- or fourfold degenerate. mRNA isolation and CDNA synthesis was done as earlier described (Camper et al, JBC, 273, 20383-20389 (1998)). The purified fragment was cloned, purified and sequenced as earlier described (Camper et al, JBC, 273, 20383-20389 (1998)).
Results The nucleotide sequence of peptide 1 (FIG. 2) was obtained by PCR-amplification, cloning and sequencing of bovine cDNA. From this nucleotide sequence an exact primer was designed and applied in PCR-amplification with degenerate primers corresponding to peptides 2-6 (FIG. 2). Primers corresponding to peptides 1 and 2 amplified a 900 bp PCR-fragment from bovine cDNA (FIG. 4).

Example 3

Figure 5:
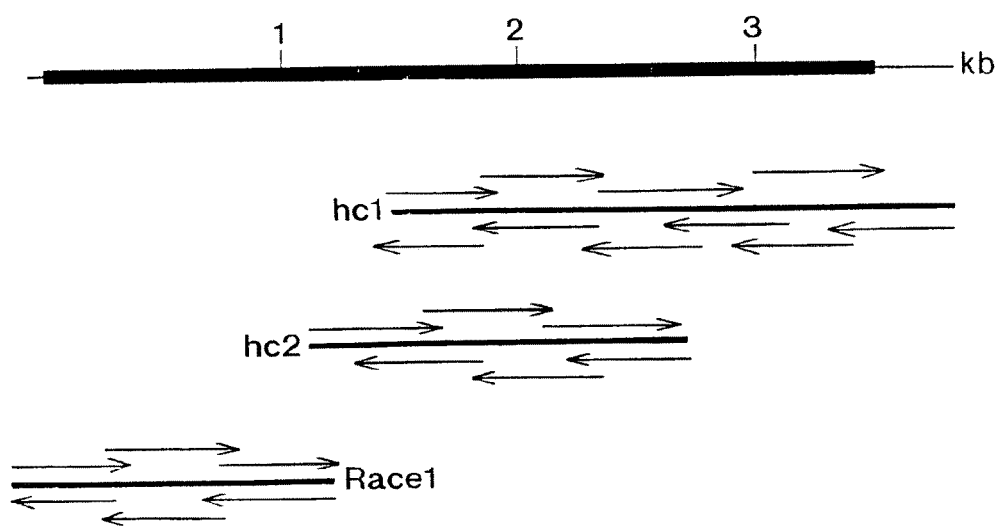
FIG. 5. Schematic map of the three overlapping α10 clones.
Figure 6:
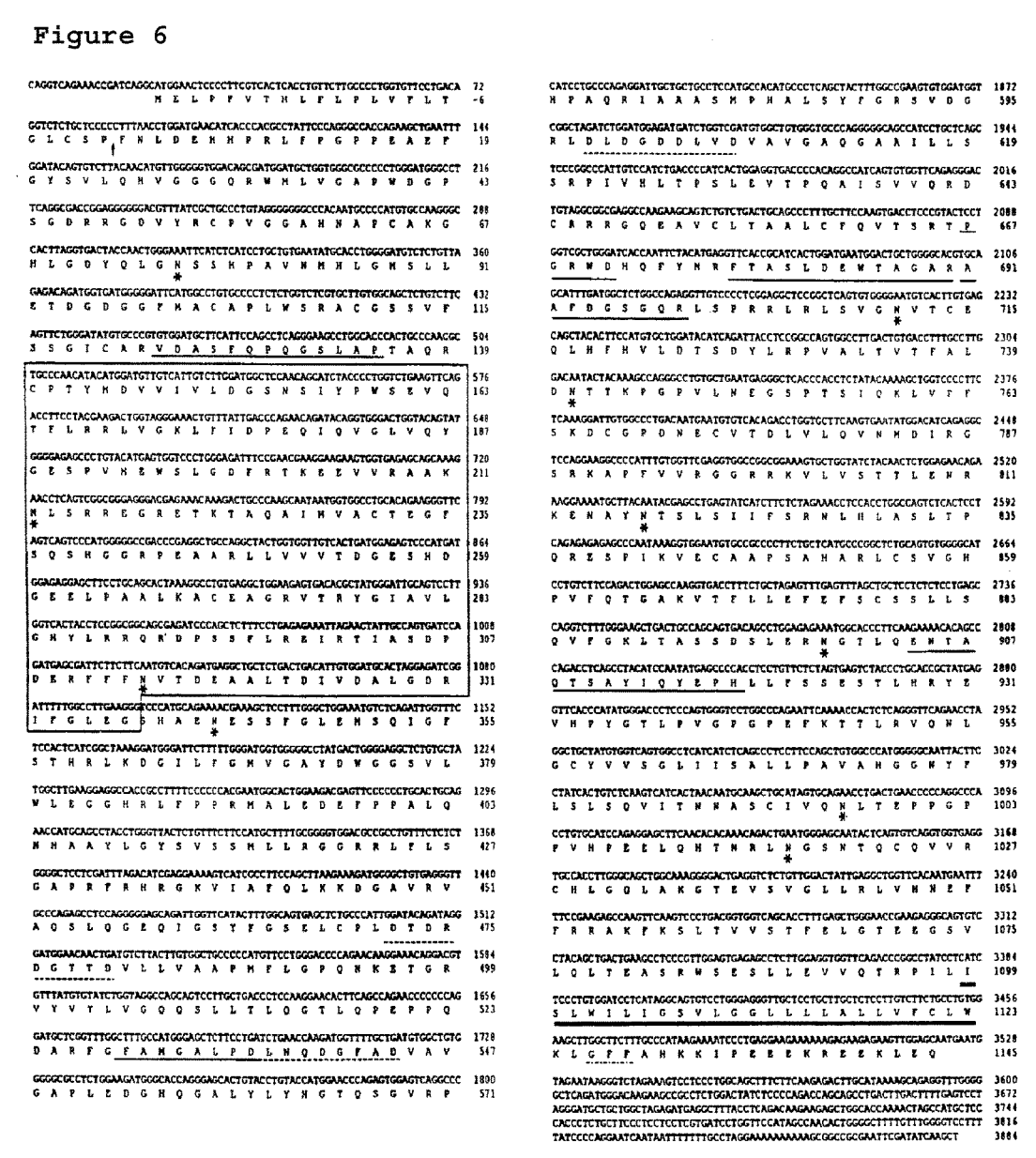

Cloning and Sequence Analysis of the Human α10 Integrin Subunit
Material and Methods The cloned 900 bp PCR-fragment, corresponding to bovine α10-integrin, was digoxigenin-labelled according to the DIG DNA label-ling kit (Boehringer Mannheim) and used as a probe for screening of a human articular chondrocyte λZapII cDNA library (provided by Michael Bayliss, The Royal Veterinary Basic Sciences, London, UK) (52). Positive clones containing the pBluescript SK+ plasmid with the cDNA insert were rescued from the ZAP vector by in vivo excision as described in the ZAP-cDNA® synthesis kit (Stratagene). Selected plasmids were purified and sequenced as described earlier (Camper et al, JBC, 273, 20383-20389 (1998)) using T3, T7 and internal specific primers. To obtain CDNA that encoded the 5' end of α10 we designed the primer (SEQ ID No: 17) (reverse; residue 1254-1280 in α10 CDNA) and used it for rapid amplification of the CDNA 5' end (RACE) as described in the Marathon™ cDNA Amplification kit (Clontech INC., Palo Alto, Calif.).
Results Two overlapping clones, hc1 and hc2 (FIG. 5), were isolated, subcloned and sequenced. These clones contained ⅔ of the nucleotide sequence including the 3' end of the cDNA. A third clone (race 1; FIG. 5), which contained the 5' end of the α10 cDNA, was obtained using the RACE technique. From these three overlapping clones of α10 cDNA, 3884 nucleotides were sequenced The nucleotide sequence and deduced amino acid sequence is shown in FIG. 6. The sequence contains a 3504-nucleotide open reading frame that is predicted to encode a 1167 amino acid mature protein. The signal peptide cleavage site is marked with an arrow, human homologues to bovine peptide sequences are underlined and the I-domain is boxed. Metal ion binding sites are indicated with a broken underline, potential N-glycosylation sites are indicated by an asterisk and the putative transmembrane domain is double underlined. The normally conserved cytoplasmic sequence is indicated by a dot and dashed broken underline.

Sequence analysis demonstrate that α10 is a member of the integrin α-subunit family.

Example 4

Identification of a Clone Containing a Splice Variant of α10

One clone which was isolated from the human chondrocyte library (see Example 3) contained a sequence that was identical to the sequence of α10 integrin subunit except that the nucleotides between nt positions 2942 and 3055 were deleted. The splice variant of α10 was verified in PCR experiment using primers flanking the splice region (see FIGS. 14A-B).

Example 5

Identification of α10 Integrin Subunit by Northern Blot
Material and Methods

Figure 7:
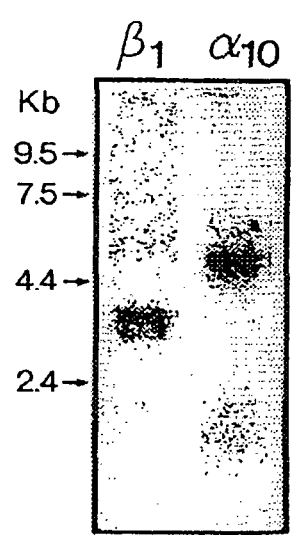
FIG. 7. Northern blot of integrin α10 mRNA.

Bovine chondrocyte mRNA was purified using a QuickPrep®Micro mRNA Purification Kit (Pharmacia Biotech, Uppsala, Sweden), separated on a 1 agarose-formaldehyde gel, transferred to nylon membranes and immobilised by UV crosslinking. cDNA-probes were $^{32}P$ labelled with Random Primed DNA Labeling Kit (Boehringer Mannheim). Filters were prehybridised for 2-4 hours at 42° C. in 5×SSE, 5×Denharts solution, 0.1% SDS, 50 µg/ml salmon sperm DNA and 50% formamide and then hybridized over night at 42° C. with the same solution containing the specific probe (0.5-1×106 cpm/ml). Specifically bound cDNA probes were analysed using the phosphoimager system (Fuji). Filters were stripped by washing in 0.1% SDS, for 1 hour at 8000 prior to re-probing. The α10-integrin cDNA-probe was isolated from the race 1-containing plasmid using the restriction enzymes BamHI (GIBCO BRL) and NcoI (Boehringer Mannheim). The rat β1-integrin cDNA probe was a kind gift from Staffan Johansson, Uppsala, Sweden.
Results Northern blot analysis of mRNA from bovine chondrocytes showed that a human α10 cDNA-probe hybridised with a single mRNA of approximately 5.4 kb (FIG. 7). As a comparison, a cDNA-probe corresponding to the integrin subunit α1 was used. This cDNA-probe hybridised a mRNAband of approximately 3.5 kb on the same filter. These results show that a cDNA-probe against α10 can be used to identify the α10 integrin subunit on the mRNA level.

Example 6

Preparation of Antibodies Against the Integrin Subunit α10

A peptide corresponding to part of the α10 cytoplasmic domain, Ckkipeeekreekle (SEQ ID No: 25, see FIG. 6) was synthesized and conjugated to keyhole limpet hemocyanin (KLH). Rabbits were immunized with the peptide-KLH conjugate to generate antiserum against the integrin subunit α10. Antibodies recognizing α10 were affinity purified on an peptide-coupled column (Innovagen AB).

Example 7

Immunoprecipitation of the Integrin Subunit α10 from Chondrocytes
Material and Methods Human chondrocytes were $^{125}I$ . . . labelled, lyzed with Triton X-100 and immunoprecipitated as earlier described (Holmvall et al, Exp Cell Res, 221, 496-503 (1995), Camper et al, JBC, 273, 20383-20389 (1998)). Triton X-100 lysates of 125I-labeled human chondrocytes were immunoprecipitated with polyclonal antibodies against the integrin subunits β1, α1, α2, α3 or α10. The immunoprecipitated proteins were separated by SDS-PAGE (4-12%) under non-reducing conditions and visualised using a phosphoimager. Triton X-100 lysates of human chondrocytes immunoprecipitated with α10 or β1 were separated by SDS-PAGE (8%) under non-reducing conditions and analysed by Western blot using the polyclonal β1 antibody and chemiluminescent detection as described in Camper et al, JBC, 273, 20383-20389 (1998).

Results

Figure 8A:
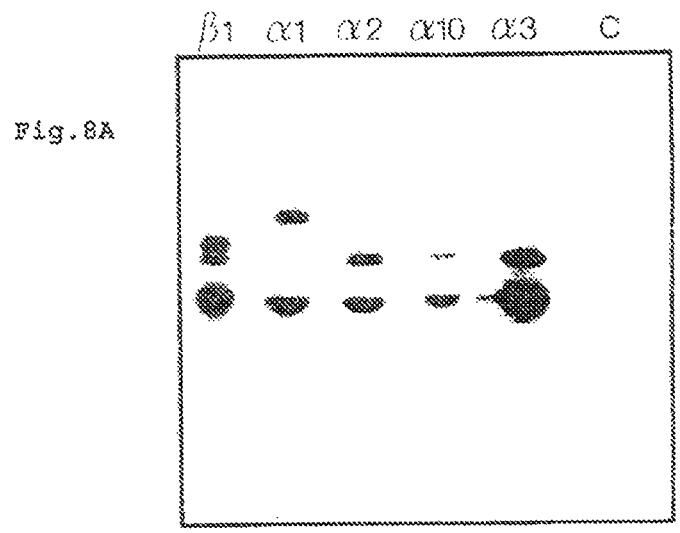
FIG. 8A: Immunoprecipitation of the α10 integrin subunit from human chondrocytes using antibodies against the cytoplasmic domain of α10.
Figure 8B:
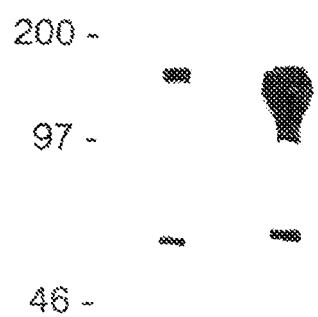
FIG. 8B: Western blot of the α10 associated β-chain.

The polyclonal peptide antibody, raised against the cytoplasmic domain of α10, precipitated two protein bands with $M_r$ of approximately 160 kD (α10) and 125 kD (β1) under reducing conditions. The α10 associated β-chain migrated as the β1 integrin subunit (FIG. 8a). To verify that the α10 associated β-chain in choridrocytes indeed is β1, chondrocyte lysates were immunoprecipitated with antibodies against α10 orb β1 followed by Western blot using antibodies against the β1-subunit (FIG. 8b). These results clearly demonstrated that α10 is a member of the β1-integrin family. However, the results do not exclude the possibility that α10 can associate with other β-chains in other situations.

Example 8

Figure 9A:
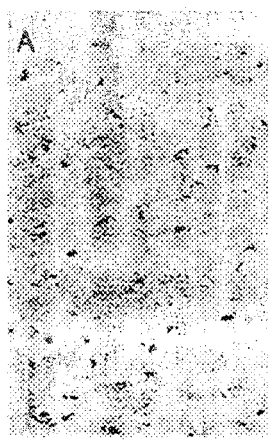
FIGS. 9A, 9B and 9C. Immunostaining of α10 integrin in human articular cartilage.
Figure 9B:
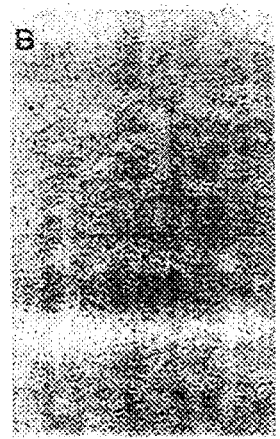
Figure 9C:
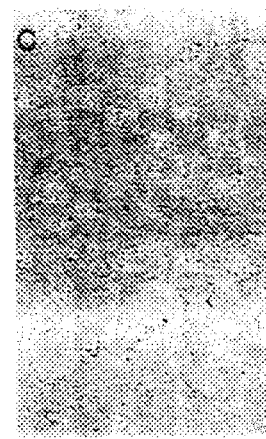

Immunohistochemical Staining of the Integrin Subunit α10 in Human and Mouse Cartilage
Material and Methods Frozen sections of adult cartilage (trochlear groove) obtained during surgery (provided by Anders Lindahl, Salgrenska Hospital, Gothenburg, Sweden and frozen sections from of 3 day old mouse limb were fixed and prepared for immunohistochemistry as earlier described (Camper et al, JBC, 273, 20383-20389 (1998)). Expression of α10 integrin subunit was analysed using the polyclonal antibody against the cytoplasmic domain as a primary antibody (see Example 6) and a secondary antibody conjugated to peroxidase.
Results FIG. 9 show immunostaining of human adult articular cartilage.

The α10-antibody recognising the cytoplasmic domain of α10 stained the chondrocytes in tissue sections of human articular cartilage (A). The staining was depleted when the antibody was preincubated with the α10-peptide (B). A control antibody recognizing the α9 integrin subunit did not bind to the chondrocyte (C).

Figure 10A:
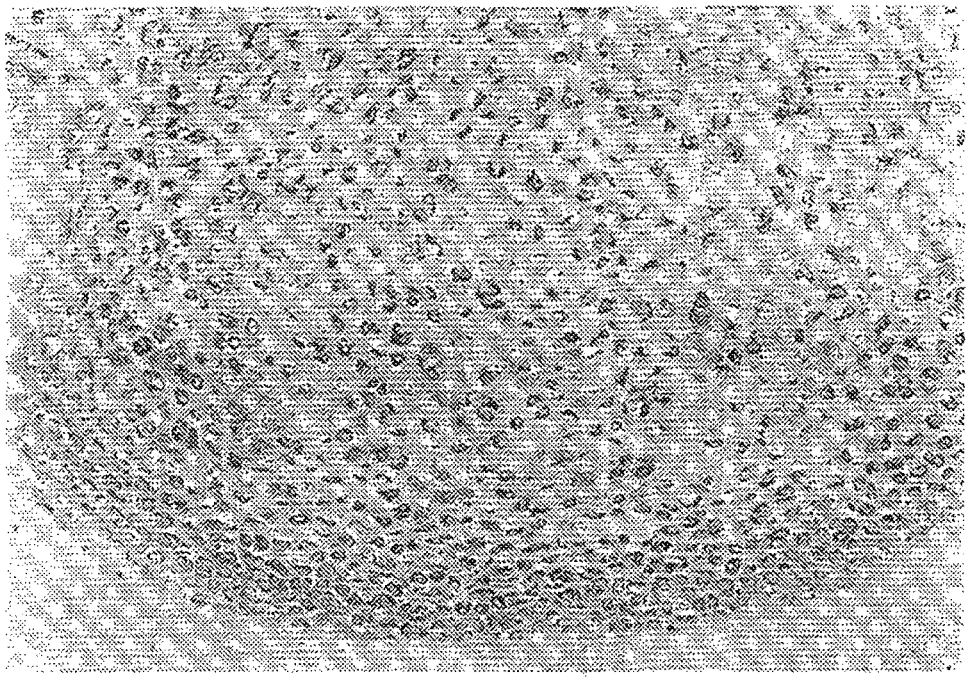
FIGS. 10A and 10B. Immunostaining of α10 integrin in 3 day mouse limb cartilage.
Figure 10B:

FIG. 10 shows that the α10 antibody stain the majority of chondrocytes in the growing bone anlage (a and b). The α10 antibody also recognised cells in the ossification groove of Ranvier (b), especially the osteoblast in the bone bark which are lining the cartilage in the metaphys are highly positive for α10. The cells in the ossification groove of Ranvier are believed to be important for the growth in diameter of the bone. The integrin subunit α10 is also highly expressed in perichondrium and periosteum. Cell in these tissues are likely important in the repair of the cartilage tissue. The described localisation of the integrin subunit α10 suggest that this integrin is important for the function of the cartilage tissue.

Example 9

Immunohistochemical Staining of the Integrin Subunit α10 During Mouse Development
Material and Methods Frozen sections from mouse embryos (13.5 days) were investigated for expression of α10 by immunohistochemistry as described in Camper et al, JBC, 273, 20383-20389 (1998). Expression of α10 integrin subunit was analysed using the polyclonal antibody against the cytoplasmic domain as a primary antibody (see Example 6) and a secondary antibody conjugated to peroxidase. The embryo sections were also investigated for expression of integrin subunit α1 (monoclonal antibody from Pharmingen) and collagen type II (monoclonal antibody, kind gift from Dr John Mo, Lund University, Sweden).

Results

Figure 11A:
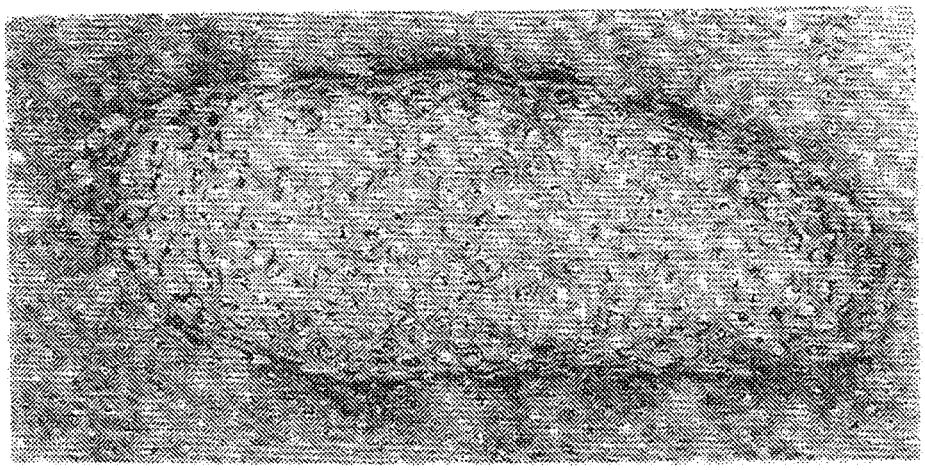
FIGS. 11A, 11B, and 11C. Immunostaining of α10 integrin in β.5 day mouse embryo.
Figure 11B:
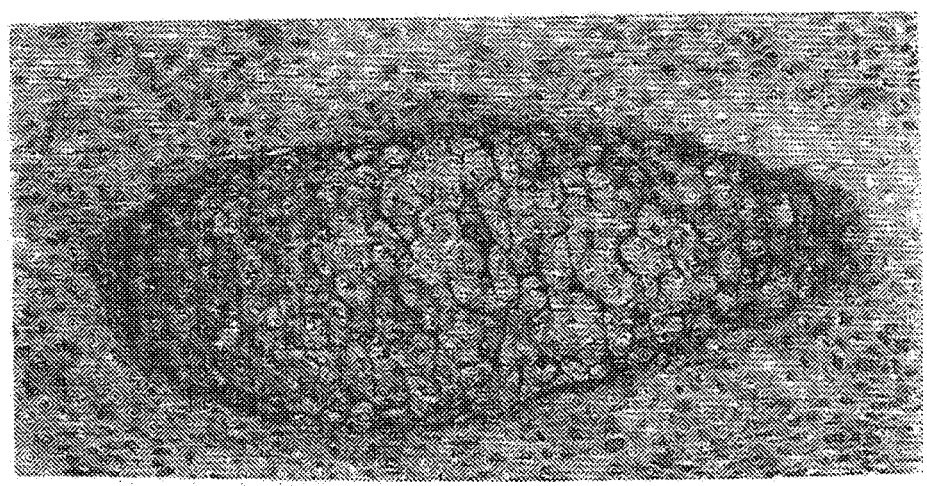
Figure 11C:
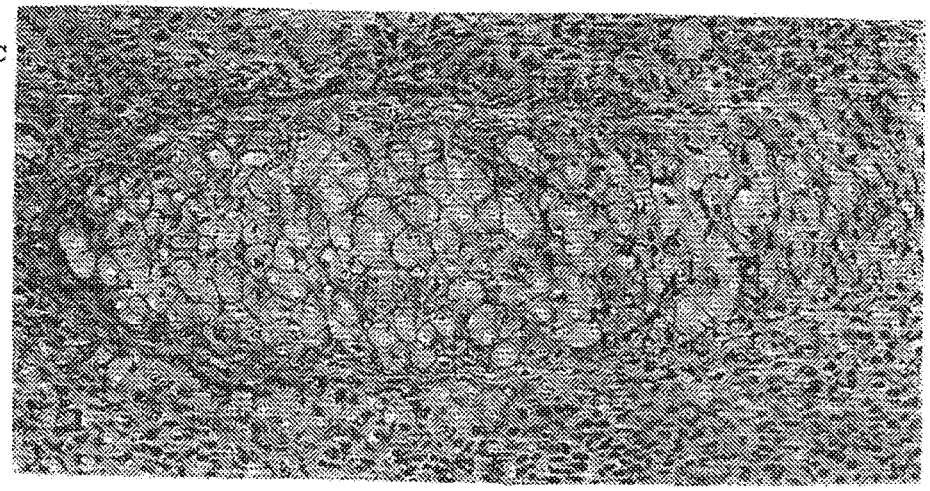

FIG. 11 show that α10 integrin subunit is unregulated in the limb when the mesenchymal cells undergo condensation to form cartilage (a). Especially the edge of the newly formed cartilage has high expression of α10. The formation of cartilage is verified by the high expression of the cartilage specific collage type II (b). The control antibody against α1 integrin subunit showed only weak expression on the cartilage (c). In other experiments expression of α10 was found in all cartilage containing tissues in the 3 day old mouse including limbs, ribs and vertebrae. The upregulation of α10 during formation of cartilage suggest that this integrin subunit is important both in the development of cartilage and bone and in the repair of damaged cartilage tissue.

Example 10 mRNA Expression of α10 in Tissues Other than Articular Cartilage
Material and Methods Expression of α10 integrin subunit was examined on the mRNA level in different human tissues. A Northern dot blot with immobilised mRNA from the listed tissues in FIG. 12 was hybridised with an α10 integrin cDNA probe isolated from the race 1-containing plasmid using the restriction enzymes BamHI and NcoI. The degree of hybridisation was analysed using a phospho imager. The following symbols denote mRNA level in increasing order: −, ++, +++, ++++.
Results Analysis of the hybridised mRNA showed that α10 was expressed in aorta, trachea, spinal cord, heart, lung, and kidney (FIG. 12). All other tissues appeared negative for α10 expression. These results point to a restricted distribution of the α10 integrin subunit.

Example 11

Figure 13A:
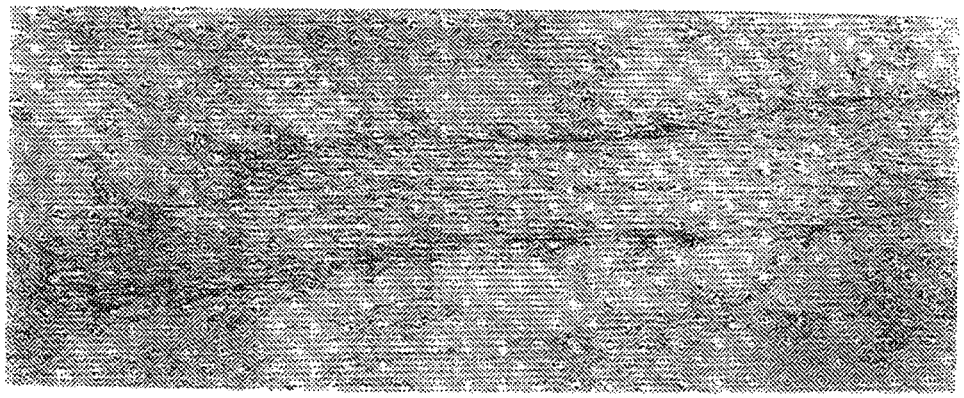
FIGS. 13A, 13B and 13C. Immunostaining of fascia around tendon (FIG. 13A), skeletal muscle (FIG. 13B), and heart valves (FIG. 13C) in 3 day mouse limb.
Figure 13B:
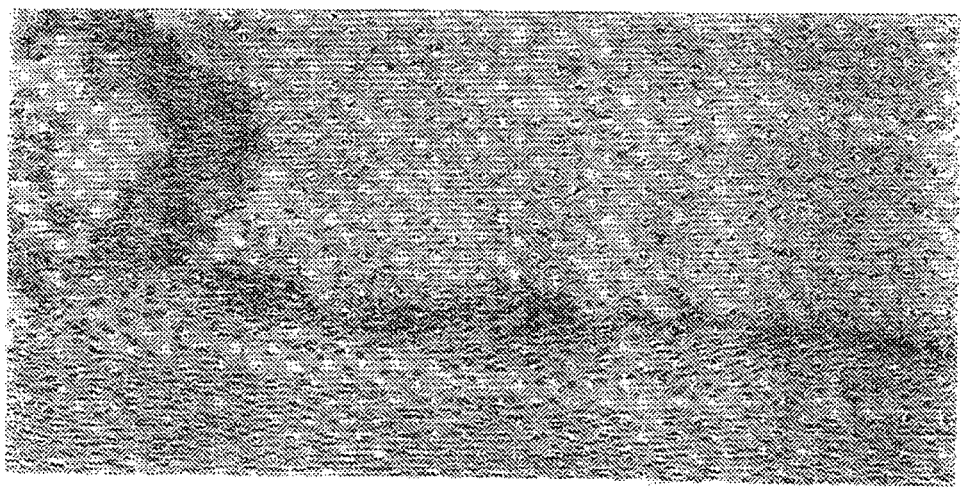
Figure 13C:
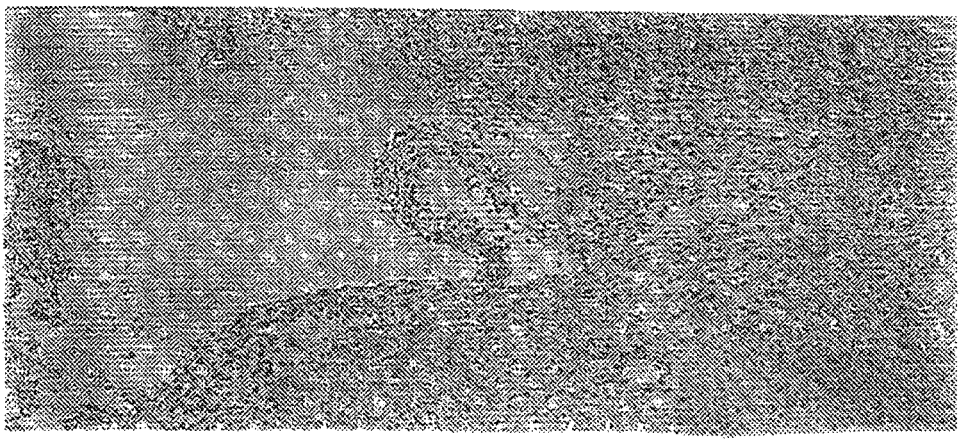

Immunohistochemical Staining of α10 in Fascia Around Tendon and Skeletal Muscle and in Tendon Structures in Heart Valves.
Materials and Methods Frozen sections of adult cartilage (trochlear groove) obtained during surgery (provided by Anders Lindahl, Salgrenska Hospital, Gothenburg, Sweden and frozen sections from of 3 day old mouse limb were fixed and prepared for immunohistochemistry as earlier described (Camper et al, JBC, 273, 20383-20389 (1998)). Expression of α10 integrin subunit was analysed using the polyclonal antibody against the cytoplasmic domain as a primary antibody (see Example 6) and a secondary antibody conjugated to peroxidase.
Results As shown in FIG. 13 expression of α10 was found in the fascia surrounding tendon (a) and skeletal muscle (b) and in the tendon structures in the heart valves (c). This localisation suggest that α10 can bind to other matrix molecules in addition to the cartilage specific collagen type II. The localisation of the integrin α10 on the surface of tendons indicate that α10 can be involved in unwanted adhesion that often occurs between tendon/ligaments and the surrounding tissue after infection, injury or after surgery.

Example 12 mRNA Expression of α10 Integrin Subunit in Chondrocytes, Endothelial Cells and Fibroblasts.
Material and Methods Isolation of mRNA, synthesis of cDNA and PCR amplification was done as earlier described (Camper et al, JBC, 273, 20383-20389 (1998))

Results

Figure 14A:
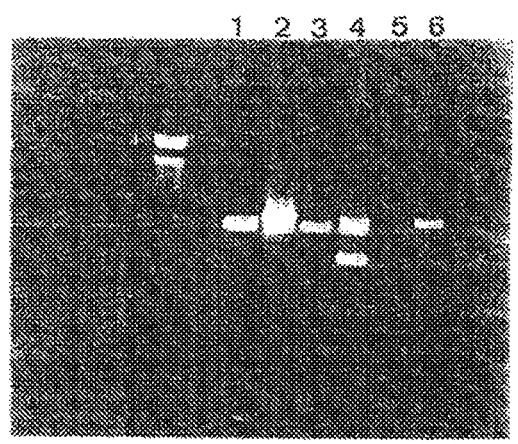
FIGS. 14A and 14B. PCR fragments corresponding to α10 integrin subunit from human chondrocytes, human endothelial cells, human fibroblasts and rat tendon.
Figure 14B:
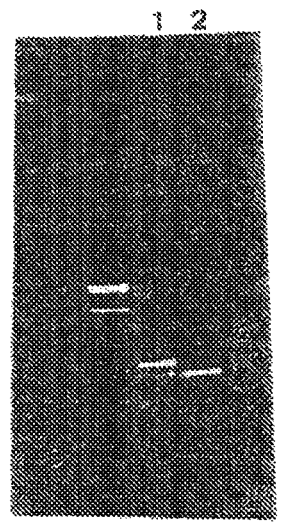

FIGS. 14A-B show PCR amplification of α10 cDNA from human articular chondrocytes (lanes A6 and B1), human umbilical vein endothelial cells (lane A2), human fibroblasts (lane A4) and rat tendon (FIG. 14*b*, lane B2). Lanes 1, 3, and 5 in FIG. 14A show amplified fragments corresponding to the integrin subunit α2 in endothelial cells, fibroblasts and chondrocytes, respectively. cDNA-primers corresponding to the α10 sequence positions nt 2919-2943 (forward) and nt 3554-3578 (reverse) (see FIG. 6) were used to amplify α10 cDNA from the different cells. The figure shows that α10 was amplified in all three cell types. Two fragments of α10 was amplified which represent the intact form of α10 (larger fragment) and a splice variant (smaller fragment). The larger fragment was dominating in chondrocytes while the smaller fragment was more pronounced in tendon (B2).

Example 13

Construction of α10 mammalian expression vector. The full length protein coding sequence of α10 (combined from 3 clones, see FIG. 6) was inserted into the mammalian expression vector, pcDNA3.1/Zeo (Invitrogen). The vector contains SV40 promoter and Zeosin selection sequence. The α10 containing expression vector was transfected into cells that express the β1-integrin subunit but lack expression of the α10 subunit. Expression of the α10 integrin subunit on the cell surface can be analysed by immunoprecipitation and/or flow cytometry using antibodies specific for α10. The ligand binding capacity and the function of the inserted α10 integrin subunit can be demonstrated in cell adhesion experiment and in signalling experiments.

Example 14

Construction of Mammalian Expression Vector Containing a Splice Variant of α10.

The full length protein coding sequence of the splice variant of α10 (nt 2942-nt3055 deleted) was inserted into the mammalian expression vector pcDNA3 (see Example 13). Expression and function of the splice variant can be analysed as described in example 13 and compared with the intact α10 integrin subunit.

Example 15

Figure 15B:
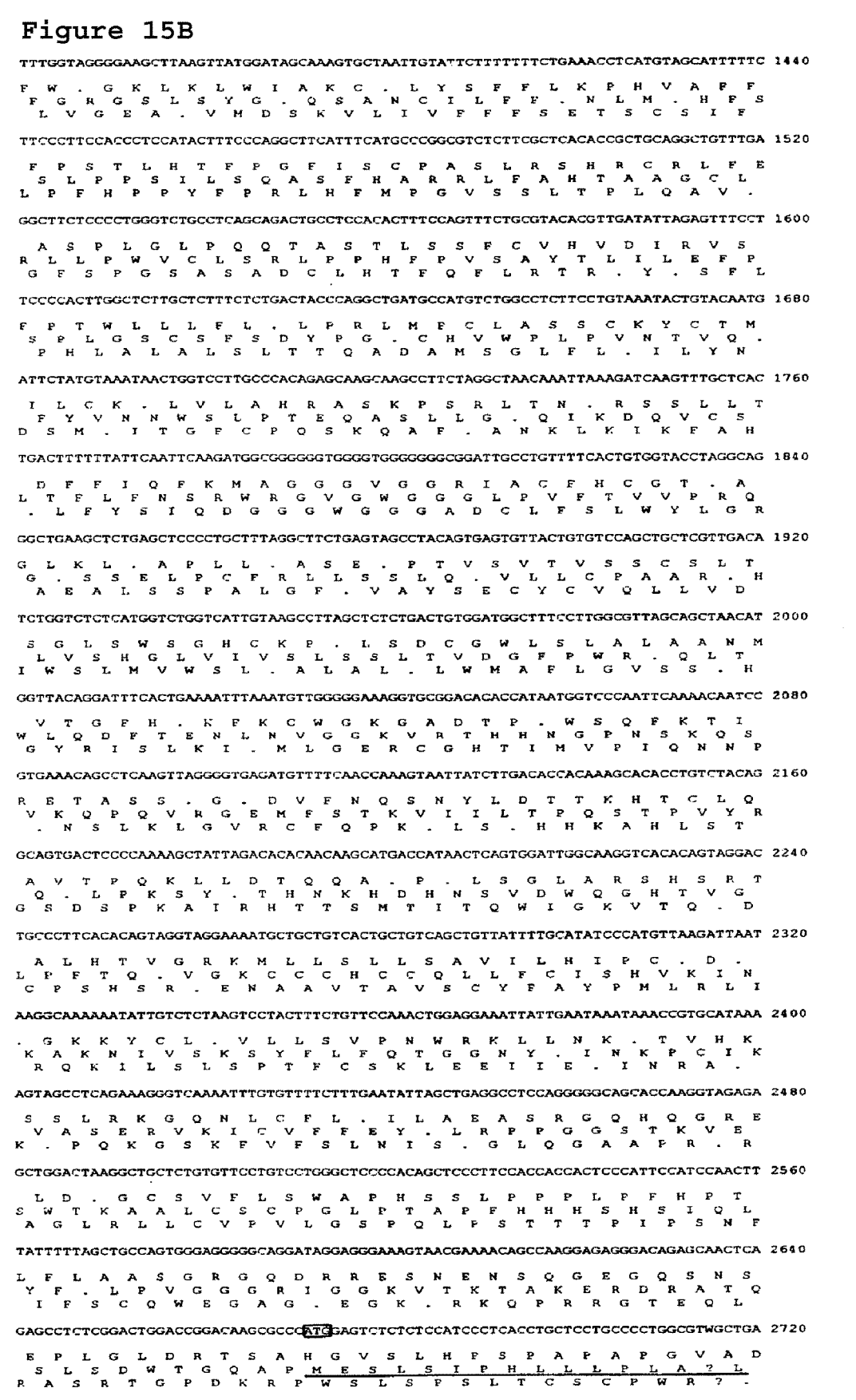
Figure 15D:
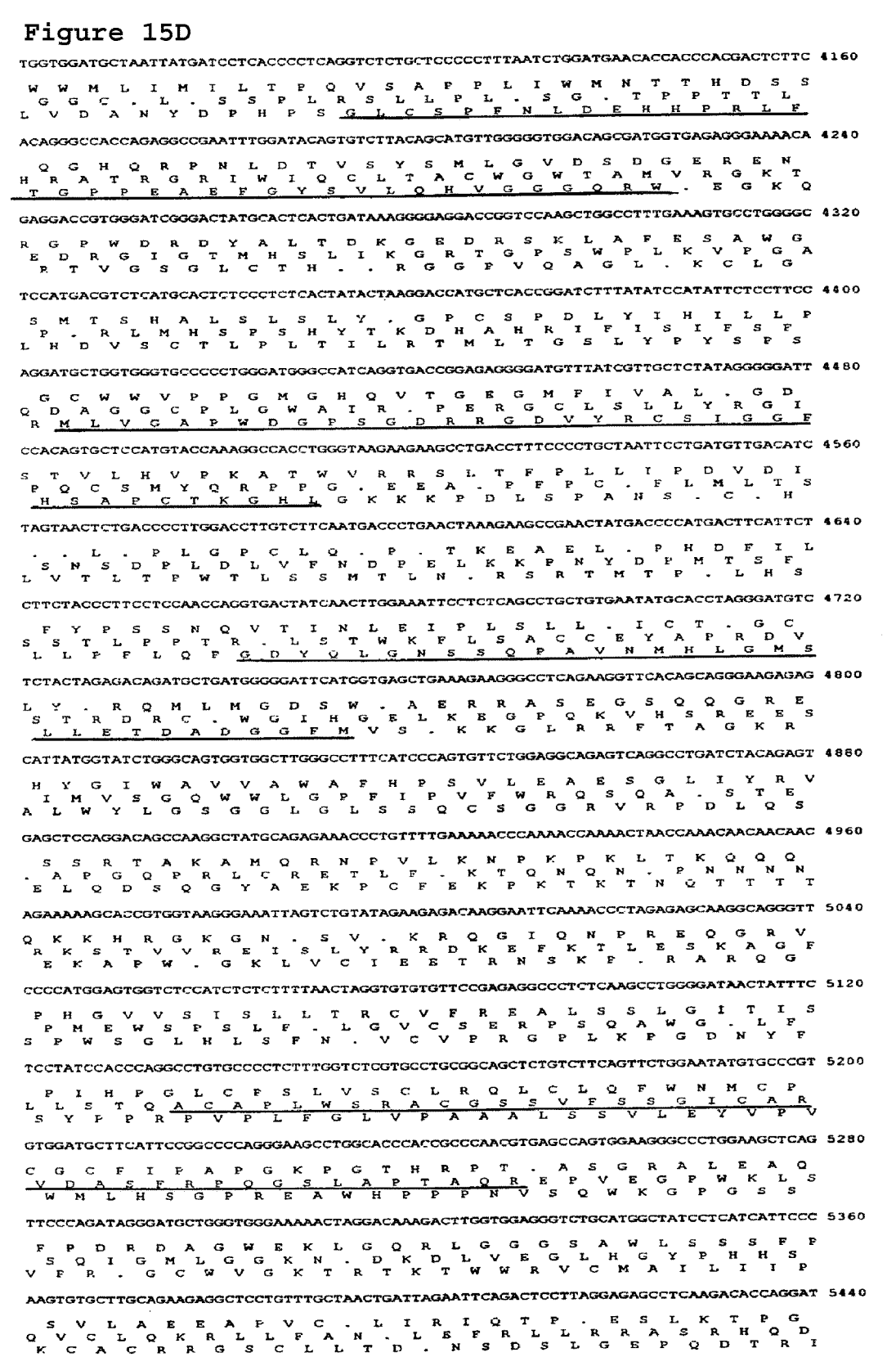

Partial Isolation and Characterisation of the α10 Integrin Genomic DNA
Material and Methods Human α10 cDNA, isolated from the race 1-containing plasmid using the restriction enzymes BamHI (GIBCO BRL) and NcoI (Boehringer Mannheim), was $^{32}$P-labelled and used as a probe for screening of a mouse 129 cosmid library (provided by Reinhard Fässler, Lund University). Positive clones were isolated and subcloned. Selected plasmids were purified and sequenced as described earlier (Camper et al, JBC, 273, 20383-20389 (1998)) using T3, T7 and internal specific primers. Primers corresponding to mouse genomic DNA were then constructed and used in PCR to amplify and identify the genomic sequence of α10 from the cosmid clones.
Results FIG. 15 shows 7958 nt of the α10 gene. This partial genomic DNA sequence of α10 integrin contains 8 exons, and a Kozak sequence. The mouse genomic α10 sequence was used to generate a targeting vector for knockout experiments.

Example 16

Figure 16:
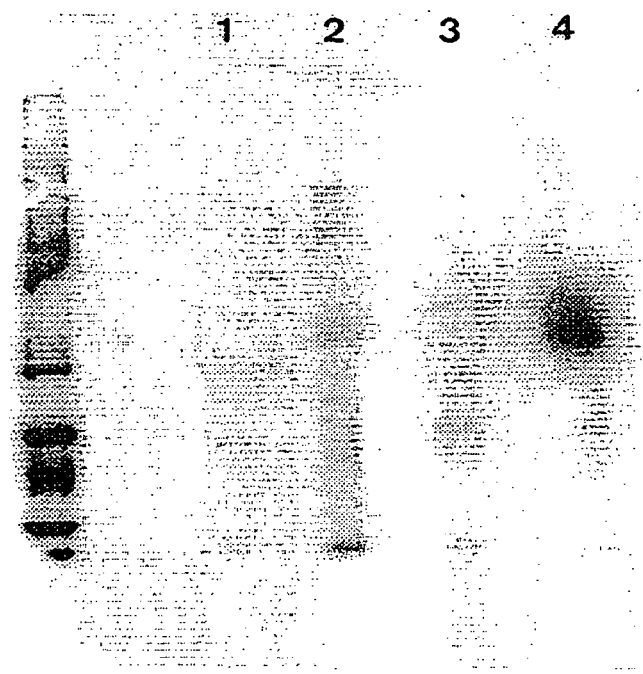
FIG. 16. Upregulation of α10 integrin subunit in chondrocytes cultured in alginate.

Upregulation of α10 Integrin Subunit in Chondrocytes Cultured in Alginate Beads
Material and Methods Human chondrocytes cultured in monolayer for 2 weeks were detached with trypsin-EDTA and introduced into alginate beads. Chondrocytes cultured in alginate are known to preserve their phenotype while chondrocytes cultured in monolayer are dedifferentiated. After 11 days chondrocytes cultured either in alginate or on monolayer were isolated and surface labelled with $^{125}$I. The α10 integrin subunit was then immunoprecipitated with polyclonal antibodies recognising the cytoplasmic domain of α10 (see Example 6 and Camper et al, JBC, 273, 20383-20389 (1998))
Results As shown in FIG. 16 chondrocytes cultured in alginate beads (lanes 3 and 4) upregulated their protein expression of α10β1. This was in contrast to chondrocytes cultured in monolayer (lanes 1 and 2) which had a very low expression of α10β1. Immunoprecipitation with ab control antibody is shown in lanes 1 and 3. It is known that chondrocytes preserve their cartilage specific matrixproduction in alginate cultures but not in monolayer culture which point to that alginate preserve the phenotype of chondrocytes. These results support that α10 integrin subunit can be used as a marker for differentiated chondrocytes.

Example 17

Figure 17:
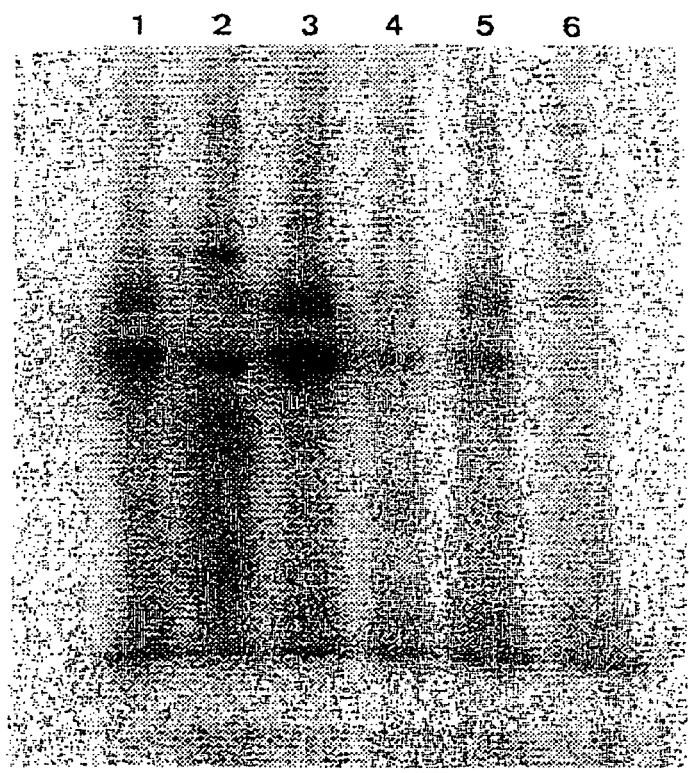
FIG. 17. Immunoprecipitation of the α10 integrin subunit from human smooth muscle cells.

Immunoprecipitation of the α10 Integrin Subunit from Human Smooth Muscle Cells.
Material and Methods Human smooth muscle cells were isolated from human aorta. After one week in culture the cells were $^{125}$I-labelled, lysed and immunoprecipitated with antibodies against the integrin subunit β1 (lane 1), α1 (lane 2), α2 (lane 3), α10 (lane 4), α3 (lane 5), control (lane 6) (FIG. 17). The experiment was done as described in Example 7.
Results The α10 antibody precipitated two bands from the smooth muscle cells corresponding to the α10 and the β1 integrin subunit (FIG. 17).

Example 18

Construction of Bacterial Expression Vector Containing Sequence for α10 Splice Region.

A plasmid for intracellular expression in *E. coli* of the alternatively spliced region (amino acid pos. 974-1008, SEQ ID No. 4) was constructed as described. The alternatively spliced region were back-translated using the *E. coli* high frequency codon table, creating a cDNA sequence of 96% identity with the original sequence (SEQ ID No. 1, nucleotide pos 2940-3044). Using sequence overlap extension (Horton et al., Biotechniques 8:528, 1990) primer α10pfor (tab. I) and α10pfor (tab. I) was used to generate a double stranded fragment encoding the α10 amino acid sequence. This fragment was used as a PCR template with primers α10pfor2 (tab. I) and α10prev2 (tab. I) in order to generate restriction enzyme site for sub-cloning in a pET vector containing the Z-domain of staphylococcal protein A, creating a fusion of the α10 spliced region with the amino terminal of the Z-domain with thrombin cleavage site residing in-between. The fragment generated in the second PCR reaction is shown (SEQ ID No. 3; amino acid sequence disclosed as SEQ ID No: 6) also indicating the unique restriction enzymes used for sub-cloning in the expression vector.

TABLE I (SEQ ID Nos: 18-21, respectively, in order of appearance)

| | |
|---|---|
| α10pfor (SEQ ID No: 18) | 5'-GTTCAGAACCTGGGTTGCTACGTTG TTTCCGGTCTGATCATCTCCGCTCTGCT GCCGGCTGT-3' |
| α10pfor2 (SEQ ID No: 19) | 5'-GGGGCATATGGTTCAGAACCTGGGT TGCTACGTTG-3' |
| α10prev (SEQ ID No: 20) | 5'-GATAACCTGGGACAAGCTTAGGAAG TAGTTACCACCGTGAGCAACAGCCGGCA GCAGAGCGGA-3' |
| α10prev2 (SEQ ID No: 21) | 5'-GGGGGGATCCGCGCGGCACCAGGCC GCTGATAACCTGGGACAAGCTTAGGAAG T-3' |

The invention claimed is:

1. A purified recombinant cDNA comprising the sequence of SEQ ID NO:1.
2. A recombinant nucleic acid vector comprising the cDNA of claim 1.
3. The vector of claim 2, which comprises a plasmid.
4. A recombinant cell comprising the plasmid of claim 3.
5. A recombinant cell comprising the vector of claim 2.
6. A recombinant cell comprising the cDNA of claim 1.
7. A purified recombinant cDNA comprising the sequence of SEQ ID NO:2.
8. A recombinant nucleic acid vector comprising the cDNA of claim 7.
9. The vector of claim 8, which comprises a plasmid.
10. A recombinant cell comprising the plasmid of claim 9.
11. A recombinant cell comprising the vector of claim 8.
12. A recombinant cell comprising the cDNA of claim 7.

* * * * *

SEQUENCE LISTING

<160> NUMBER OF SEQ ID NOS: 299

<210> SEQ ID NO 1
<211> LENGTH: 3884
<212> TYPE: DNA
<213> ORGANISM: Homo sapiens
<220> FEATURE:
<221> NAME/KEY: CDS
<222> LOCATION: (22)..(3522)

<400> SEQUENCE: 1

```
caggtcagaa accgatcagg c atg gaa ctc ccc ttc gtc act cac ctg ttc        51
                         Met Glu Leu Pro Phe Val Thr His Leu Phe
                         1               5                   10 ttg ccc ctg gtg ttc ctg aca ggt ctc tgc tcc ccc ttt aac ctg gat        99
Leu Pro Leu Val Phe Leu Thr Gly Leu Cys Ser Pro Phe Asn Leu Asp
                 15                  20                  25 gaa cat cac cca cgc cta ttc cca ggg cca cca gaa gct gaa ttt gga       147
Glu His His Pro Arg Leu Phe Pro Gly Pro Pro Glu Ala Glu Phe Gly
             30                  35                  40 tac agt gtc tta caa cat gtt ggg ggt gga cag cga tgg atg ctg gtg       195
Tyr Ser Val Leu Gln His Val Gly Gly Gly Gln Arg Trp Met Leu Val
         45                  50                  55 ggc gcc ccc tgg gat ggg cct tca ggc gac cgg agg ggg gac gtt tat       243
Gly Ala Pro Trp Asp Gly Pro Ser Gly Asp Arg Arg Gly Asp Val Tyr
     60                  65                  70 cgc tgc cct gta ggg ggg gcc cac aat gcc cca tgt gcc aag ggc cac       291
Arg Cys Pro Val Gly Gly Ala His Asn Ala Pro Cys Ala Lys Gly His
 75                  80                  85                  90 tta ggt gac tac caa ctg gga aat tca tct cat cct gct gtg aat atg       339
Leu Gly Asp Tyr Gln Leu Gly Asn Ser Ser His Pro Ala Val Asn Met
                 95                 100                 105 cac ctg ggg atg tct ctg tta gag aca gat ggt gat ggg gga ttc atg       387
His Leu Gly Met Ser Leu Leu Glu Thr Asp Gly Asp Gly Gly Phe Met
            110                 115                 120 gcc tgt gcc cct ctc tgg tct cgt gct tgt ggc agc tct gtc ttc agt       435
Ala Cys Ala Pro Leu Trp Ser Arg Ala Cys Gly Ser Ser Val Phe Ser
        125                 130                 135 tct ggg ata tgt gcc cgt gtg gat gct tca ttc cag cct cag gga agc       483
Ser Gly Ile Cys Ala Arg Val Asp Ala Ser Phe Gln Pro Gln Gly Ser
    140                 145                 150 ctg gca ccc act gcc caa cgc tgc cca aca tac atg gat gtt gtc att       531
Leu Ala Pro Thr Ala Gln Arg Cys Pro Thr Tyr Met Asp Val Val Ile
155                 160                 165                 170 gtc ttg gat ggc tcc aac agc atc tac ccc tgg tct gaa gtt cag acc       579
Val Leu Asp Gly Ser Asn Ser Ile Tyr Pro Trp Ser Glu Val Gln Thr
                175                 180                 185
```

-continued

| | |
|---|---|
| ttc cta cga aga ctg gta ggg aaa ctg ttt att gac cca gaa cag ata<br>Phe Leu Arg Arg Leu Val Gly Lys Leu Phe Ile Asp Pro Glu Gln Ile<br>190           195               200 | 627 |
| cag gtg gga ctg gta cag tat ggg gag agc cct gta cat gag tgg tcc<br>Gln Val Gly Leu Val Gln Tyr Gly Glu Ser Pro Val His Glu Trp Ser<br>    205               210               215 | 675 |
| ctg gga gat ttc cga acg aag gaa gaa gtg gtg aga gca gca aag aac<br>Leu Gly Asp Phe Arg Thr Lys Glu Glu Val Val Arg Ala Ala Lys Asn<br>220           225               230 | 723 |
| ctc agt cgg cgg gag gga cga gaa aca aag act gcc caa gca ata atg<br>Leu Ser Arg Arg Glu Gly Arg Glu Thr Lys Thr Ala Gln Ala Ile Met<br>235           240               245               250 | 771 |
| gtg gcc tgc aca gaa ggg ttc agt cag tcc cat ggg ggc cga ccc gag<br>Val Ala Cys Thr Glu Gly Phe Ser Gln Ser His Gly Gly Arg Pro Glu<br>        255               260               265 | 819 |
| gct gcc agg cta ctg gtg gtt gtc act gat gga gag tcc cat gat gga<br>Ala Ala Arg Leu Leu Val Val Val Thr Asp Gly Glu Ser His Asp Gly<br>    270               275               280 | 867 |
| gag gag ctt cct gca gca cta aag gcc tgt gag gct gga aga gtg aca<br>Glu Glu Leu Pro Ala Ala Leu Lys Ala Cys Glu Ala Gly Arg Val Thr<br>285               290               295 | 915 |
| cgc tat ggg att gca gtc ctt ggt cac tac ctc cgg cgg cag cga gat<br>Arg Tyr Gly Ile Ala Val Leu Gly His Tyr Leu Arg Arg Gln Arg Asp<br>300               305               310 | 963 |
| ccc agc tct ttc ctg aga gaa att aga act att gcc agt gat cca gat<br>Pro Ser Ser Phe Leu Arg Glu Ile Arg Thr Ile Ala Ser Asp Pro Asp<br>315               320               325               330 | 1011 |
| gag cga ttc ttc ttc aat gtc aca gat gag gct gct ctg act gac att<br>Glu Arg Phe Phe Phe Asn Val Thr Asp Glu Ala Ala Leu Thr Asp Ile<br>        335               340               345 | 1059 |
| gtg gat gca cta gga gat cgg att ttt ggc ctt gaa ggg tcc cat gca<br>Val Asp Ala Leu Gly Asp Arg Ile Phe Gly Leu Glu Gly Ser His Ala<br>    350               355               360 | 1107 |
| gaa aac gaa agc tcc ttt ggg ctg gaa atg tct cag att ggt ttc tcc<br>Glu Asn Glu Ser Ser Phe Gly Leu Glu Met Ser Gln Ile Gly Phe Ser<br>365               370               375 | 1155 |
| act cat cgg cta aag gat ggg att ctt ttt ggg atg gtg ggg gcc tat<br>Thr His Arg Leu Lys Asp Gly Ile Leu Phe Gly Met Val Gly Ala Tyr<br>380               385               390 | 1203 |
| gac tgg gga ggc tct gtg cta tgg ctt gaa gga ggc cac cgc ctt ttc<br>Asp Trp Gly Gly Ser Val Leu Trp Leu Glu Gly Gly His Arg Leu Phe<br>395               400               405               410 | 1251 |
| ccc cca cga atg gca ctg gaa gac gag ttc ccc cct gca ctg cag aac<br>Pro Pro Arg Met Ala Leu Glu Asp Glu Phe Pro Pro Ala Leu Gln Asn<br>        415               420               425 | 1299 |
| cat gca gcc tac ctg ggt tac tct gtt tct tcc atg ctt ttg cgg ggt<br>His Ala Ala Tyr Leu Gly Tyr Ser Val Ser Ser Met Leu Leu Arg Gly<br>    430               435               440 | 1347 |
| gga cgc cgc ctg ttt ctc tct ggg gct cct cga ttt aga cat cga gga<br>Gly Arg Arg Leu Phe Leu Ser Gly Ala Pro Arg Phe Arg His Arg Gly<br>445               450               455 | 1395 |
| aaa gtc atc gcc ttc cag ctt aag aaa gat ggg gct gtg agg gtt gcc<br>Lys Val Ile Ala Phe Gln Leu Lys Lys Asp Gly Ala Val Arg Val Ala<br>460               465               470 | 1443 |
| cag agc ctc cag ggg gag cag att ggt tca tac ttt ggc agt gag ctc<br>Gln Ser Leu Gln Gly Glu Gln Ile Gly Ser Tyr Phe Gly Ser Glu Leu<br>475               480               485               490 | 1491 |
| tgc cca ttg gat aca gat agg gat gga aca act gat gtc tta ctt gtg<br>Cys Pro Leu Asp Thr Asp Arg Asp Gly Thr Thr Asp Val Leu Leu Val<br>        495               500               505 | 1539 |

```
gct gcc ccc atg ttc ctg gga ccc cag aac aag gaa aca gga cgt gtt    1587
Ala Ala Pro Met Phe Leu Gly Pro Gln Asn Lys Glu Thr Gly Arg Val
        510                 515                 520 tat gtg tat ctg gta ggc cag cag tcc ttg ctg acc ctc caa gga aca    1635
Tyr Val Tyr Leu Val Gly Gln Gln Ser Leu Leu Thr Leu Gln Gly Thr
525                 530                 535 ctt cag cca gaa ccc ccc cag gat gct cgg ttt ggc ttt gcc atg gga    1683
Leu Gln Pro Glu Pro Pro Gln Asp Ala Arg Phe Gly Phe Ala Met Gly
            540                 545                 550 gct ctt cct gat ctg aac caa gat ggt ttt gct gat gtg gct gtg ggg    1731
Ala Leu Pro Asp Leu Asn Gln Asp Gly Phe Ala Asp Val Ala Val Gly
555                 560                 565                 570 gcg cct ctg gaa gat ggg cac cag gga gca ctg tac ctg tac cat gga    1779
Ala Pro Leu Glu Asp Gly His Gln Gly Ala Leu Tyr Leu Tyr His Gly
                575                 580                 585 acc cag agt gga gtc agg ccc cat cct gcc cag agg att gct gct gcc    1827
Thr Gln Ser Gly Val Arg Pro His Pro Ala Gln Arg Ile Ala Ala Ala
            590                 595                 600 tcc atg cca cat gcc ctc agc tac ttt ggc cga agt gtg gat ggt cgg    1875
Ser Met Pro His Ala Leu Ser Tyr Phe Gly Arg Ser Val Asp Gly Arg
        605                 610                 615 cta gat ctg gat gga gat gat ctg gtc gat gtg gct gtg ggt gcc cag    1923
Leu Asp Leu Asp Gly Asp Asp Leu Val Asp Val Ala Val Gly Ala Gln
620                 625                 630 ggg gca gcc atc ctg ctc agc tcc cgg ccc att gtc cat ctg acc cca    1971
Gly Ala Ala Ile Leu Leu Ser Ser Arg Pro Ile Val His Leu Thr Pro
635                 640                 645                 650 tca ctg gag gtg acc cca cag gcc atc agt gtg gtt cag agg gac tgt    2019
Ser Leu Glu Val Thr Pro Gln Ala Ile Ser Val Val Gln Arg Asp Cys
                655                 660                 665 agg cgg cga ggc caa gaa gca gtc tgt ctg act gca gcc ctt tgc ttc    2067
Arg Arg Arg Gly Gln Glu Ala Val Cys Leu Thr Ala Ala Leu Cys Phe
            670                 675                 680 caa gtg acc tcc cgt act cct ggt cgc tgg gat cac caa ttc tac atg    2115
Gln Val Thr Ser Arg Thr Pro Gly Arg Trp Asp His Gln Phe Tyr Met
        685                 690                 695 agg ttc acc gca tca ctg gat gaa tgg act gct ggg gca cgt gca gca    2163
Arg Phe Thr Ala Ser Leu Asp Glu Trp Thr Ala Gly Ala Arg Ala Ala
700                 705                 710 ttt gat ggc tct ggc cag agg ttg tcc cct cgg agg ctc cgg ctc agt    2211
Phe Asp Gly Ser Gly Gln Arg Leu Ser Pro Arg Arg Leu Arg Leu Ser
715                 720                 725                 730 gtg ggg aat gtc act tgt gag cag cta cac ttc cat gtg ctg gat aca    2259
Val Gly Asn Val Thr Cys Glu Gln Leu His Phe His Val Leu Asp Thr
                735                 740                 745 tca gat tac ctc cgg cca gtg gcc ttg act gtg acc ttt gcc ttg gac    2307
Ser Asp Tyr Leu Arg Pro Val Ala Leu Thr Val Thr Phe Ala Leu Asp
            750                 755                 760 aat act aca aag cca ggg cct gtg ctg aat gag ggc tca ccc acc tct    2355
Asn Thr Thr Lys Pro Gly Pro Val Leu Asn Glu Gly Ser Pro Thr Ser
        765                 770                 775 ata caa aag ctg gtc ccc ttc tca aag gat tgt ggc cct gac aat gaa    2403
Ile Gln Lys Leu Val Pro Phe Ser Lys Asp Cys Gly Pro Asp Asn Glu
780                 785                 790 tgt gtc aca gac ctg gtg ctt caa gtg aat atg gac atc aga ggc tcc    2451
Cys Val Thr Asp Leu Val Leu Gln Val Asn Met Asp Ile Arg Gly Ser
795                 800                 805                 810 agg aag gcc cca ttt gtg gtt cga ggt ggc cgg cgg aaa gtg ctg gta    2499
Arg Lys Ala Pro Phe Val Val Arg Gly Gly Arg Arg Lys Val Leu Val
```

-continued

|  |  |  |  |  |  |  |  | 815 |  |  |  | 820 |  |  |  | 825 |  |  |
|---|---|---|---|---|---|---|---|---|---|---|---|---|---|---|---|---|---|---|

```
tct aca act ctg gag aac aga aag gaa aat gct tac aat acg agc ctg      2547
Ser Thr Thr Leu Glu Asn Arg Lys Glu Asn Ala Tyr Asn Thr Ser Leu
            830                 835                 840 agt atc atc ttc tct aga aac ctc cac ctg gcc agt ctc act cct cag      2595
Ser Ile Ile Phe Ser Arg Asn Leu His Leu Ala Ser Leu Thr Pro Gln
        845                 850                 855 aga gag agc cca ata aag gtg gaa tgt gcc gcc cct tct gct cat gcc      2643
Arg Glu Ser Pro Ile Lys Val Glu Cys Ala Ala Pro Ser Ala His Ala
    860                 865                 870 cgg ctc tgc agt gtg ggg cat cct gtc ttc cag act gga gcc aag gtg      2691
Arg Leu Cys Ser Val Gly His Pro Val Phe Gln Thr Gly Ala Lys Val
875                 880                 885                 890 acc ttt ctg cta gag ttt gag ttt agc tgc tcc tct ctc ctg agc cag      2739
Thr Phe Leu Leu Glu Phe Glu Phe Ser Cys Ser Ser Leu Leu Ser Gln
                895                 900                 905 gtc ttt ggg aag ctg act gcc agc agt gac agc ctg gag aga aat ggc      2787
Val Phe Gly Lys Leu Thr Ala Ser Ser Asp Ser Leu Glu Arg Asn Gly
            910                 915                 920 acc ctt caa gaa aac aca gcc cag acc tca gcc tac atc caa tat gag      2835
Thr Leu Gln Glu Asn Thr Ala Gln Thr Ser Ala Tyr Ile Gln Tyr Glu
        925                 930                 935 ccc cac ctc ctg ttc tct agt gag tct acc ctg cac cgc tat gag gtt      2883
Pro His Leu Leu Phe Ser Ser Glu Ser Thr Leu His Arg Tyr Glu Val
    940                 945                 950 cac cca tat ggg acc ctc cca gtg ggt cct ggc cca gaa ttc aaa acc      2931
His Pro Tyr Gly Thr Leu Pro Val Gly Pro Gly Pro Glu Phe Lys Thr
955                 960                 965                 970 act ctc agg gtt cag aac cta ggc tgc tat gtg gtc agt ggc ctc atc      2979
Thr Leu Arg Val Gln Asn Leu Gly Cys Tyr Val Val Ser Gly Leu Ile
                975                 980                 985 atc tca gcc ctc ctt cca gct gtg gcc cat ggg ggc aat tac ttc cta      3027
Ile Ser Ala Leu Leu Pro Ala Val Ala His Gly Gly Asn Tyr Phe Leu
            990                 995                 1000 tca ctg tct caa gtc atc act aac aat gca agc tgc ata gtg cag aac      3075
Ser Leu Ser Gln Val Ile Thr Asn Asn Ala Ser Cys Ile Val Gln Asn
        1005                1010                1015 ctg act gaa ccc cca ggc cca cct gtg cat cca gag gag ctt caa cac      3123
Leu Thr Glu Pro Pro Gly Pro Pro Val His Pro Glu Glu Leu Gln His
    1020                1025                1030 aca aac aga ctg aat ggg agc aat act cag tgt cag gtg gtg agg tgc      3171
Thr Asn Arg Leu Asn Gly Ser Asn Thr Gln Cys Gln Val Val Arg Cys
1035                1040                1045                1050 cac ctt ggg cag ctg gca aag ggg act gag gtc tct gtt gga cta ttg      3219
His Leu Gly Gln Leu Ala Lys Gly Thr Glu Val Ser Val Gly Leu Leu
                1055                1060                1065 agg ctg gtt cac aat gaa ttt ttc cga aga gcc aag ttc aag tcc ctg      3267
Arg Leu Val His Asn Glu Phe Phe Arg Arg Ala Lys Phe Lys Ser Leu
            1070                1075                1080 acg gtg gtc agc acc ttt gag ctg gga acc gaa gag ggc agt gtc cta      3315
Thr Val Val Ser Thr Phe Glu Leu Gly Thr Glu Glu Gly Ser Val Leu
        1085                1090                1095 cag ctg act gaa gcc tcc cgt tgg agt gag agc ctc ttg gag gtg gtt      3363
Gln Leu Thr Glu Ala Ser Arg Trp Ser Glu Ser Leu Leu Glu Val Val
    1100                1105                1110 cag acc cgg cct atc ctc atc tcc ctg tgg atc ctc ata ggc agt gtc      3411
Gln Thr Arg Pro Ile Leu Ile Ser Leu Trp Ile Leu Ile Gly Ser Val
1115                1120                1125                1130 ctg gga ggg ttg ctc ctg ctt gct ctc ctt gtc ttc tgc ctg tgg aag      3459
```

```
Leu Gly Gly Leu Leu Leu Leu Ala Leu Leu Val Phe Cys Leu Trp Lys
            1135                1140                1145 ctt ggc ttc ttt gcc cat aag aaa atc cct gag gaa gaa aaa aga gaa      3507
Leu Gly Phe Phe Ala His Lys Lys Ile Pro Glu Glu Glu Lys Arg Glu
        1150                1155                1160 gag aag ttg gag caa tgaatgtaga ataagggtct agaaagtcct ccctggcagc      3562
Glu Lys Leu Glu Gln
        1165 tttcttcaag agacttgcat aaaagcagag gtttgggggc tcagatggga caagaagccg    3622 cctctggact atctccccag accagcagcc tgacttgact tttgagtcct agggatgctg    3682 ctggctagag atgaggcttt acctcagaca agaagagctg gcaccaaaac tagccatgct    3742 cccaccctct gcttccctcc tcctcgtgat cctggttcca tagccaacac tggggctttt    3802 gtttggggtc cttttatccc caggaatcaa taattttttt gcctaggaaa aaaaaaagcg    3862 gccgcgaatt cgatatcaag ct                                             3884

<210> SEQ ID NO 2
<211> LENGTH: 3779
<212> TYPE: DNA
<213> ORGANISM: Homo sapiens
<220> FEATURE:
<221> NAME/KEY: CDS
<222> LOCATION: (22)..(3417)

<400> SEQUENCE: 2
caggtcagaa accgatcagg c atg gaa ctc ccc ttc gtc act cac ctg ttc      51
                        Met Glu Leu Pro Phe Val Thr His Leu Phe
                         1               5                  10 ttg ccc ctg gtg ttc ctg aca ggt ctc tgc tcc ccc ttt aac ctg gat      99
Leu Pro Leu Val Phe Leu Thr Gly Leu Cys Ser Pro Phe Asn Leu Asp
            15                  20                  25 gaa cat cac cca cgc cta ttc cca ggg cca cca gaa gct gaa ttt gga      147
Glu His His Pro Arg Leu Phe Pro Gly Pro Pro Glu Ala Glu Phe Gly
        30                  35                  40 tac agt gtc tta caa cat gtt ggg ggt gga cag cga tgg atg ctg gtg      195
Tyr Ser Val Leu Gln His Val Gly Gly Gly Gln Arg Trp Met Leu Val
    45                  50                  55 ggc gcc ccc tgg gat ggg cct tca ggc gac cgg agg ggg gac gtt tat      243
Gly Ala Pro Trp Asp Gly Pro Ser Gly Asp Arg Arg Gly Asp Val Tyr
60                  65                  70 cgc tgc cct gta ggg ggg gcc cac aat gcc cca tgt gcc aag ggc cac      291
Arg Cys Pro Val Gly Gly Ala His Asn Ala Pro Cys Ala Lys Gly His
75                  80                  85                  90 tta ggt gac tac caa ctg gga aat tca tct cat cct gct gtg aat atg      339
Leu Gly Asp Tyr Gln Leu Gly Asn Ser Ser His Pro Ala Val Asn Met
            95                  100                 105 cac ctg ggg atg tct ctg tta gag aca gat ggt gat ggg gga ttc atg      387
His Leu Gly Met Ser Leu Leu Glu Thr Asp Gly Asp Gly Gly Phe Met
        110                 115                 120 gcc tgt gcc cct ctc tgg tct cgt gct tgt ggc agc tct gtc ttc agt      435
Ala Cys Ala Pro Leu Trp Ser Arg Ala Cys Gly Ser Ser Val Phe Ser
    125                 130                 135 tct ggg ata tgt gcc cgt gtg gat gct tca ttc cag cct cag gga agc      483
Ser Gly Ile Cys Ala Arg Val Asp Ala Ser Phe Gln Pro Gln Gly Ser
140                 145                 150 ctg gca ccc act gcc caa cgc tgc cca aca tac atg gat gtt gtc att      531
Leu Ala Pro Thr Ala Gln Arg Cys Pro Thr Tyr Met Asp Val Val Ile
155                 160                 165                 170 gtc ttg gat ggc tcc aac agc atc tac ccc tgg tct gaa gtt cag acc      579
```

```
                Val Leu Asp Gly Ser Asn Ser Ile Tyr Pro Trp Ser Glu Val Gln Thr
                                175                 180                 185 ttc cta cga aga ctg gta ggg aaa ctg ttt att gac cca gaa cag ata           627
Phe Leu Arg Arg Leu Val Gly Lys Leu Phe Ile Asp Pro Glu Gln Ile
                190                 195                 200 cag gtg gga ctg gta cag tat ggg gag agc cct gta cat gag tgg tcc           675
Gln Val Gly Leu Val Gln Tyr Gly Glu Ser Pro Val His Glu Trp Ser
                205                 210                 215 ctg gga gat ttc cga acg aag gaa gaa gtg gtg aga gca gca aag aac           723
Leu Gly Asp Phe Arg Thr Lys Glu Glu Val Val Arg Ala Ala Lys Asn
        220                 225                 230 ctc agt cgg cgg gag gga cga gaa aca aag act gcc caa gca ata atg           771
Leu Ser Arg Arg Glu Gly Arg Glu Thr Lys Thr Ala Gln Ala Ile Met
235                 240                 245                 250 gtg gcc tgc aca gaa ggg ttc agt cag tcc cat ggg ggc cga ccc gag           819
Val Ala Cys Thr Glu Gly Phe Ser Gln Ser His Gly Gly Arg Pro Glu
                    255                 260                 265 gct gcc agg cta ctg gtg gtt gtc act gat gga gag tcc cat gat gga           867
Ala Ala Arg Leu Leu Val Val Val Thr Asp Gly Glu Ser His Asp Gly
                270                 275                 280 gag gag ctt cct gca gca cta aag gcc tgt gag gct gga aga gtg aca           915
Glu Glu Leu Pro Ala Ala Leu Lys Ala Cys Glu Ala Gly Arg Val Thr
            285                 290                 295 cgc tat ggg att gca gtc ctt ggt cac tac ctc cgg cgg cag cga gat           963
Arg Tyr Gly Ile Ala Val Leu Gly His Tyr Leu Arg Arg Gln Arg Asp
        300                 305                 310 ccc agc tct ttc ctg aga gaa att aga act att gcc agt gat cca gat          1011
Pro Ser Ser Phe Leu Arg Glu Ile Arg Thr Ile Ala Ser Asp Pro Asp
315                 320                 325                 330 gag cga ttc ttc ttc aat gtc aca gat gag gct gct ctg act gac att          1059
Glu Arg Phe Phe Phe Asn Val Thr Asp Glu Ala Ala Leu Thr Asp Ile
                    335                 340                 345 gtg gat gca cta gga gat cgg att ttt ggc ctt gaa ggg tcc cat gca          1107
Val Asp Ala Leu Gly Asp Arg Ile Phe Gly Leu Glu Gly Ser His Ala
                350                 355                 360 gaa aac gaa agc tcc ttt ggg ctg gaa atg tct cag att ggt ttc tcc          1155
Glu Asn Glu Ser Ser Phe Gly Leu Glu Met Ser Gln Ile Gly Phe Ser
            365                 370                 375 act cat cgg cta aag gat ggg att ctt ttt ggg atg gtg ggg gcc tat          1203
Thr His Arg Leu Lys Asp Gly Ile Leu Phe Gly Met Val Gly Ala Tyr
        380                 385                 390 gac tgg gga ggc tct gtg cta tgg ctt gaa gga ggc cac cgc ctt ttc          1251
Asp Trp Gly Gly Ser Val Leu Trp Leu Glu Gly Gly His Arg Leu Phe
395                 400                 405                 410 ccc cca cga atg gca ctg gaa gac gag ttc ccc cct gca ctg cag aac          1299
Pro Pro Arg Met Ala Leu Glu Asp Glu Phe Pro Pro Ala Leu Gln Asn
                    415                 420                 425 cat gca gcc tac ctg ggt tac tct gtt tct tcc atg ctt ttg cgg ggt          1347
His Ala Ala Tyr Leu Gly Tyr Ser Val Ser Ser Met Leu Leu Arg Gly
                430                 435                 440 gga cgc cgc ctg ttt ctc tct ggg gct cct cga ttt aga cat cga gga          1395
Gly Arg Arg Leu Phe Leu Ser Gly Ala Pro Arg Phe Arg His Arg Gly
            445                 450                 455 aaa gtc atc gcc ttc cag ctt aag aaa gat ggg gct gtg agg gtt gcc          1443
Lys Val Ile Ala Phe Gln Leu Lys Lys Asp Gly Ala Val Arg Val Ala
        460                 465                 470 cag agc ctc cag ggg gag cag att ggt tca tac ttt ggc agt gag ctc          1491
Gln Ser Leu Gln Gly Glu Gln Ile Gly Ser Tyr Phe Gly Ser Glu Leu
475                 480                 485                 490
```

-continued

| | | |
|---|---|---|
| tgc cca ttg gat aca gat agg gat gga aca act gat gtc tta ctt gtg<br>Cys Pro Leu Asp Thr Asp Arg Asp Gly Thr Thr Asp Val Leu Leu Val<br>495 500 505 | 1539 |
| gct gcc ccc atg ttc ctg gga ccc cag aac aag gaa aca gga cgt gtt<br>Ala Ala Pro Met Phe Leu Gly Pro Gln Asn Lys Glu Thr Gly Arg Val<br>510 515 520 | 1587 |
| tat gtg tat ctg gta ggc cag cag tcc ttg ctg acc ctc caa gga aca<br>Tyr Val Tyr Leu Val Gly Gln Gln Ser Leu Leu Thr Leu Gln Gly Thr<br>525 530 535 | 1635 |
| ctt cag cca gaa ccc ccc cag gat gct cgg ttt ggc ttt gcc atg gga<br>Leu Gln Pro Glu Pro Pro Gln Asp Ala Arg Phe Gly Phe Ala Met Gly<br>540 545 550 | 1683 |
| gct ctt cct gat ctg aac caa gat ggt ttt gct gat gtg gct gtg ggg<br>Ala Leu Pro Asp Leu Asn Gln Asp Gly Phe Ala Asp Val Ala Val Gly<br>555 560 565 570 | 1731 |
| gcg cct ctg gaa gat ggg cac cag gga gca ctg tac ctg tac cat gga<br>Ala Pro Leu Glu Asp Gly His Gln Gly Ala Leu Tyr Leu Tyr His Gly<br>575 580 585 | 1779 |
| acc cag agt gga gtc agg ccc cat cct gcc cag agg att gct gct gcc<br>Thr Gln Ser Gly Val Arg Pro His Pro Ala Gln Arg Ile Ala Ala Ala<br>590 595 600 | 1827 |
| tcc atg cca cat gcc ctc agc tac ttt ggc cga agt gtg gat ggt cgg<br>Ser Met Pro His Ala Leu Ser Tyr Phe Gly Arg Ser Val Asp Gly Arg<br>605 610 615 | 1875 |
| cta gat ctg gat gga gat gat ctg gtc gat gtg gct gtg ggt gcc cag<br>Leu Asp Leu Asp Gly Asp Asp Leu Val Asp Val Ala Val Gly Ala Gln<br>620 625 630 | 1923 |
| ggg gca gcc atc ctg ctc agc tcc cgg ccc att gtc cat ctg acc cca<br>Gly Ala Ala Ile Leu Leu Ser Ser Arg Pro Ile Val His Leu Thr Pro<br>635 640 645 650 | 1971 |
| tca ctg gag gtg acc cca cag gcc atc agt gtg gtt cag agg gac tgt<br>Ser Leu Glu Val Thr Pro Gln Ala Ile Ser Val Val Gln Arg Asp Cys<br>655 660 665 | 2019 |
| agg cgg cga ggc caa gaa gca gtc tgt ctg act gca gcc ctt tgc ttc<br>Arg Arg Arg Gly Gln Glu Ala Val Cys Leu Thr Ala Ala Leu Cys Phe<br>670 675 680 | 2067 |
| caa gtg acc tcc cgt act cct ggt cgc tgg gat cac caa ttc tac atg<br>Gln Val Thr Ser Arg Thr Pro Gly Arg Trp Asp His Gln Phe Tyr Met<br>685 690 695 | 2115 |
| agg ttc acc gca tca ctg gat gaa tgg act gct ggg gca cgt gca gca<br>Arg Phe Thr Ala Ser Leu Asp Glu Trp Thr Ala Gly Ala Arg Ala Ala<br>700 705 710 | 2163 |
| ttt gat ggc tct ggc cag agg ttg tcc cct cgg agg ctc cgg ctc agt<br>Phe Asp Gly Ser Gly Gln Arg Leu Ser Pro Arg Arg Leu Arg Leu Ser<br>715 720 725 730 | 2211 |
| gtg ggg aat gtc act tgt gag cag cta cac ttc cat gtg ctg gat aca<br>Val Gly Asn Val Thr Cys Glu Gln Leu His Phe His Val Leu Asp Thr<br>735 740 745 | 2259 |
| tca gat tac ctc cgg cca gtg gcc ttg act gtg acc ttt gcc ttg gac<br>Ser Asp Tyr Leu Arg Pro Val Ala Leu Thr Val Thr Phe Ala Leu Asp<br>750 755 760 | 2307 |
| aat act aca aag cca ggg cct gtg ctg aat gag ggc tca ccc acc tct<br>Asn Thr Thr Lys Pro Gly Pro Val Leu Asn Glu Gly Ser Pro Thr Ser<br>765 770 775 | 2355 |
| ata caa aag ctg gtc ccc ttc tca aag gat tgt ggc cct gac aat gaa<br>Ile Gln Lys Leu Val Pro Phe Ser Lys Asp Cys Gly Pro Asp Asn Glu<br>780 785 790 | 2403 |
| tgt gtc aca gac ctg gtg ctt caa gtg aat atg gac atc aga ggc tcc<br>Cys Val Thr Asp Leu Val Leu Gln Val Asn Met Asp Ile Arg Gly Ser<br>795 800 805 810 | 2451 |

-continued

| | |
|---|---|
| agg aag gcc cca ttt gtg gtt cga ggt ggc cgg cgg aaa gtg ctg gta<br>Arg Lys Ala Pro Phe Val Val Arg Gly Gly Arg Arg Lys Val Leu Val<br>             815                              820                     825 | 2499 |
| tct aca act ctg gag aac aga aag gaa aat gct tac aat acg agc ctg<br>Ser Thr Thr Leu Glu Asn Arg Lys Glu Asn Ala Tyr Asn Thr Ser Leu<br>             830                              835                     840 | 2547 |
| agt atc atc ttc tct aga aac ctc cac ctg gcc agt ctc act cct cag<br>Ser Ile Ile Phe Ser Arg Asn Leu His Leu Ala Ser Leu Thr Pro Gln<br>             845                              850                     855 | 2595 |
| aga gag agc cca ata aag gtg gaa tgt gcc gcc cct tct gct cat gcc<br>Arg Glu Ser Pro Ile Lys Val Glu Cys Ala Ala Pro Ser Ala His Ala<br>860                              865                            870 | 2643 |
| cgg ctc tgc agt gtg ggg cat cct gtc ttc cag act gga gcc aag gtg<br>Arg Leu Cys Ser Val Gly His Pro Val Phe Gln Thr Gly Ala Lys Val<br>875                            880                            885                     890 | 2691 |
| acc ttt ctg cta gag ttt gag ttt agc tgc tcc tct ctc ctg agc cag<br>Thr Phe Leu Leu Glu Phe Glu Phe Ser Cys Ser Ser Leu Leu Ser Gln<br>             895                              900                     905 | 2739 |
| gtc ttt ggg aag ctg act gcc agc agt gac agc ctg gag aga aat ggc<br>Val Phe Gly Lys Leu Thr Ala Ser Ser Asp Ser Leu Glu Arg Asn Gly<br>             910                              915                     920 | 2787 |
| acc ctt caa gaa aac aca gcc cag acc tca gcc tac atc caa tat gag<br>Thr Leu Gln Glu Asn Thr Ala Gln Thr Ser Ala Tyr Ile Gln Tyr Glu<br>             925                              930                     935 | 2835 |
| ccc cac ctc ctg ttc tct agt gag tct acc ctg cac cgc tat gag gtt<br>Pro His Leu Leu Phe Ser Ser Glu Ser Thr Leu His Arg Tyr Glu Val<br>             940                              945                     950 | 2883 |
| cac cca tat ggg acc ctc cca gtg ggt cct ggc cca gaa ttc aaa acc<br>His Pro Tyr Gly Thr Leu Pro Val Gly Pro Gly Pro Glu Phe Lys Thr<br>955                            960                            965                     970 | 2931 |
| act ctc agg act aac aat gca agc tgc ata gtg cag aac ctg act gaa<br>Thr Leu Arg Thr Asn Asn Ala Ser Cys Ile Val Gln Asn Leu Thr Glu<br>             975                              980                     985 | 2979 |
| ccc cca ggc cca cct gtg cat cca gag gag ctt caa cac aca aac aga<br>Pro Pro Gly Pro Pro Val His Pro Glu Glu Leu Gln His Thr Asn Arg<br>             990                              995                    1000 | 3027 |
| ctg aat ggg agc aat act cag tgt cag gtg gtg agg tgc cac ctt ggg<br>Leu Asn Gly Ser Asn Thr Gln Cys Gln Val Val Arg Cys His Leu Gly<br>          1005                         1010                        1015 | 3075 |
| cag ctg gca aag ggg act gag gtc tct gtt gga cta ttg agg ctg gtt<br>Gln Leu Ala Lys Gly Thr Glu Val Ser Val Gly Leu Leu Arg Leu Val<br>          1020                         1025                        1030 | 3123 |
| cac aat gaa ttt ttc cga aga gcc aag ttc aag tcc ctg acg gtg gtc<br>His Asn Glu Phe Phe Arg Arg Ala Lys Phe Lys Ser Leu Thr Val Val<br>1035                        1040                         1045                        1050 | 3171 |
| agc acc ttt gag ctg gga acc gaa gag ggc agt gtc cta cag ctg act<br>Ser Thr Phe Glu Leu Gly Thr Glu Glu Gly Ser Val Leu Gln Leu Thr<br>          1055                         1060                        1065 | 3219 |
| gaa gcc tcc cgt tgg agt gag agc ctc ttg gag gtg gtt cag acc cgg<br>Glu Ala Ser Arg Trp Ser Glu Ser Leu Leu Glu Val Val Gln Thr Arg<br>          1070                         1075                        1080 | 3267 |
| cct atc ctc atc tcc ctg tgg atc ctc ata ggc agt gtc ctg gga ggg<br>Pro Ile Leu Ile Ser Leu Trp Ile Leu Ile Gly Ser Val Leu Gly Gly<br>          1085                         1090                        1095 | 3315 |
| ttg ctc ctg ctt gct ctc ctt gtc ttc tgc ctg tgg aag ctt ggc ttc<br>Leu Leu Leu Leu Ala Leu Leu Val Phe Cys Leu Trp Lys Leu Gly Phe<br>          1100                         1105                        1110 | 3363 |
| ttt gcc cat aag aaa atc cct gag gaa gaa aaa aga gaa gag aag ttg<br>Phe Ala His Lys Lys Ile Pro Glu Glu Glu Lys Arg Glu Glu Lys Leu | 3411 |

```
                1115           1120           1125           1130
      gag caa tgaatgtaga ataagggtct agaaagtcct ccctggcagc tttcttcaag      3467
      Glu Gln agacttgcat aaaagcagag gtttgggggc tcagatggga caagaagccg cctctggact   3527
atctccccag accagcagcc tgacttgact tttgagtcct agggatgctg ctggctagag   3587
atgaggcttt acctcagaca agaagagctg gcaccaaaac tagccatgct cccaccctct   3647
gcttccctcc tcctcgtgat cctggttcca tagccaacac tggggctttt gtttggggtc   3707
cttttatccc caggaatcaa taattttttt gcctaggaaa aaaaaaagcg gccgcgaatt   3767
cgatatcaag ct                                                        3779
```

```
<210> SEQ ID NO 3
<211> LENGTH: 143
<212> TYPE: DNA
<213> ORGANISM: Homo sapiens
<220> FEATURE:
<221> NAME/KEY: CDS
<222> LOCATION: (2)..(142)

<400> SEQUENCE: 3 g ggg cat atg gtt cag aac ctg ggt tgc tac gtt gtt tcc ggt ctg atc       49
  Gly His Met Val Gln Asn Leu Gly Cys Tyr Val Val Ser Gly Leu Ile
   1               5                  10                  15 atc tcc gct ctg ctg ccg gct gtt gct cac ggt ggt aac tac ttc cta         97
Ile Ser Ala Leu Leu Pro Ala Val Ala His Gly Gly Asn Tyr Phe Leu
             20                  25                  30 agc ttg tcc cag gtt atc agc ggc ctg gtg ccg cgc gga tcc ccc c          143
Ser Leu Ser Gln Val Ile Ser Gly Leu Val Pro Arg Gly Ser Pro
         35                  40                  45

<210> SEQ ID NO 4
<211> LENGTH: 1167
<212> TYPE: PRT
<213> ORGANISM: Homo sapiens

<400> SEQUENCE: 4

Met Glu Leu Pro Phe Val Thr His Leu Phe Leu Pro Leu Val Phe Leu
 1               5                  10                  15

Thr Gly Leu Cys Ser Pro Phe Asn Leu Asp Glu His His Pro Arg Leu
             20                  25                  30

Phe Pro Gly Pro Pro Glu Ala Glu Phe Gly Tyr Ser Val Leu Gln His
         35                  40                  45

Val Gly Gly Gly Gln Arg Trp Met Leu Val Gly Ala Pro Trp Asp Gly
     50                  55                  60

Pro Ser Gly Asp Arg Arg Gly Asp Val Tyr Arg Cys Pro Val Gly Gly
 65                  70                  75                  80

Ala His Asn Ala Pro Cys Ala Lys Gly His Leu Gly Asp Tyr Gln Leu
                 85                  90                  95

Gly Asn Ser Ser His Pro Ala Val Asn Met His Leu Gly Met Ser Leu
            100                 105                 110

Leu Glu Thr Asp Gly Asp Gly Gly Phe Met Ala Cys Ala Pro Leu Trp
        115                 120                 125

Ser Arg Ala Cys Gly Ser Ser Val Phe Ser Gly Ile Cys Ala Arg
    130                 135                 140

Val Asp Ala Ser Phe Gln Pro Gln Gly Ser Leu Ala Pro Thr Ala Gln
145                 150                 155                 160

Arg Cys Pro Thr Tyr Met Asp Val Val Ile Val Leu Asp Gly Ser Asn
```

```
                    165                 170                 175
Ser Ile Tyr Pro Trp Ser Glu Val Gln Thr Phe Leu Arg Arg Leu Val
                180                 185                 190

Gly Lys Leu Phe Ile Asp Pro Glu Gln Ile Gln Val Gly Leu Val Gln
            195                 200                 205

Tyr Gly Glu Ser Pro Val His Glu Trp Ser Leu Gly Asp Phe Arg Thr
        210                 215                 220

Lys Glu Glu Val Val Arg Ala Ala Lys Asn Leu Ser Arg Arg Glu Gly
225                 230                 235                 240

Arg Glu Thr Lys Thr Ala Gln Ala Ile Met Val Ala Cys Thr Glu Gly
                245                 250                 255

Phe Ser Gln Ser His Gly Gly Arg Pro Glu Ala Ala Arg Leu Leu Val
                260                 265                 270

Val Val Thr Asp Gly Glu Ser His Asp Gly Glu Glu Leu Pro Ala Ala
                275                 280                 285

Leu Lys Ala Cys Glu Ala Gly Arg Val Thr Arg Tyr Gly Ile Ala Val
            290                 295                 300

Leu Gly His Tyr Leu Arg Arg Gln Arg Asp Pro Ser Ser Phe Leu Arg
305                 310                 315                 320

Glu Ile Arg Thr Ile Ala Ser Asp Pro Asp Glu Arg Phe Phe Phe Asn
                325                 330                 335

Val Thr Asp Glu Ala Ala Leu Thr Asp Ile Val Asp Ala Leu Gly Asp
                340                 345                 350

Arg Ile Phe Gly Leu Glu Gly Ser His Ala Glu Asn Glu Ser Ser Phe
            355                 360                 365

Gly Leu Glu Met Ser Gln Ile Gly Phe Ser Thr His Arg Leu Lys Asp
        370                 375                 380

Gly Ile Leu Phe Gly Met Val Gly Ala Tyr Asp Trp Gly Gly Ser Val
385                 390                 395                 400

Leu Trp Leu Glu Gly Gly His Arg Leu Phe Pro Pro Arg Met Ala Leu
                405                 410                 415

Glu Asp Glu Phe Pro Pro Ala Leu Gln Asn His Ala Ala Tyr Leu Gly
                420                 425                 430

Tyr Ser Val Ser Ser Met Leu Leu Arg Gly Gly Arg Arg Leu Phe Leu
            435                 440                 445

Ser Gly Ala Pro Arg Phe Arg His Arg Gly Lys Val Ile Ala Phe Gln
450                 455                 460

Leu Lys Lys Asp Gly Ala Val Arg Val Ala Gln Ser Leu Gln Gly Glu
465                 470                 475                 480

Gln Ile Gly Ser Tyr Phe Gly Ser Glu Leu Cys Pro Leu Asp Thr Asp
                485                 490                 495

Arg Asp Gly Thr Thr Asp Val Leu Leu Val Ala Ala Pro Met Phe Leu
                500                 505                 510

Gly Pro Gln Asn Lys Glu Thr Gly Arg Val Tyr Val Tyr Leu Val Gly
            515                 520                 525

Gln Gln Ser Leu Leu Thr Leu Gln Gly Thr Leu Gln Pro Glu Pro Pro
        530                 535                 540

Gln Asp Ala Arg Phe Gly Phe Ala Met Gly Ala Leu Pro Asp Leu Asn
545                 550                 555                 560

Gln Asp Gly Phe Ala Asp Val Ala Val Gly Ala Pro Leu Glu Asp Gly
                565                 570                 575

His Gln Gly Ala Leu Tyr Leu Tyr His Gly Thr Gln Ser Gly Val Arg
                580                 585                 590
```

```
Pro His Pro Ala Gln Arg Ile Ala Ala Ala Ser Met Pro His Ala Leu
        595                 600                 605

Ser Tyr Phe Gly Arg Ser Val Asp Gly Arg Leu Asp Leu Asp Gly Asp
        610                 615                 620

Asp Leu Val Asp Val Ala Val Gly Ala Gln Gly Ala Ala Ile Leu Leu
625                 630                 635                 640

Ser Ser Arg Pro Ile Val His Leu Thr Pro Ser Leu Glu Val Thr Pro
                645                 650                 655

Gln Ala Ile Ser Val Val Gln Arg Asp Cys Arg Arg Gly Gln Glu
                660                 665                 670

Ala Val Cys Leu Thr Ala Ala Leu Cys Phe Gln Val Thr Ser Arg Thr
            675                 680                 685

Pro Gly Arg Trp Asp His Gln Phe Tyr Met Arg Phe Thr Ala Ser Leu
        690                 695                 700

Asp Glu Trp Thr Ala Gly Ala Arg Ala Ala Phe Asp Gly Ser Gly Gln
705                 710                 715                 720

Arg Leu Ser Pro Arg Arg Leu Arg Leu Ser Val Gly Asn Val Thr Cys
                725                 730                 735

Glu Gln Leu His Phe His Val Leu Asp Thr Ser Asp Tyr Leu Arg Pro
            740                 745                 750

Val Ala Leu Thr Val Thr Phe Ala Leu Asp Asn Thr Thr Lys Pro Gly
        755                 760                 765

Pro Val Leu Asn Glu Gly Ser Pro Thr Ser Ile Gln Lys Leu Val Pro
770                 775                 780

Phe Ser Lys Asp Cys Gly Pro Asp Asn Glu Cys Val Thr Asp Leu Val
785                 790                 795                 800

Leu Gln Val Asn Met Asp Ile Arg Gly Ser Arg Lys Ala Pro Phe Val
                805                 810                 815

Val Arg Gly Gly Arg Arg Lys Val Leu Val Ser Thr Thr Leu Glu Asn
            820                 825                 830

Arg Lys Glu Asn Ala Tyr Asn Thr Ser Leu Ser Ile Ile Phe Ser Arg
        835                 840                 845

Asn Leu His Leu Ala Ser Leu Thr Pro Gln Arg Glu Ser Pro Ile Lys
        850                 855                 860

Val Glu Cys Ala Ala Pro Ser Ala His Ala Arg Leu Cys Ser Val Gly
865                 870                 875                 880

His Pro Val Phe Gln Thr Gly Ala Lys Val Thr Phe Leu Leu Glu Phe
                885                 890                 895

Glu Phe Ser Cys Ser Ser Leu Leu Ser Gln Val Phe Gly Lys Leu Thr
            900                 905                 910

Ala Ser Ser Asp Ser Leu Glu Arg Asn Gly Thr Leu Gln Glu Asn Thr
        915                 920                 925

Ala Gln Thr Ser Ala Tyr Ile Gln Tyr Glu Pro His Leu Leu Phe Ser
930                 935                 940

Ser Glu Ser Thr Leu His Arg Tyr Glu Val His Pro Tyr Gly Thr Leu
945                 950                 955                 960

Pro Val Gly Pro Gly Pro Glu Phe Lys Thr Thr Leu Arg Val Gln Asn
                965                 970                 975

Leu Gly Cys Tyr Val Val Ser Gly Leu Ile Ile Ser Ala Leu Leu Pro
            980                 985                 990

Ala Val Ala His Gly Gly Asn Tyr Phe Leu Ser Leu Ser Gln Val Ile
        995                 1000                1005
```

```
Thr Asn Asn Ala Ser Cys Ile Val Gln Asn Leu Thr Glu Pro Pro Gly
1010                1015                1020

Pro Pro Val His Pro Glu Glu Leu Gln His Thr Asn Arg Leu Asn Gly
1025                1030                1035                1040

Ser Asn Thr Gln Cys Gln Val Val Arg Cys His Leu Gly Gln Leu Ala
            1045                1050                1055

Lys Gly Thr Glu Val Ser Val Gly Leu Leu Arg Leu Val His Asn Glu
        1060                1065                1070

Phe Phe Arg Arg Ala Lys Phe Lys Ser Leu Thr Val Val Ser Thr Phe
    1075                1080                1085

Glu Leu Gly Thr Glu Glu Gly Ser Val Leu Gln Leu Thr Glu Ala Ser
    1090                1095                1100

Arg Trp Ser Glu Ser Leu Leu Glu Val Val Gln Thr Arg Pro Ile Leu
1105                1110                1115                1120

Ile Ser Leu Trp Ile Leu Ile Gly Ser Val Leu Gly Gly Leu Leu Leu
                1125                1130                1135

Leu Ala Leu Leu Val Phe Cys Leu Trp Lys Gly Phe Phe Ala His
            1140                1145                1150

Lys Lys Ile Pro Glu Glu Glu Lys Arg Glu Glu Lys Leu Glu Gln
        1155                1160                1165

<210> SEQ ID NO 5
<211> LENGTH: 1132
<212> TYPE: PRT
<213> ORGANISM: Homo sapiens

<400> SEQUENCE: 5

Met Glu Leu Pro Phe Val Thr His Leu Phe Leu Pro Leu Val Phe Leu
  1               5                  10                  15

Thr Gly Leu Cys Ser Pro Phe Asn Leu Asp Glu His His Pro Arg Leu
                20                  25                  30

Phe Pro Gly Pro Pro Glu Ala Glu Phe Gly Tyr Ser Val Leu Gln His
            35                  40                  45

Val Gly Gly Gly Gln Arg Trp Met Leu Val Gly Ala Pro Trp Asp Gly
        50                  55                  60

Pro Ser Gly Asp Arg Arg Gly Asp Val Tyr Arg Cys Pro Val Gly Gly
 65                  70                  75                  80

Ala His Asn Ala Pro Cys Ala Lys Gly His Leu Gly Asp Tyr Gln Leu
                85                  90                  95

Gly Asn Ser Ser His Pro Ala Val Asn Met His Leu Gly Met Ser Leu
                100                 105                 110

Leu Glu Thr Asp Gly Asp Gly Gly Phe Met Ala Cys Ala Pro Leu Trp
            115                 120                 125

Ser Arg Ala Cys Gly Ser Ser Val Phe Ser Ser Gly Ile Cys Ala Arg
        130                 135                 140

Val Asp Ala Ser Phe Gln Pro Gln Gly Ser Leu Ala Pro Thr Ala Gln
145                 150                 155                 160

Arg Cys Pro Thr Tyr Met Asp Val Val Ile Val Leu Asp Gly Ser Asn
                165                 170                 175

Ser Ile Tyr Pro Trp Ser Glu Val Gln Thr Phe Leu Arg Arg Leu Val
                180                 185                 190

Gly Lys Leu Phe Ile Asp Pro Glu Gln Ile Gln Val Gly Leu Val Gln
            195                 200                 205

Tyr Gly Glu Ser Pro Val His Glu Trp Ser Leu Gly Asp Phe Arg Thr
        210                 215                 220
```

-continued

```
Lys Glu Glu Val Val Arg Ala Ala Lys Asn Leu Ser Arg Arg Glu Gly
225                 230                 235                 240

Arg Glu Thr Lys Thr Ala Gln Ala Ile Met Val Ala Cys Thr Glu Gly
            245                 250                 255

Phe Ser Gln Ser His Gly Gly Arg Pro Glu Ala Ala Arg Leu Leu Val
        260                 265                 270

Val Val Thr Asp Gly Glu Ser His Asp Gly Glu Glu Leu Pro Ala Ala
    275                 280                 285

Leu Lys Ala Cys Glu Ala Gly Arg Val Thr Arg Tyr Gly Ile Ala Val
290                 295                 300

Leu Gly His Tyr Leu Arg Arg Gln Arg Asp Pro Ser Ser Phe Leu Arg
305                 310                 315                 320

Glu Ile Arg Thr Ile Ala Ser Asp Pro Asp Glu Arg Phe Phe Phe Asn
                325                 330                 335

Val Thr Asp Glu Ala Ala Leu Thr Asp Ile Val Asp Ala Leu Gly Asp
            340                 345                 350

Arg Ile Phe Gly Leu Glu Gly Ser His Ala Glu Asn Glu Ser Ser Phe
        355                 360                 365

Gly Leu Glu Met Ser Gln Ile Gly Phe Ser Thr His Arg Leu Lys Asp
370                 375                 380

Gly Ile Leu Phe Gly Met Val Gly Ala Tyr Asp Trp Gly Gly Ser Val
385                 390                 395                 400

Leu Trp Leu Glu Gly Gly His Arg Leu Phe Pro Pro Arg Met Ala Leu
                405                 410                 415

Glu Asp Glu Phe Pro Pro Ala Leu Gln Asn His Ala Ala Tyr Leu Gly
            420                 425                 430

Tyr Ser Val Ser Ser Met Leu Leu Arg Gly Gly Arg Arg Leu Phe Leu
        435                 440                 445

Ser Gly Ala Pro Arg Phe Arg His Arg Gly Lys Val Ile Ala Phe Gln
450                 455                 460

Leu Lys Lys Asp Gly Ala Val Arg Val Ala Gln Ser Leu Gln Gly Glu
465                 470                 475                 480

Gln Ile Gly Ser Tyr Phe Gly Ser Glu Leu Cys Pro Leu Asp Thr Asp
                485                 490                 495

Arg Asp Gly Thr Thr Asp Val Leu Leu Val Ala Ala Pro Met Phe Leu
            500                 505                 510

Gly Pro Gln Asn Lys Glu Thr Gly Arg Val Tyr Val Tyr Leu Val Gly
        515                 520                 525

Gln Gln Ser Leu Leu Thr Leu Gln Gly Thr Leu Gln Pro Glu Pro Pro
530                 535                 540

Gln Asp Ala Arg Phe Gly Phe Ala Met Gly Ala Leu Pro Asp Leu Asn
545                 550                 555                 560

Gln Asp Gly Phe Ala Asp Val Ala Val Gly Ala Pro Leu Glu Asp Gly
                565                 570                 575

His Gln Gly Ala Leu Tyr Leu Tyr His Gly Thr Gln Ser Gly Val Arg
            580                 585                 590

Pro His Pro Ala Gln Arg Ile Ala Ala Ala Ser Met Pro His Ala Leu
        595                 600                 605

Ser Tyr Phe Gly Arg Ser Val Asp Gly Arg Leu Asp Leu Asp Gly Asp
610                 615                 620

Asp Leu Val Asp Val Ala Val Gly Ala Gln Gly Ala Ala Ile Leu Leu
625                 630                 635                 640
```

```
Ser Ser Arg Pro Ile Val His Leu Thr Pro Ser Leu Glu Val Thr Pro
            645                 650                 655

Gln Ala Ile Ser Val Val Gln Arg Asp Cys Arg Arg Gly Gln Glu
        660                 665                 670

Ala Val Cys Leu Thr Ala Ala Leu Cys Phe Gln Val Thr Ser Arg Thr
            675                 680                 685

Pro Gly Arg Trp Asp His Gln Phe Tyr Met Arg Phe Thr Ala Ser Leu
        690                 695                 700

Asp Glu Trp Thr Ala Gly Ala Arg Ala Ala Phe Asp Gly Ser Gly Gln
705                 710                 715                 720

Arg Leu Ser Pro Arg Arg Leu Arg Leu Ser Val Gly Asn Val Thr Cys
            725                 730                 735

Glu Gln Leu His Phe His Val Leu Asp Thr Ser Asp Tyr Leu Arg Pro
            740                 745                 750

Val Ala Leu Thr Val Thr Phe Ala Leu Asp Asn Thr Thr Lys Pro Gly
            755                 760                 765

Pro Val Leu Asn Glu Gly Ser Pro Thr Ser Ile Gln Lys Leu Val Pro
        770                 775                 780

Phe Ser Lys Asp Cys Gly Pro Asp Asn Glu Cys Val Thr Asp Leu Val
785                 790                 795                 800

Leu Gln Val Asn Met Asp Ile Arg Gly Ser Arg Lys Ala Pro Phe Val
                805                 810                 815

Val Arg Gly Arg Arg Lys Val Leu Val Ser Thr Thr Leu Glu Asn
            820                 825                 830

Arg Lys Glu Asn Ala Tyr Asn Thr Ser Leu Ser Ile Ile Phe Ser Arg
        835                 840                 845

Asn Leu His Leu Ala Ser Leu Thr Pro Gln Arg Glu Ser Pro Ile Lys
        850                 855                 860

Val Glu Cys Ala Ala Pro Ser Ala His Ala Arg Leu Cys Ser Val Gly
865                 870                 875                 880

His Pro Val Phe Gln Thr Gly Ala Lys Val Thr Phe Leu Leu Glu Phe
                885                 890                 895

Glu Phe Ser Cys Ser Ser Leu Leu Ser Gln Val Phe Gly Lys Leu Thr
            900                 905                 910

Ala Ser Ser Asp Ser Leu Glu Arg Asn Gly Thr Leu Gln Glu Asn Thr
        915                 920                 925

Ala Gln Thr Ser Ala Tyr Ile Gln Tyr Glu Pro His Leu Leu Phe Ser
        930                 935                 940

Ser Glu Ser Thr Leu His Arg Tyr Glu Val His Pro Tyr Gly Thr Leu
945                 950                 955                 960

Pro Val Gly Pro Gly Pro Glu Phe Lys Thr Thr Leu Arg Thr Asn Asn
                965                 970                 975

Ala Ser Cys Ile Val Gln Asn Leu Thr Glu Pro Pro Gly Pro Pro Val
            980                 985                 990

His Pro Glu Glu Leu Gln His Thr Asn Arg Leu Asn Gly Ser Asn Thr
        995                 1000                1005

Gln Cys Gln Val Val Arg Cys His Leu Gly Gln Leu Ala Lys Gly Thr
    1010                1015                1020

Glu Val Ser Val Gly Leu Leu Arg Leu Val His Asn Glu Phe Phe Arg
1025                1030                1035                1040

Arg Ala Lys Phe Lys Ser Leu Thr Val Val Ser Thr Phe Glu Leu Gly
            1045                1050                1055

Thr Glu Glu Gly Ser Val Leu Gln Leu Thr Glu Ala Ser Arg Trp Ser
```

```
                     1060              1065              1070
Glu Ser Leu Leu Glu Val Val Gln Thr Arg Pro Ile Leu Ile Ser Leu
        1075              1080              1085

Trp Ile Leu Ile Gly Ser Val Leu Gly Gly Leu Leu Leu Ala Leu
        1090              1095              1100

Leu Val Phe Cys Leu Trp Lys Leu Gly Phe Phe Ala His Lys Lys Ile
1105              1110              1115              1120

Pro Glu Glu Glu Lys Arg Glu Glu Lys Leu Glu Gln
            1125              1130

<210> SEQ ID NO 6
<211> LENGTH: 47
<212> TYPE: PRT
<213> ORGANISM: Homo sapiens

<400> SEQUENCE: 6

Gly His Met Val Gln Asn Leu Gly Cys Tyr Val Val Ser Gly Leu Ile
1               5                   10                  15

Ile Ser Ala Leu Leu Pro Ala Val Ala His Gly Gly Asn Tyr Phe Leu
            20                  25                  30

Ser Leu Ser Gln Val Ile Ser Gly Leu Val Pro Arg Gly Ser Pro
        35                  40                  45

<210> SEQ ID NO 7
<211> LENGTH: 22
<212> TYPE: PRT
<213> ORGANISM: Homo sapiens

<400> SEQUENCE: 7

Lys Leu Gly Phe Phe Ala His Lys Lys Ile Pro Glu Glu Glu Lys Arg
1               5                   10                  15

Glu Glu Lys Leu Glu Gln
            20

<210> SEQ ID NO 8
<211> LENGTH: 7
<212> TYPE: PRT
<213> ORGANISM: Homo sapiens

<400> SEQUENCE: 8

Lys Leu Gly Phe Phe Ala His
1               5

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: Inosine
<220> FEATURE:
<221> NAME/KEY: modified_base
<222> LOCATION: (12)
<223> OTHER INFORMATION: Inosine

<400> SEQUENCE: 9
gayaayacng cncarac                                                17

<210> SEQ ID NO 10
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asn Thr Ala Gln Thr
 1               5

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)
<223> OTHER INFORMATION: Inosine
<220> FEATURE:
<221> NAME/KEY: modified_base
<222> LOCATION: (5)
<223> OTHER INFORMATION: Inosine
<220> FEATURE:
<221> NAME/KEY: modified_base
<222> LOCATION: (14)
<223> OTHER INFORMATION: Inosine

<400> SEQUENCE: 11
tnatnswrtg rtgnggyt                                                  18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Pro His His Ser Ile
 1               5

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcagcctaca ttcagtat                                                  18

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ala Tyr Ile Gln Tyr
 1               5
```

```
<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: Inosine
<220> FEATURE:
<221> NAME/KEY: modified_base
<222> LOCATION: (13)
<223> OTHER INFORMATION: Inosine
<220> FEATURE:
<221> NAME/KEY: modified_base
<222> LOCATION: (16)
<223> OTHER INFORMATION: Inosine

<400> SEQUENCE: 15
nckrtcccar tgnccngg                                                 18

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Gly His Trp Asp Arg
 1               5

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aactcgtctt ccagtgccat tcgtggg                                       27

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttcagaacc tggttgctac gttgtttccg gtctgatcat ctccgctctg ctgccggctg   60
t                                                                   61

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggggcatatg gttcagaacc tgggttgcta cgttg                              35
```

```
<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gataacctgg gacaagctta ggaagtagtt accaccgtga gcaacagccg gcagcagagc      60
gga                                                                    63

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21 gggggggatcc gcgcggcacc aggccgctga taacctggga caagcttagg aagt           54

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (6)
<223> OTHER INFORMATION: Arg or Lys

<400> SEQUENCE: 22

Lys Xaa Gly Phe Phe Xaa Arg
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Phe Phe Lys Arg
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid

<400> SEQUENCE: 24
```

```
Lys Xaa Gly Phe Phe Lys Arg
  1               5

<210> SEQ ID NO 25
<211> LENGTH: 15
<212> TYPE: PRT
<213> ORGANISM: Homo sapiens

<400> SEQUENCE: 25

Cys Lys Lys Ile Pro Glu Glu Glu Lys Arg Glu Glu Lys Leu Glu
  1               5                  10                  15

<210> SEQ ID NO 26
<211> LENGTH: 18
<212> TYPE: PRT
<213> ORGANISM: Bos taurus

<400> SEQUENCE: 26

Asp Asn Thr Ala Gln Thr Ser Ala Tyr Ile Gln Tyr Glu Pro His His
  1               5                  10                  15

Ser Ile

<210> SEQ ID NO 27
<211> LENGTH: 7
<212> TYPE: PRT
<213> ORGANISM: Bos taurus

<400> SEQUENCE: 27

Gly Pro Gly His Trp Asp Arg
  1               5

<210> SEQ ID NO 28
<211> LENGTH: 9
<212> TYPE: PRT
<213> ORGANISM: Bos taurus

<400> SEQUENCE: 28

Ala Ala Phe Asp Gly Ser Gly Gln Arg
  1               5

<210> SEQ ID NO 29
<211> LENGTH: 8
<212> TYPE: PRT
<213> ORGANISM: Bos taurus

<400> SEQUENCE: 29

Phe Ala Met Gly Ala Leu Pro Asp
  1               5

<210> SEQ ID NO 30
<211> LENGTH: 13
<212> TYPE: PRT
<213> ORGANISM: Bos taurus

<400> SEQUENCE: 30

Phe Thr Ala Ser Leu Asp Glu Trp Thr Thr Ala Ala Arg
  1               5                  10

<210> SEQ ID NO 31
<211> LENGTH: 13
<212> TYPE: PRT
<213> ORGANISM: Bos taurus
<220> FEATURE:
<221> NAME/KEY: MOD_RES
<222> LOCATION: (10)
```

-continued

<223> OTHER INFORMATION: Variable amino acid

<400> SEQUENCE: 31

Val Asp Ala Ser Phe Arg Pro Gln Gly Xaa Leu Ala Pro
  1               5                  10

<210> SEQ ID NO 32
<211> LENGTH: 7958
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (52)..(52)
<223> OTHER INFORMATION: a, c, g, t, unknown or other
<220> FEATURE:
<221> NAME/KEY: modified_base
<222> LOCATION: (55)..(55)
<223> OTHER INFORMATION: a, c, g, t, unknown or other
<220> FEATURE:
<221> NAME/KEY: modified_base
<222> LOCATION: (62)..(62)
<223> OTHER INFORMATION: a, c, g, t, unknown or other
<220> FEATURE:
<221> NAME/KEY: modified_base
<222> LOCATION: (98)..(98)
<223> OTHER INFORMATION: a, c, g, t, unknown or other
<220> FEATURE:
<221> NAME/KEY: modified_base
<222> LOCATION: (118)..(118)
<223> OTHER INFORMATION: a, c, g, t, unknown or other
<220> FEATURE:
<221> NAME/KEY: modified_base
<222> LOCATION: (135)..(135)
<223> OTHER INFORMATION: a, c, g, t, unknown or other
<220> FEATURE:
<221> NAME/KEY: modified_base
<222> LOCATION: (145)..(145)
<223> OTHER INFORMATION: a, c, g, t, unknown or other
<220> FEATURE:
<221> NAME/KEY: modified_base
<222> LOCATION: (151)..(151)
<223> OTHER INFORMATION: a, c, g, t, unknown or other
<220> FEATURE:
<221> NAME/KEY: modified_base
<222> LOCATION: (163)..(163)
<223> OTHER INFORMATION: a, c, g, t, unknown or other
<220> FEATURE:
<221> NAME/KEY: modified_base
<222> LOCATION: (224)..(224)
<223> OTHER INFORMATION: a, c, g, t, unknown or other
<220> FEATURE:
<221> NAME/KEY: modified_base
<222> LOCATION: (233)..(233)
<223> OTHER INFORMATION: a, c, g, t, unknown or other
<220> FEATURE:
<221> NAME/KEY: modified_base
<222> LOCATION: (246)..(246)
<223> OTHER INFORMATION: a, c, g, t, unknown or other
<220> FEATURE:
<221> NAME/KEY: modified_base
<222> LOCATION: (275)..(275)
<223> OTHER INFORMATION: a, c, g, t, unknown or other
<220> FEATURE:
<221> NAME/KEY: modified_base
<222> LOCATION: (364)..(364)
<223> OTHER INFORMATION: a, c, g, t, unknown or other
<220> FEATURE:
<221> NAME/KEY: modified_base
<222> LOCATION: (406)..(406)

```
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (452)..(452)
<223> OTHER INFORMATION: a, c, g, t, unknown or other
<220> FEATURE:
<221> NAME/KEY: modified_base
<222> LOCATION: (467)..(467)
<223> OTHER INFORMATION: a, c, g, t, unknown or other
<220> FEATURE:
<221> NAME/KEY: modified_base
<222> LOCATION: (473)..(473)
<223> OTHER INFORMATION: a, c, g, t, unknown or other
<220> FEATURE:
<221> NAME/KEY: modified_base
<222> LOCATION: (995)..(995)
<223> OTHER INFORMATION: a, c, g, t, unknown or other
<220> FEATURE:
<221> NAME/KEY: modified_base
<222> LOCATION: (1074)..(1074)
<223> OTHER INFORMATION: a, c, g, t, unknown or other
<220> FEATURE:
<221> NAME/KEY: modified_base
<222> LOCATION: (1106)..(1106)
<223> OTHER INFORMATION: a, c, g, t, unknown or other

<400> SEQUENCE: 32
tgntmmmkcm cacgakmgws akgnccgakg gtkgkgvaav gtgacaragc tngmnaaaar      60
angaagtatg accwgtgggc cragatagmk amdaagcngm sagktramgg acgatggncc     120
mgccaavcga bwggnaahtb cggcnwdcar ngtccaaatk sanktcscag gaaccmacgg     180
amtggctcgc arcccdtagg gatcaggkac gatgrctcsc cgrnskactc sgnktgatwa     240
atcgmnwgtm ggmaggcggm ggaattrwaa agtantggtm gamakatgwg vmggawatga     300
trrgtmgact vtmvmggvak vtaksggtac aggcgaaakac argrakgtgt ctgaggaadt    360
cagnaggaca ammttgccga agtcmggact tagkatrgat acgaancktr gatcttamad    420
gggggnkagc gagtgcstaa acgvaratrg gnswgtctac ttmaacnccca agngdggaca    480 tttactagas gaggagagta gccagatcac dtgagatgat ctaakgtggg gtcccgttgc    540
cagtatatga gaggactggt tcggcagaca twgatgctct tgctgactc acatattgtt    600 gccvtgagka tgatcagata cgatctgwtg tccctcatca tgaatstgrg ccgtgatgct    660
aatgagattc gcctatgatg aacaagaga cttmtgctac agcaggcgaa tgaaggtttc    720
tagagtagga gtctcaggag gagagaaact gtggacctgg aggaccaggg actccaggag    780
gaagtwgcca caactggctt gmagtttcgg ctccgatcct gatacwggct cgtccttvga    840
gttatccccc tctcttgctg gatggctcag aaatgcctgg acctttttcat ccccactgga    900 caaactaggc gtctggcgtt gtggccctgg gattgtgggg ctgtgtggcc tcatatcctc    960
cattctgtct attctcaccc taatctgtcc ctggntacga ctcaagcccy gactgacamt   1020
gtggtacaag ataaggaggg agcccaggtg ggtgagatgg aagctgagat ggtncactgt   1080
gtgccmacct cattgtaatt caactnccctt gactgaagtt aaaatccaga tccytaggga   1140 tgagggaag aacctgccaa agacgggtca ggaaggcagt gctaagggaa ggctcctgca   1200
ggcctctgca gttggacttc attcagtccc attgccagaa tctcatagct cttcccyyta   1260
tctctctgtc ttgagtctag ttaagaattt gttaccggag acagaattct ctttcttagc   1320
ctcctggcca gatatttaaa aggagggggg tgggttactt tttggtaggg gaagcttaag   1380
ttatggatag caaagtgcta attgtattct ttttttctga aacctcatgt agcattttc    1440
```

```
ttcccttcca ccctccatac tttcccaggc ttcatttcat gcccggcgtc tcttcgctca      1500
caccgctgca ggctgtttga ggcttctccc ctgggtctgc ctcagcagac tgcctccaca     1560
ctttccagtt tctgcgtaca cgttgatatt agagtttcct tccccacttg gctcttgctc     1620
tttctctgac tacccaggct gatgccatgt ctggcctctt cctgtaaata ctgtacaatg     1680
attctatgta aataactggt ccttgcccac agagcaagca agccttctag gctaacaaat     1740
taaagatcaa gtttgctcac tgactttttt attcaattca agatggcggg gggtggggtg     1800 gggggggcgga ttgcctgttt tcactgtggt acctaggcag ggctgaagct ctgagctccc    1860
ctgctttagg cttctgagta gcctacagtg agtgttactg tgtccagctg ctcgttgaca     1920
tctggtctct catggtctgg tcattgtaag ccttagctct ctgactgtgg atggctttcc     1980
ttggcgttag cagctaacat ggttacagga tttcactgaa aatttaaatg ttgggggaaa    2040
ggtgcggaca caccataatg gtcccaattc aaaacaatcc gtgaaacagc ctcaagttag    2100
gggtgagatg ttttcaacca agtaattat cttgacacca caaagcacac ctgtctacag     2160
gcagtgactc cccaaaagct attagacaca caacaagcat gaccataact cagtggattg    2220
gcaaggtcac acagtaggac tgcccttcac acagtaggta ggaaaatgct gctgtcactg    2280
ctgtcagctg ttattttgca tatcccatgt taagattaat aaggcaaaaa atattgtctc   2340
taagtcctac tttctgttcc aaactggagg aaattattga ataaataaac cgtgcataaa   2400
agtagcctca gaaagggtca aaatttgtgt tttctttgaa tattagctga ggcctccagg    2460
gggcagcacc aagtagaga gctggactaa ggctgctctg tgttcctgtc ctgggctccc    2520
cacagctccc ttccaccacc actcccattc catccaactt tattttagc tgccagtggg    2580 aggggggcagg ataggaggga aagtaacgaa acagccaag gagagggaca gagcaactca    2640
gagcctctcg gactggaccg gacaagcgcc catggagtct ctctccatcc ctcacctgct    2700
cctgcccctg gcgtwgctga caggtgaggg aagcaaactt ggtttctgct gggaatggaa    2760
gttatgtgga ttgttttataa ttgggaccat tatggctaaa atctygcggg cgctcaggtc   2820
ggaggttaat accgatgcta tatttcctgt gtgcactcat gttcttagac acccaaatgg    2880
cagtggccaa aacttcctct ggcttgtacc tcattatcta aacctttgta cctaattatc    2940
taaaaccttg gtcctaaact ccacagacat gagggcacag aaaagagacg tgtctctcat    3000
cttccattcg gttacactga ttcctaccttt ccctgcttct ccctgccatt ggtgctcctt    3060
ggtgcctgag gcataattgc cttactatgt ggtcagaact ctgggttcgc ctaacgaccg    3120
agctacagtt tctggtctca tagccctgcc aatttcctgg attaaaaaaa aaggctcac    3180 atataaaata cctttctga aaatgagcac agtgtgagtt gaagttagat tttggggat     3240 ggaggttgc ttggatgcaa agagcaagac agtagagaag agaatcatgg gagggataag    3300
aggctggaat tttccctgc tagtgcccta taatctttgt ttcctaaaat aacagctctg    3360
attttatggg aattggggtc aggagaaagg aatcagtagg cacagatggg accccaagcg    3420
tggactaaag tttgaggaaa ctatgggagt aggcaagggg tgtttgtaag gtggatgaga    3480
tgaggagatt gtggtgggg ggagtcttgg gggtgatagg acccttaaca gggatagatg    3540
gcaaactgtg tgtgggcagg ccggtggttc caccccactta attagcgttg aggttggcag   3600
ggctggaagg agccagcact ctcaaccttg gagaaagtgc aagtgtgaca agaagaaaca   3660
gaaagaggag acacccgggc agggagctcc ttgccatcgt ttcttcccat ggccctggct   3720
ttgggaagaa ttaggaaagg gtggtgactc tgcatcctca gaaaagccct ctctccctct   3780
```

```
ttggactctc gaggcttaga gaggagaatg tgtaggagga atgatgtgga aagagtaact    3840
tgacctatcc agatgtgtct gtgaatgaga tttcaggaat gagaatggaa atacagctgt    3900
gcttcagcat ggccgagggc cttaggatcc ctcaccccca ccccacagga agagaatcat    3960
ccaatcatcc cacctggggt tctgaggaca tgacattgac acagagcagg agagctgaga    4020
tagaaacact ccctcctgtc ttgtctccca ctaagcctca ccagtccttc attaactgat    4080
tggtggatgc taattatgat cctcacccct caggtctctg ctcccccttt aatctggatg    4140
aacaccaccc acgactcttc acagggccac cagaggccga atttggatac agtgtcttac    4200
agcatgttgg gggtggacag cgatggtgag agggaaaaca gaggaccgtg gatcgggac    4260
tatgcactca ctgataaagg ggaggaccgg tccaagctgg cctttgaaag tgcctggggc    4320
tccatgacgt ctcatgcact ctccctctca ctatactaag gaccatgctc accggatctt    4380
tatatccata ttctccttcc aggatgctgg tgggtgcccc ctgggatggg ccatcaggtg    4440
accggagagg ggatgtttat cgttgctcta taggggatt ccacagtgct ccatgtacca    4500
aaggccacct gggtaagaag aagcctgacc tttcccctgc taattcctga tgttgacatc    4560
tagtaactct gaccccttgg accttgtctt caatgaccct gaactaaaga gccgaacta    4620
tgaccccatg acttcattct cttctaccct cctccaacc aggtgactat caacttggaa    4680
attcctctca gcctgctgtg aatatgcacc tagggatgtc tctactagag acagatgctg    4740
atgggggatt catggtgagc tgaaagaagg gcctcagaag gttcacagca gggaagagag    4800
cattatggta tctgggcagt ggtggcttgg gcctttcatc ccagtgttct ggaggcagag    4860
tcaggcctga tctacagagt gagctccagg acagccaagg ctatgcagag aaaccctgtt    4920
ttgaaaaacc caaaccaaa actaaccaaa caacaacaac agaaaaagca ccgtggtaag    4980
ggaaattagt ctgtatagaa gagacaagga attcaaaacc ctagagagca aggcagggtt    5040
ccccatggag tggtctccat ctctctttta actaggtgtg tgttccgaga ggccctctca    5100
agcctgggga taactatttc tcctatccac ccaggcctgt gcccctcttt ggtctcgtgc    5160
ctgcggcagc tctgtcttca gttctggaat atgtgcccgt gtggatgctt cattccggcc    5220
ccagggaagc ctggcaccca ccgcccaacg tgagccagtg aagggccct ggaagctcag    5280
ttcccagata gggatgctgg gtgggaaaaa ctaggacaaa gacttggtgg agggtctgca    5340
tggctatcct catcattccc aagtgtgctt gcagaagagg ctcctgtttg ctaactgatt    5400
agaattcaga ctccttagga gagcctcaag acaccaggat ctggttttac caacttaaaa    5460
acaaaacaaa acagcatatc ctgtgcacag cctatccctc atccatcacg tgtcctccat    5520
atcttatttt tgtgggtctt atagatgcca agtcagcact cagttattgg gttctcccct    5580
catgcctttc atatactttc ttatctactg ccttttggga gatagtctta tgtagcccag    5640
gctgtccttg atcttggaat ttgcttgcct cagcttctca gtctcaagta ctgggataat    5700
aggcatgcat tgtctgcctg gcctttgctg aacatgccct ctgtggccat tggtagggca    5760
tgagtcaaat actgccctcc cccacaacac acacacaaac gaaagtgagg ctctctaagt    5820
gttccatagc acagggtagt ggtaggcctc tcgctagtgc atatttcatt cttttactct    5880
gcccatctct tctttctttg atttccacac tgggacctg gcatagtact ttcctggtaa    5940
ttaagagaga attcccttt aagtgcctgc attgcagcgt cctcctggga cattctccct    6000
tgctgactac accccacatc cttccatgtt ttttgtttcc catcactatg cccccttct    6060
aggctgtccc acatacatgg atgtcgtcat tgttttggat ggctccaaca gtatctatcc    6120
ctggtcagaa gttcagactt ccttcggag gctggtagga agactgttca tcgatccgga    6180
```

```
gcagatacag gtaagagaaa gatatgtgga taggattgga gggaaagaag taaacactcc    6240
tggacccttg gatgtaagca gccatgtcca gcctcttgat gacaccctgg gacattgtct    6300
tctacagaac tcatgctcaa gaactgtgca attaacttac caaaaagtca caaaaatttc    6360
ataatgtttg aagtaagttt atgattgtgt gggggggccac actcagagct tccctttgct    6420
gcttgtagtt gcttgggcaa tgcatgccat gagctgcaag ttagacacac ctgttcactt    6480 cccccttcatc gtgctgcagg ttggacacac ctgttagggg ttcacttccc cttcatcctt    6540
tgtgctccat cttctctacg ctcttcatac atcccatgtg ggcacatggt ctattgttct    6600
caggtaggac tggtacagta cggggagaac cctgtgcatg agtggtccct gggagacttc    6660
cgaacaaagg aagaagttgt gagagcagca aggaacctaa gtcggaggga agggcgagaa    6720
acgagaaccg cccaagcgat catggtggca tggtgagaca ttgtaaaggg gtcgtgtgag    6780
ggaggaggaa ggatcagcag ggagagggag agggtctgga gtgtagtgta tacatcacaa    6840
gatgctctgg gcgcttatct ttatctgcat gccagaagtt cgtggaggaa ggctaggttg    6900
ctgtcaccat actctctctt actgtatttg cattttatgg tgtctgtggg tgtatctctc    6960
cttgtctgtt ctgtttctgc acacagaact ccatctttcc tcttctactc ctgcgtcaat    7020
tctgatacct agcttctcaa ccactcacgc cctagtattc ttttcaaaca tgactctaaa    7080
cctctgggga ggctacatga cctgactgtc tttattctcc agttccttga tcttgtcaac    7140
ccaagtgttt gctgaatgaa tctataaata aataatgctt gtacatattt acactgatga    7200
cagattattt tatatgttcc gtgccatcta aacagtcaag ttgtgactct gtgccagttt    7260
gcatgctaga tactgttggg gaatggtgta gaagacatct gacctcagtg aactgctgac    7320
agtgttaata cactatacgg gcatgcctgc atgcaagcct gtgtgtatgt gcatgcatat    7380
gcacacacat acatatgacc atatagcatt cttttatctc tcttcttagc acagaagggt    7440
tcagtcagtc ccggggggga cgaccagagg ccgctaggct gctggtagtt gtcactgatg    7500
gagagtccca tgatggagag gaacttccag cagcgctaaa ggcctgtgag gctggcagag    7560
tgacacgtta tgggattgcg gtgagacttg atcaagtcca gttgttttgt tttgtgttgt    7620
atcgtgtgtg tgtgtgtgtg tgtgtgtgtg tgtgtgtgta tgtgtgatat    7680
gtgtgcatgc atcagtgcac ataccatagt gtgtatatgc gggtcagaga acaacctcag    7740
atgttggtcc tcaccttcca tcttgttcca aactggatat cttgttcact tcggcataca    7800
ataagccaga ttagctgacc cacaagtctt gggcaggtct tctgtctcag cctcctgtct    7860
cttggtttga ggcattctgg aatttacaga taagcttgat atcgaattcc tgcagcccgg    7920
gggatccact agttctagag cggccgccac caagggag                           7958
```

<210> SEQ ID NO 33
<211> LENGTH: 78
<212> TYPE: PRT
<213> ORGANISM: Homo sapiens
<220> FEATURE:
<221> NAME/KEY: MOD_RES
<222> LOCATION: (1)..(4)
<223> OTHER INFORMATION: Variable amino acid
<220> FEATURE:
<221> NAME/KEY: MOD_RES
<222> LOCATION: (6)..(8)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:

```
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (18)..(19)
<223> OTHER INFORMATION: Variable amino acid
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid
<220> FEATURE:
<221> NAME/KEY: MOD_RES
<222> LOCATION: (28)..(28)
<223> OTHER INFORMATION: Variable amino acid
<220> FEATURE:
<221> NAME/KEY: MOD_RES
<222> LOCATION: (30)..(31)
<223> OTHER INFORMATION: Variable amino acid
<220> FEATURE:
<221> NAME/KEY: MOD_RES
<222> LOCATION: (33)..(36)
<223> OTHER INFORMATION: Variable amino acid
<220> FEATURE:
<221> NAME/KEY: MOD_RES
<222> LOCATION: (40)..(41)
<223> OTHER INFORMATION: Variable amino acid
<220> FEATURE:
<221> NAME/KEY: MOD_RES
<222> LOCATION: (43)..(44)
<223> OTHER INFORMATION: Variable amino acid
<220> FEATURE:
<221> NAME/KEY: MOD_RES
<222> LOCATION: (46)..(47)
<223> OTHER INFORMATION: Variable amino acid
<220> FEATURE:
<221> NAME/KEY: MOD_RES
<222> LOCATION: (49)..(49)
<223> OTHER INFORMATION: Variable amino acid
<220> FEATURE:
<221> NAME/KEY: MOD_RES
<222> LOCATION: (51)..(51)
<223> OTHER INFORMATION: Variable amino acid
<220> FEATURE:
<221> NAME/KEY: MOD_RES
<222> LOCATION: (54)..(56)
<223> OTHER INFORMATION: Variable amino acid
<220> FEATURE:
<221> NAME/KEY: MOD_RES
<222> LOCATION: (59)..(59)
<223> OTHER INFORMATION: Variable amino acid
<220> FEATURE:
<221> NAME/KEY: MOD_RES
<222> LOCATION: (61)..(61)
<223> OTHER INFORMATION: Variable amino acid
<220> FEATURE:
<221> NAME/KEY: MOD_RES
<222> LOCATION: (66)..(66)
<223> OTHER INFORMATION: Variable amino acid
<220> FEATURE:
<221> NAME/KEY: MOD_RES
<222> LOCATION: (70)..(70)
<223> OTHER INFORMATION: Variable amino acid
<220> FEATURE:
<221> NAME/KEY: MOD_RES
<222> LOCATION: (72)..(72)
<223> OTHER INFORMATION: Variable amino acid
<220> FEATURE:
<221> NAME/KEY: MOD_RES
<222> LOCATION: (75)..(76)
<223> OTHER INFORMATION: Variable amino acid
```

```
<220> FEATURE:
<221> NAME/KEY: MOD_RES
<222> LOCATION: (78)..(78)
<223> OTHER INFORMATION: Variable amino acid

<400> SEQUENCE: 33

Xaa Xaa Xaa Xaa Arg Xaa Xaa Xaa Pro Xaa Val Xaa Xaa Asp Xaa
1               5                   10                  15

Ala Xaa Xaa Lys Xaa Lys Tyr Asp Xaa Trp Ala Xaa Ile Xaa Xaa Lys
            20                  25                  30

Xaa Xaa Xaa Xaa Gly Arg Trp Xaa Xaa Gln Xaa Xaa Gly Xaa Xaa Gly
        35                  40                  45

Xaa Gln Xaa Pro Asn Xaa Xaa Xaa Arg Asn Xaa Arg Xaa Gly Ser Gln
    50                  55                  60

Pro Xaa Gly Ile Arg Xaa Asp Xaa Ser Pro Xaa Xaa Ser Xaa
65              70                  75

<210> SEQ ID NO 34
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (20)..(20)
<223> OTHER INFORMATION: Variable amino acid

<400> SEQUENCE: 34

Xaa Ile Xaa Xaa Arg Xaa Ala Xaa Glu Leu Xaa Ser Xaa Gly Arg Xaa
1               5                   10                  15

Met Xaa Arg Xaa
            20

<210> SEQ ID NO 35
<211> LENGTH: 17
<212> TYPE: PRT
<213> ORGANISM: Homo sapiens
<220> FEATURE:
<221> NAME/KEY: MOD_RES
```

<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (15)..(16)
<223> OTHER INFORMATION: Variable amino acid

<400> SEQUENCE: 35

Xaa Val Asp Xaa Xaa Gly Xaa Xaa Xaa Tyr Arg Arg Xaa Gln Xaa Xaa
1               5                   10                  15
Val

<210> SEQ ID NO 36
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid

<400> SEQUENCE: 36

Gly Xaa Gln Xaa Asp Xaa Xaa Ala Glu Val Arg Thr
1               5                   10

<210> SEQ ID NO 37
<211> LENGTH: 35
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (9)..(9)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (15)..(15)
<223> OTHER INFORMATION: Variable amino acid
<220> FEATURE:
<221> NAME/KEY: MOD_RES
<222> LOCATION: (18)..(21)
<223> OTHER INFORMATION: Variable amino acid
<220> FEATURE:

```
<221> NAME/KEY: MOD_RES
<222> LOCATION: (24)..(25)
<223> OTHER INFORMATION: Variable amino acid
<220> FEATURE:
<221> NAME/KEY: MOD_RES
<222> LOCATION: (27)..(28)
<223> OTHER INFORMATION: Variable amino acid
<220> FEATURE:
<221> NAME/KEY: MOD_RES
<222> LOCATION: (33)..(33)
<223> OTHER INFORMATION: Variable amino acid

<400> SEQUENCE: 37

Xaa Xaa Tyr Glu Xaa Xaa Ile Leu Xaa Gly Gly Xaa Arg Val Xaa Lys
1               5                   10                  15

Arg Xaa Xaa Xaa Xaa Leu Leu Xaa Xaa Gln Xaa Xaa Thr Phe Thr Arg
            20                  25                  30

Xaa Gly Glu
        35

<210> SEQ ID NO 38
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Variable amino acid

<400> SEQUENCE: 38

Pro Asp His Xaa Arg
1               5

<210> SEQ ID NO 39
<211> LENGTH: 52
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (29)..(30)
<223> OTHER INFORMATION: Variable amino acid
<220> FEATURE:
<221> NAME/KEY: MOD_RES
<222> LOCATION: (37)..(37)
<223> OTHER INFORMATION: Variable amino acid
<220> FEATURE:
<221> NAME/KEY: MOD_RES
<222> LOCATION: (43)..(44)
<223> OTHER INFORMATION: Variable amino acid

<400> SEQUENCE: 39

Ser Xaa Val Gly Ser Arg Cys Gln Tyr Met Arg Gly Leu Val Arg Gln
1               5                   10                  15

Thr Xaa Met Leu Phe Ala Asp Ser His Ile Val Ala Xaa Xaa Met Ile
            20                  25                  30

Arg Tyr Asp Leu Xaa Ser Leu Ile Met Asn Xaa Xaa Arg Asp Ala Asn
            35                  40                  45

Glu Ile Arg Leu
        50
```

-continued

```
<210> SEQ ID NO 40
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Variable amino acid

<400> SEQUENCE: 40

Trp Asn Lys Arg Leu Xaa Leu Gln Gln Ala Asn Glu Gly Phe
1               5                   10

<210> SEQ ID NO 41
<211> LENGTH: 32
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Variable amino acid

<400> SEQUENCE: 41

Ser Arg Ser Leu Arg Arg Arg Glu Thr Val Asp Leu Glu Asp Gln Gly
1               5                   10                  15

Leu Gln Glu Glu Val Ala Thr Thr Gly Leu Xaa Phe Arg Leu Arg Ser
            20                  25                  30

<210> SEQ ID NO 42
<211> LENGTH: 91
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (58)..(58)
<223> OTHER INFORMATION: Variable amino acid
<220> FEATURE:
<221> NAME/KEY: MOD_RES
<222> LOCATION: (63)..(63)
<223> OTHER INFORMATION: Variable amino acid
<220> FEATURE:
<221> NAME/KEY: MOD_RES
<222> LOCATION: (66)..(66)
<223> OTHER INFORMATION: Variable amino acid

<400> SEQUENCE: 42

Tyr Xaa Leu Val Leu Xaa Val Ile Pro Leu Ser Cys Trp Met Ala Gln
1               5                   10                  15

Lys Cys Leu Asp Leu Phe Ile Pro Thr Gly Gln Thr Arg Arg Leu Ala
            20                  25                  30

Leu Trp Pro Trp Asp Cys Gly Ala Val Trp Pro His Ile Leu His Ser
        35                  40                  45

Val Tyr Ser His Pro Asn Leu Ser Leu Xaa Thr Thr Gln Ala Xaa Thr
    50                  55                  60

Asp Xaa Val Val Gln Asp Lys Glu Gly Ala Gln Val Gly Glu Met Glu
65                  70                  75                  80

Ala Glu Met Val His Cys Val Pro Thr Ser Leu
                85                  90
```

-continued

```
<210> SEQ ID NO 43
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Variable amino acid

<400> SEQUENCE: 43

Phe Asn Xaa Leu Asp
1               5

<210> SEQ ID NO 44
<211> LENGTH: 4
<212> TYPE: PRT
<213> ORGANISM: Homo sapiens

<400> SEQUENCE: 44

Asn Pro Asp Pro
1

<210> SEQ ID NO 45
<211> LENGTH: 13
<212> TYPE: PRT
<213> ORGANISM: Homo sapiens

<400> SEQUENCE: 45

Gly Glu Glu Pro Ala Lys Asp Gly Ser Gly Arg Gln Cys
1               5                   10

<210> SEQ ID NO 46
<211> LENGTH: 20
<212> TYPE: PRT
<213> ORGANISM: Homo sapiens

<400> SEQUENCE: 46

Gly Lys Ala Pro Ala Gly Leu Cys Ser Trp Thr Ser Phe Ser Pro Ile
1               5                   10                  15

Ala Arg Ile Ser
            20

<210> SEQ ID NO 47
<211> LENGTH: 11
<212> TYPE: PRT
<213> ORGANISM: Homo sapiens

<400> SEQUENCE: 47

Leu Phe Pro Leu Ser Leu Cys Leu Glu Ser Ser
1               5                   10

<210> SEQ ID NO 48
<211> LENGTH: 27
<212> TYPE: PRT
<213> ORGANISM: Homo sapiens

<400> SEQUENCE: 48

Glu Phe Val Thr Gly Asp Arg Ile Leu Phe Leu Ser Leu Leu Ala Arg
1               5                   10                  15

Tyr Leu Lys Gly Gly Gly Trp Val Thr Phe Trp
            20                  25

<210> SEQ ID NO 49
<211> LENGTH: 10
<212> TYPE: PRT
```

```
<213> ORGANISM: Homo sapiens

<400> SEQUENCE: 49

Gly Lys Leu Lys Leu Trp Ile Ala Lys Cys
1               5                   10

<210> SEQ ID NO 50
<211> LENGTH: 75
<212> TYPE: PRT
<213> ORGANISM: Homo sapiens

<400> SEQUENCE: 50

Leu Tyr Ser Phe Phe Leu Lys Pro His Val Ala Phe Phe Pro Ser
1               5                   10                  15

Thr Leu His Thr Phe Pro Gly Phe Ile Ser Cys Pro Ala Ser Leu Arg
                20                  25                  30

Ser His Arg Cys Arg Leu Phe Glu Ala Ser Pro Leu Gly Leu Pro Gln
            35                  40                  45

Gln Thr Ala Ser Thr Leu Ser Ser Phe Cys Val His Val Asp Ile Arg
    50                  55                  60

Val Ser Phe Pro Thr Trp Leu Leu Leu Phe Leu
65                  70                  75

<210> SEQ ID NO 51
<211> LENGTH: 21
<212> TYPE: PRT
<213> ORGANISM: Homo sapiens

<400> SEQUENCE: 51

Leu Pro Arg Leu Met Pro Cys Leu Ala Ser Ser Cys Lys Tyr Cys Thr
1               5                   10                  15

Met Ile Leu Cys Lys
            20

<210> SEQ ID NO 52
<211> LENGTH: 15
<212> TYPE: PRT
<213> ORGANISM: Homo sapiens

<400> SEQUENCE: 52

Leu Val Leu Ala His Arg Ala Ser Lys Pro Ser Arg Leu Thr Asn
1               5                   10                  15

<210> SEQ ID NO 53
<211> LENGTH: 30
<212> TYPE: PRT
<213> ORGANISM: Homo sapiens

<400> SEQUENCE: 53

Arg Ser Ser Leu Leu Thr Asp Phe Phe Ile Gln Phe Lys Met Ala Gly
1               5                   10                  15

Gly Gly Val Gly Gly Arg Ile Ala Cys Phe His Cys Gly Thr
            20                  25                  30

<210> SEQ ID NO 54
<211> LENGTH: 5
<212> TYPE: PRT
<213> ORGANISM: Homo sapiens

<400> SEQUENCE: 54

Ala Gly Leu Lys Leu
1               5
```

<210> SEQ ID NO 55
<211> LENGTH: 4
<212> TYPE: PRT
<213> ORGANISM: Homo sapiens

<400> SEQUENCE: 55

Ala Pro Leu Leu
1

<210> SEQ ID NO 56
<211> LENGTH: 24
<212> TYPE: PRT
<213> ORGANISM: Homo sapiens

<400> SEQUENCE: 56

Pro Thr Val Ser Val Thr Val Ser Ser Cys Ser Leu Thr Ser Gly Leu
1               5                   10                  15

Ser Trp Ser Gly His Cys Lys Pro
            20

<210> SEQ ID NO 57
<211> LENGTH: 20
<212> TYPE: PRT
<213> ORGANISM: Homo sapiens

<400> SEQUENCE: 57

Leu Ser Asp Cys Gly Trp Leu Ser Leu Ala Leu Ala Ala Asn Met Val
1               5                   10                  15

Thr Gly Phe His
            20

<210> SEQ ID NO 58
<211> LENGTH: 12
<212> TYPE: PRT
<213> ORGANISM: Homo sapiens

<400> SEQUENCE: 58

Lys Phe Lys Cys Trp Gly Lys Gly Ala Asp Thr Pro
1               5                   10

<210> SEQ ID NO 59
<211> LENGTH: 13
<212> TYPE: PRT
<213> ORGANISM: Homo sapiens

<400> SEQUENCE: 59

Trp Ser Gln Phe Lys Thr Ile Arg Glu Thr Ala Ser Ser
1               5                   10

<210> SEQ ID NO 60
<211> LENGTH: 31
<212> TYPE: PRT
<213> ORGANISM: Homo sapiens

<400> SEQUENCE: 60

Asp Val Phe Asn Gln Ser Asn Tyr Leu Asp Thr Thr Lys His Thr Cys
1               5                   10                  15

Leu Gln Ala Val Thr Pro Gln Lys Leu Leu Asp Thr Gln Gln Ala
            20                  25                  30

<210> SEQ ID NO 61
<211> LENGTH: 34

```
<212> TYPE: PRT
<213> ORGANISM: Homo sapiens

<400> SEQUENCE: 61

Leu Ser Gly Leu Ala Arg Ser His Ser Arg Thr Ala Leu His Thr Val
1               5                   10                  15

Gly Arg Lys Met Leu Leu Ser Leu Leu Ser Ala Val Ile Leu His Ile
            20                  25                  30

Pro Cys

<210> SEQ ID NO 62
<211> LENGTH: 6
<212> TYPE: PRT
<213> ORGANISM: Homo sapiens

<400> SEQUENCE: 62

Gly Lys Lys Tyr Cys Leu
1               5

<210> SEQ ID NO 63
<211> LENGTH: 14
<212> TYPE: PRT
<213> ORGANISM: Homo sapiens

<400> SEQUENCE: 63

Val Leu Leu Ser Val Pro Asn Trp Arg Lys Leu Leu Asn Lys
1               5                   10

<210> SEQ ID NO 64
<211> LENGTH: 16
<212> TYPE: PRT
<213> ORGANISM: Homo sapiens

<400> SEQUENCE: 64

Thr Val His Lys Ser Ser Leu Arg Lys Gly Gln Asn Leu Cys Phe Leu
1               5                   10                  15

<210> SEQ ID NO 65
<211> LENGTH: 16
<212> TYPE: PRT
<213> ORGANISM: Homo sapiens

<400> SEQUENCE: 65

Ile Leu Ala Glu Ala Ser Arg Gly Gln His Gln Gly Arg Glu Leu Asp
1               5                   10                  15

<210> SEQ ID NO 66
<211> LENGTH: 78
<212> TYPE: PRT
<213> ORGANISM: Homo sapiens

<400> SEQUENCE: 66

Gly Cys Ser Val Phe Leu Ser Trp Ala Pro His Ser Ser Leu Pro Pro
1               5                   10                  15

Pro Leu Pro Phe His Pro Thr Leu Phe Leu Ala Ala Ser Gly Arg Gly
            20                  25                  30

Gln Asp Arg Arg Glu Ser Asn Glu Asn Ser Gly Leu Gly Gln Ser
        35                  40                  45

Asn Ser Glu Pro Leu Gly Leu Asp Arg Thr Ser Ala His Gly Val Ser
    50                  55                  60

Leu His Pro Ser Pro Ala Pro Ala Pro Gly Val Ala Asp Arg
65                  70                  75
```

<210> SEQ ID NO 67
<211> LENGTH: 23
<212> TYPE: PRT
<213> ORGANISM: Homo sapiens

<400> SEQUENCE: 67

Gly Lys Gln Thr Trp Phe Leu Leu Gly Met Glu Val Met Trp Ile Val
1               5                   10                  15

Tyr Asn Trp Asp His Tyr Gly
            20

<210> SEQ ID NO 68
<211> LENGTH: 9
<212> TYPE: PRT
<213> ORGANISM: Homo sapiens

<400> SEQUENCE: 68

Asn Leu Ala Gly Ala Gln Val Gly Gly
1               5

<210> SEQ ID NO 69
<211> LENGTH: 12
<212> TYPE: PRT
<213> ORGANISM: Homo sapiens

<400> SEQUENCE: 69

Tyr Arg Cys Tyr Ile Ser Cys Val His Ser Cys Ser
1               5                   10

<210> SEQ ID NO 70
<211> LENGTH: 24
<212> TYPE: PRT
<213> ORGANISM: Homo sapiens

<400> SEQUENCE: 70

Thr Pro Lys Trp Gln Trp Pro Lys Leu Pro Leu Ala Cys Thr Ser Leu
1               5                   10                  15

Ser Lys Pro Leu Tyr Leu Ile Ile
            20

<210> SEQ ID NO 71
<211> LENGTH: 41
<212> TYPE: PRT
<213> ORGANISM: Homo sapiens

<400> SEQUENCE: 71

Asn Leu Gly Pro Lys Leu His Arg His Glu Gly Thr Glu Lys Arg Arg
1               5                   10                  15

Val Ser His Leu Pro Phe Gly Tyr Thr Asp Ser Tyr Leu Pro Cys Phe
            20                  25                  30

Ser Leu Pro Leu Val Leu Leu Gly Ala
        35                  40

<210> SEQ ID NO 72
<211> LENGTH: 14
<212> TYPE: PRT
<213> ORGANISM: Homo sapiens

<400> SEQUENCE: 72

Gly Ile Ile Ala Leu Leu Cys Gly Gln Asn Ser Gly Phe Ala
1               5                   10

<210> SEQ ID NO 73
<211> LENGTH: 16
<212> TYPE: PRT
<213> ORGANISM: Homo sapiens

<400> SEQUENCE: 73

Arg Pro Ser Tyr Ser Phe Trp Ser His Ser Pro Ala Asn Phe Leu Asp
1               5                   10                  15

<210> SEQ ID NO 74
<211> LENGTH: 6
<212> TYPE: PRT
<213> ORGANISM: Homo sapiens

<400> SEQUENCE: 74

Lys Lys Lys Ala His Ile
1               5

<210> SEQ ID NO 75
<211> LENGTH: 11
<212> TYPE: PRT
<213> ORGANISM: Homo sapiens

<400> SEQUENCE: 75

Asn Thr Phe Ser Glu Asn Glu His Ser Val Ser
1               5                   10

<210> SEQ ID NO 76
<211> LENGTH: 34
<212> TYPE: PRT
<213> ORGANISM: Homo sapiens

<400> SEQUENCE: 76

Ile Leu Gly Asp Gly Gly Leu Leu Gly Cys Lys Glu Gln Asp Ser Arg
1               5                   10                  15

Glu Glu Asn His Gly Arg Asp Lys Arg Leu Glu Phe Phe Pro Ala Ser
            20                  25                  30

Ala Leu

<210> SEQ ID NO 77
<211> LENGTH: 21
<212> TYPE: PRT
<213> ORGANISM: Homo sapiens

<400> SEQUENCE: 77

Ser Leu Phe Pro Lys Ile Thr Ala Leu Ile Leu Trp Glu Leu Gly Ser
1               5                   10                  15

Gly Glu Arg Asn Gln
            20

<210> SEQ ID NO 78
<211> LENGTH: 11
<212> TYPE: PRT
<213> ORGANISM: Homo sapiens

<400> SEQUENCE: 78

Ala Gln Met Gly Pro Gln Ala Trp Thr Lys Val
1               5                   10

<210> SEQ ID NO 79
<211> LENGTH: 15
<212> TYPE: PRT
<213> ORGANISM: Homo sapiens

<400> SEQUENCE: 79

Gly Asn Tyr Gly Ser Arg Gln Gly Val Phe Val Arg Trp Met Arg
1               5                   10                  15

<210> SEQ ID NO 80
<211> LENGTH: 10
<212> TYPE: PRT
<213> ORGANISM: Homo sapiens

<400> SEQUENCE: 80

Gly Asp Cys Gly Gly Gly Glu Ser Trp Gly
1               5                   10

<210> SEQ ID NO 81
<211> LENGTH: 15
<212> TYPE: PRT
<213> ORGANISM: Homo sapiens

<400> SEQUENCE: 81

Met Ala Asn Cys Val Trp Ala Gly Arg Trp Phe His Pro Leu Asn
1               5                   10                  15

<210> SEQ ID NO 82
<211> LENGTH: 18
<212> TYPE: PRT
<213> ORGANISM: Homo sapiens

<400> SEQUENCE: 82

Gly Trp Gln Gly Trp Lys Glu Pro Ala Leu Ser Thr Leu Glu Lys Val
1               5                   10                  15

Gln Val

<210> SEQ ID NO 83
<211> LENGTH: 32
<212> TYPE: PRT
<213> ORGANISM: Homo sapiens

<400> SEQUENCE: 83

Gln Glu Glu Thr Glu Arg Gly Asp Thr Arg Ala Gly Ser Ser Leu Pro
1               5                   10                  15

Ser Phe Leu Pro Met Ala Leu Ala Leu Gly Arg Ile Arg Lys Gly Trp
                20                  25                  30

<210> SEQ ID NO 84
<211> LENGTH: 31
<212> TYPE: PRT
<213> ORGANISM: Homo sapiens

<400> SEQUENCE: 84

Leu Cys Ile Leu Arg Lys Ala Leu Ser Pro Ser Leu Asp Ser Arg Gly
1               5                   10                  15

Leu Glu Arg Arg Met Cys Arg Arg Asn Asp Val Glu Arg Val Thr
                20                  25                  30

<210> SEQ ID NO 85
<211> LENGTH: 6
<212> TYPE: PRT
<213> ORGANISM: Homo sapiens

<400> SEQUENCE: 85

Pro Ile Gln Met Cys Leu
1               5

<210> SEQ ID NO 86
<211> LENGTH: 5
<212> TYPE: PRT
<213> ORGANISM: Homo sapiens

<400> SEQUENCE: 86

Met Arg Phe Gln Glu
1               5

<210> SEQ ID NO 87
<211> LENGTH: 36
<212> TYPE: PRT
<213> ORGANISM: Homo sapiens

<400> SEQUENCE: 87

Glu Trp Lys Tyr Ser Cys Ala Ser Ala Trp Pro Arg Ala Leu Gly Ser
1               5                   10                  15

Leu Thr Pro Thr Pro Gln Glu Glu Asn His Pro Ile Ile Pro Pro Gly
            20                  25                  30

Val Leu Arg Thr
            35

<210> SEQ ID NO 88
<211> LENGTH: 7
<212> TYPE: PRT
<213> ORGANISM: Homo sapiens

<400> SEQUENCE: 88

His Arg Ala Gly Glu Leu Arg
1               5

<210> SEQ ID NO 89
<211> LENGTH: 111
<212> TYPE: PRT
<213> ORGANISM: Homo sapiens

<400> SEQUENCE: 89

Lys His Ser Leu Leu Ser Cys Leu Pro Leu Ser Leu Thr Ser Pro Ser
1               5                   10                  15

Leu Thr Asp Trp Trp Met Leu Ile Met Ile Leu Thr Pro Gln Val Ser
            20                  25                  30

Ala Pro Pro Leu Ile Trp Met Asn Thr Thr His Asp Ser Ser Gln Gly
        35                  40                  45

His Gln Arg Pro Asn Leu Asp Thr Val Ser Tyr Ser Met Leu Gly Val
50                  55                  60

Asp Ser Asp Gly Glu Arg Glu Asn Arg Gly Pro Trp Asp Arg Asp Tyr
65                  70                  75                  80

Ala Leu Thr Asp Lys Gly Glu Asp Arg Ser Lys Leu Ala Phe Glu Ser
                85                  90                  95

Ala Trp Gly Ser Met Thr Ser His Ala Leu Ser Leu Ser Leu Tyr
            100                 105                 110

<210> SEQ ID NO 90
<211> LENGTH: 37
<212> TYPE: PRT
<213> ORGANISM: Homo sapiens

<400> SEQUENCE: 90

Gly Pro Cys Ser Pro Asp Leu Tyr Ile His Ile Leu Leu Pro Gly Cys
1               5                   10                  15

Trp Trp Val Pro Pro Gly Met Gly His Gln Val Thr Gly Glu Gly Met
            20                  25                  30

Phe Ile Val Ala Leu
        35

<210> SEQ ID NO 91
<211> LENGTH: 29
<212> TYPE: PRT
<213> ORGANISM: Homo sapiens

<400> SEQUENCE: 91

Gly Asp Ser Thr Val Leu His Val Pro Lys Ala Thr Trp Val Arg Arg
1               5                   10                  15

Ser Leu Thr Phe Pro Leu Leu Ile Pro Asp Val Asp Ile
            20                  25

<210> SEQ ID NO 92
<211> LENGTH: 7
<212> TYPE: PRT
<213> ORGANISM: Homo sapiens

<400> SEQUENCE: 92

Pro Leu Gly Pro Cys Leu Gln
1               5

<210> SEQ ID NO 93
<211> LENGTH: 6
<212> TYPE: PRT
<213> ORGANISM: Homo sapiens

<400> SEQUENCE: 93

Thr Lys Glu Ala Glu Leu
1               5

<210> SEQ ID NO 94
<211> LENGTH: 25
<212> TYPE: PRT
<213> ORGANISM: Homo sapiens

<400> SEQUENCE: 94

Pro His Asp Phe Ile Leu Phe Tyr Pro Ser Ser Asn Gln Val Thr Ile
1               5                   10                  15

Asn Leu Glu Ile Pro Leu Ser Leu Leu
            20                  25

<210> SEQ ID NO 95
<211> LENGTH: 4
<212> TYPE: PRT
<213> ORGANISM: Homo sapiens

<400> SEQUENCE: 95

Gly Cys Leu Tyr
1

<210> SEQ ID NO 96
<211> LENGTH: 9
<212> TYPE: PRT
<213> ORGANISM: Homo sapiens

<400> SEQUENCE: 96

Arg Gln Met Leu Met Gly Asp Ser Trp
1               5

<210> SEQ ID NO 97
<211> LENGTH: 76
<212> TYPE: PRT
<213> ORGANISM: Homo sapiens

<400> SEQUENCE: 97

Ala Glu Arg Arg Ala Ser Glu Gly Ser Gln Gln Gly Arg Glu His Tyr
1               5                   10                  15

Gly Ile Trp Ala Val Val Ala Trp Ala Phe His Pro Ser Val Leu Glu
            20                  25                  30

Ala Glu Ser Gly Leu Ile Tyr Arg Val Ser Ser Arg Thr Ala Lys Ala
        35                  40                  45

Met Gln Arg Asn Pro Val Leu Lys Asn Pro Lys Pro Lys Leu Thr Lys
50                  55                  60

Gln Gln Gln Gln Lys Lys His Arg Gly Lys Gly Asn
65                  70                  75

<210> SEQ ID NO 98
<211> LENGTH: 84
<212> TYPE: PRT
<213> ORGANISM: Homo sapiens

<400> SEQUENCE: 98

Lys Arg Gln Gly Ile Gln Asn Pro Arg Glu Gln Gly Arg Val Pro His
1               5                   10                  15

Gly Val Val Ser Ile Ser Leu Leu Thr Arg Cys Val Phe Arg Glu Ala
            20                  25                  30

Leu Ser Ser Leu Gly Ile Thr Ile Ser Pro Ile His Pro Gly Leu Cys
        35                  40                  45

Pro Ser Leu Val Ser Cys Leu Arg Gln Leu Cys Leu Gln Phe Trp Asn
50                  55                  60

Met Cys Pro Cys Gly Cys Phe Ile Pro Ala Pro Gly Lys Pro Gly Thr
65                  70                  75                  80

His Arg Pro Thr

<210> SEQ ID NO 99
<211> LENGTH: 46
<212> TYPE: PRT
<213> ORGANISM: Homo sapiens

<400> SEQUENCE: 99

Ala Ser Gly Arg Ala Leu Glu Ala Gln Phe Pro Asp Arg Asp Ala Gly
1               5                   10                  15

Trp Glu Lys Leu Gly Gln Arg Leu Gly Gly Ser Ala Trp Leu Ser
            20                  25                  30

Ser Ser Phe Pro Ser Val Leu Ala Glu Glu Ala Pro Val Cys
        35                  40                  45

<210> SEQ ID NO 100
<211> LENGTH: 7
<212> TYPE: PRT
<213> ORGANISM: Homo sapiens

<400> SEQUENCE: 100

Leu Ile Arg Ile Gln Thr Pro
1               5

<210> SEQ ID NO 101
<211> LENGTH: 41

<212> TYPE: PRT
<213> ORGANISM: Homo sapiens

<400> SEQUENCE: 101

Glu Ser Leu Lys Thr Pro Gly Ser Gly Phe Thr Asn Leu Lys Thr Lys
1               5                   10                  15

Gln Asn Ser Ile Ser Cys Ala Gln Pro Ile Pro His Pro Ser Arg Val
            20                  25                  30

Leu His Ile Leu Phe Leu Trp Val Leu
        35                  40

<210> SEQ ID NO 102
<211> LENGTH: 26
<212> TYPE: PRT
<213> ORGANISM: Homo sapiens

<400> SEQUENCE: 102

Met Pro Ser Gln His Ser Val Ile Gly Phe Ser Pro His Ala Phe His
1               5                   10                  15

Ile Leu Ser Tyr Leu Leu Pro Phe Gly Arg
            20                  25

<210> SEQ ID NO 103
<211> LENGTH: 45
<212> TYPE: PRT
<213> ORGANISM: Homo sapiens

<400> SEQUENCE: 103

Ser Tyr Val Ala Gln Ala Val Leu Asp Leu Gly Ile Cys Leu Pro Gln
1               5                   10                  15

Leu Leu Ser Leu Lys Tyr Trp Asp Asn Arg His Ala Leu Ser Ala Trp
            20                  25                  30

Pro Leu Leu Asn Met Pro Ser Val Ala Ile Gly Arg Ala
        35                  40                  45

<210> SEQ ID NO 104
<211> LENGTH: 14
<212> TYPE: PRT
<213> ORGANISM: Homo sapiens

<400> SEQUENCE: 104

Val Lys Tyr Cys Pro Pro Gln His Thr His Lys Arg Lys
1               5                   10

<210> SEQ ID NO 105
<211> LENGTH: 6
<212> TYPE: PRT
<213> ORGANISM: Homo sapiens

<400> SEQUENCE: 105

Gly Ser Leu Ser Val Pro
1               5

<210> SEQ ID NO 106
<211> LENGTH: 23
<212> TYPE: PRT
<213> ORGANISM: Homo sapiens

<400> SEQUENCE: 106

His Arg Val Val Val Gly Leu Ser Leu Val His Ile Ser Phe Phe Tyr
1               5                   10                  15

Ser Ala His Leu Phe Phe Leu

```
                    20

<210> SEQ ID NO 107
<211> LENGTH: 12
<212> TYPE: PRT
<213> ORGANISM: Homo sapiens

<400> SEQUENCE: 107

Phe Pro His Trp Gly Pro Gly Ile Val Leu Ser Trp
1               5                   10

<210> SEQ ID NO 108
<211> LENGTH: 21
<212> TYPE: PRT
<213> ORGANISM: Homo sapiens

<400> SEQUENCE: 108

Leu Arg Glu Asn Ser Leu Leu Ser Ala Cys Ile Ala Ala Ser Ser Trp
1               5                   10                  15

Asp Ile Leu Pro Cys
            20

<210> SEQ ID NO 109
<211> LENGTH: 68
<212> TYPE: PRT
<213> ORGANISM: Homo sapiens

<400> SEQUENCE: 109

Leu His Pro Thr Ser Phe His Val Phe Cys Phe Pro Ser Leu Cys Pro
1               5                   10                  15

Pro Ser Arg Leu Ser His Ile His Gly Cys Arg His Cys Phe Gly Trp
            20                  25                  30

Leu Gln Gln Tyr Leu Ser Leu Val Arg Ser Ser Asp Phe Pro Ser Glu
        35                  40                  45

Ala Gly Arg Lys Thr Val His Arg Ser Gly Ala Asp Thr Gly Lys Arg
    50                  55                  60

Lys Ile Cys Gly
 65

<210> SEQ ID NO 110
<211> LENGTH: 21
<212> TYPE: PRT
<213> ORGANISM: Homo sapiens

<400> SEQUENCE: 110

Asp Trp Arg Glu Arg Ser Lys His Ser Trp Thr Leu Gly Cys Lys Gln
1               5                   10                  15

Pro Cys Pro Ala Ser
            20

<210> SEQ ID NO 111
<211> LENGTH: 33
<212> TYPE: PRT
<213> ORGANISM: Homo sapiens

<400> SEQUENCE: 111

His Pro Gly Thr Leu Ser Ser Thr Glu Leu Met Leu Lys Asn Cys Ala
1               5                   10                  15

Ile Asn Leu Pro Lys Ser His Lys Asn Phe Ile Met Phe Glu Val Ser
            20                  25                  30

Leu
```

<210> SEQ ID NO 112
<211> LENGTH: 123
<212> TYPE: PRT
<213> ORGANISM: Homo sapiens

<400> SEQUENCE: 112

Leu Cys Gly Gly Pro His Ser Glu Leu Pro Phe Ala Ala Cys Ser Cys
1               5                   10                  15

Leu Gly Asn Ala Cys His Glu Leu Gln Val Arg His Thr Cys Ser Leu
            20                  25                  30

Pro Leu His Arg Ala Ala Gly Trp Thr His Leu Leu Gly Val His Phe
        35                  40                  45

Pro Phe Ile Leu Cys Ala Pro Ser Ser Leu Arg Ser Ser Tyr Ile Pro
    50                  55                  60

Cys Gly His Met Val Tyr Cys Ser Gln Val Gly Leu Val Gln Tyr Gly
65                  70                  75                  80

Glu Asn Pro Val His Glu Trp Ser Leu Gly Asp Phe Arg Thr Lys Glu
                85                  90                  95

Glu Val Val Arg Ala Ala Arg Asn Leu Ser Arg Arg Glu Gly Arg Glu
            100                 105                 110

Thr Arg Thr Ala Gln Ala Ile Met Val Ala Trp
        115                 120

<210> SEQ ID NO 113
<211> LENGTH: 91
<212> TYPE: PRT
<213> ORGANISM: Homo sapiens

<400> SEQUENCE: 113

Asp Ile Val Lys Gly Ser Cys Glu Gly Gly Arg Ile Ser Arg Glu
1               5                   10                  15

Arg Glu Arg Val Trp Ser Val Val Tyr Thr Ser Gln Asp Ala Leu Gly
            20                  25                  30

Ala Tyr Leu Tyr Leu His Ala Arg Ser Ser Trp Arg Lys Ala Arg Leu
        35                  40                  45

Leu Ser Pro Tyr Ser Leu Leu Leu Tyr Leu His Phe Met Val Ser Val
    50                  55                  60

Gly Val Ser Leu Leu Val Cys Ser Val Ser Ala His Arg Thr Pro Ser
65                  70                  75                  80

Phe Leu Phe Tyr Ser Cys Val Asn Ser Asp Thr
                85                  90

<210> SEQ ID NO 114
<211> LENGTH: 40
<212> TYPE: PRT
<213> ORGANISM: Homo sapiens

<400> SEQUENCE: 114

Leu Leu Asn His Ser Arg Pro Ser Ile Leu Phe Lys His Asp Ser Lys
1               5                   10                  15

Pro Leu Gly Arg Leu His Asp Leu Thr Val Phe Ile Leu Gln Phe Leu
            20                  25                  30

Asp Leu Val Asn Pro Ser Val Cys
        35                  40

<210> SEQ ID NO 115
<211> LENGTH: 9

```
<212> TYPE: PRT
<213> ORGANISM: Homo sapiens

<400> SEQUENCE: 115

Ile Asn Asn Ala Cys Thr Tyr Leu His
1               5

<210> SEQ ID NO 116
<211> LENGTH: 22
<212> TYPE: PRT
<213> ORGANISM: Homo sapiens

<400> SEQUENCE: 116

Gln Ile Ile Leu Tyr Val Pro Cys His Leu Asn Ser Gln Val Val Thr
1               5                   10                  15

Leu Cys Gln Phe Ala Cys
            20

<210> SEQ ID NO 117
<211> LENGTH: 10
<212> TYPE: PRT
<213> ORGANISM: Homo sapiens

<400> SEQUENCE: 117

Ile Leu Leu Gly Asn Gly Val Glu Asp Ile
1               5                   10

<210> SEQ ID NO 118
<211> LENGTH: 29
<212> TYPE: PRT
<213> ORGANISM: Homo sapiens

<400> SEQUENCE: 118

Thr Ala Asp Ser Val Asn Thr Leu Tyr Gly His Ala Cys Met Gln Ala
1               5                   10                  15

Cys Val Tyr Val Cys His Ala Tyr Ala His Thr Tyr Ile
            20                  25

<210> SEQ ID NO 119
<211> LENGTH: 29
<212> TYPE: PRT
<213> ORGANISM: Homo sapiens

<400> SEQUENCE: 119

Pro Tyr Ser Ile Leu Leu Ser Leu Phe Leu Ala Gln Lys Gly Ser Val
1               5                   10                  15

Ser Pro Gly Gly Asp Asp Gln Arg Pro Leu Gly Cys Trp
            20                  25

<210> SEQ ID NO 120
<211> LENGTH: 16
<212> TYPE: PRT
<213> ORGANISM: Homo sapiens

<400> SEQUENCE: 120

Leu Ser Leu Met Glu Ser Pro Met Met Glu Arg Asn Phe Gln Gln Arg
1               5                   10                  15

<210> SEQ ID NO 121
<211> LENGTH: 7
<212> TYPE: PRT
<213> ORGANISM: Homo sapiens

<400> SEQUENCE: 121
```

Arg Pro Val Arg Leu Ala Glu
1               5

<210> SEQ ID NO 122
<211> LENGTH: 6
<212> TYPE: PRT
<213> ORGANISM: Homo sapiens

<400> SEQUENCE: 122

His Val Met Gly Leu Arg
1               5

<210> SEQ ID NO 123
<211> LENGTH: 30
<212> TYPE: PRT
<213> ORGANISM: Homo sapiens

<400> SEQUENCE: 123

Asp Leu Ile Lys Ser Ser Cys Phe Val Leu Cys Cys Ile Cys Val
1               5                  10                  15

Cys Val Cys Val Cys Val Cys Val Cys Val Cys Val Tyr Val
            20                  25                  30

<210> SEQ ID NO 124
<211> LENGTH: 46
<212> TYPE: PRT
<213> ORGANISM: Homo sapiens

<400> SEQUENCE: 124

Tyr Val Cys Met His Gln Cys Thr Tyr His Ser Val Tyr Met Arg Val
1               5                   10                  15

Arg Glu Gln Pro Gln Met Leu Val Leu Thr Phe His Leu Val Pro Asn
            20                  25                  30

Trp Ile Ser Cys Ser Leu Arg His Thr Ile Ser Gln Ile Ser
        35                  40                  45

<210> SEQ ID NO 125
<211> LENGTH: 24
<212> TYPE: PRT
<213> ORGANISM: Homo sapiens

<400> SEQUENCE: 125

Pro Thr Ser Leu Gly Gln Val Phe Cys Leu Ser Leu Ser Leu Gly
1               5                   10                  15

Leu Arg His Ser Gly Ile Tyr Arg
            20

<210> SEQ ID NO 126
<211> LENGTH: 10
<212> TYPE: PRT
<213> ORGANISM: Homo sapiens

<400> SEQUENCE: 126

Tyr Arg Ile Pro Ala Ala Arg Gly Ile His
1               5                   10

<210> SEQ ID NO 127
<211> LENGTH: 7
<212> TYPE: PRT
<213> ORGANISM: Homo sapiens

<400> SEQUENCE: 127

Ser Gly Arg His Gln Gly Ser
1               5

<210> SEQ ID NO 128
<211> LENGTH: 28
<212> TYPE: PRT
<213> ORGANISM: Homo sapiens
<220> FEATURE:
<221> NAME/KEY: MOD_RES
<222> LOCATION: (1)..(3)
<223> OTHER INFORMATION: Variable amino acid
<220> FEATURE:
<221> NAME/KEY: MOD_RES
<222> LOCATION: (5)..(8)
<223> OTHER INFORMATION: Variable amino acid
<220> FEATURE:
<221> NAME/KEY: MOD_RES
<222> LOCATION: (10)..(13)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (20)..(21)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid

<400> SEQUENCE: 128

Xaa Xaa Xaa His Xaa Xaa Xaa Xaa Arg Xaa Xaa Xaa Xaa Val Thr Xaa
1               5                   10                  15

Leu Xaa Lys Xaa Xaa Ser Met Thr Xaa Gly Pro Arg
            20                  25

<210> SEQ ID NO 129
<211> LENGTH: 36
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(7)
<223> OTHER INFORMATION: Variable amino acid
<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (15)..(18)
<223> OTHER INFORMATION: Variable amino acid
<220> FEATURE:
<221> NAME/KEY: MOD_RES
<222> LOCATION: (20)..(21)
<223> OTHER INFORMATION: Variable amino acid
<220> FEATURE:
<221> NAME/KEY: MOD_RES
<222> LOCATION: (24)..(27)
<223> OTHER INFORMATION: Variable amino acid
<220> FEATURE:
<221> NAME/KEY: MOD_RES
<222> LOCATION: (30)..(30)
<223> OTHER INFORMATION: Variable amino acid
<220> FEATURE:

-continued

```
<221> NAME/KEY: MOD_RES
<222> LOCATION: (32)..(32)
<223> OTHER INFORMATION: Variable amino acid
<220> FEATURE:
<221> NAME/KEY: MOD_RES
<222> LOCATION: (35)..(35)
<223> OTHER INFORMATION: Variable amino acid

<400> SEQUENCE: 129

Xaa Xaa Ser Xaa Xaa Xaa Xaa Asp Asp Gly Pro Ala Xaa Arg Xaa Xaa
1               5                   10                  15

Xaa Xaa Ala Xaa Xaa Val Gln Xaa Xaa Xaa Xaa Gly Thr Xaa Gly Xaa
            20                  25                  30

Ala Arg Xaa Pro
        35

<210> SEQ ID NO 130
<211> LENGTH: 104
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(14)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (23)..(23)
<223> OTHER INFORMATION: Variable amino acid
<220> FEATURE:
<221> NAME/KEY: MOD_RES
<222> LOCATION: (26)..(26)
<223> OTHER INFORMATION: Variable amino acid
<220> FEATURE:
<221> NAME/KEY: MOD_RES
<222> LOCATION: (28)..(31)
<223> OTHER INFORMATION: Variable amino acid
<220> FEATURE:
<221> NAME/KEY: MOD_RES
<222> LOCATION: (33)..(33)
<223> OTHER INFORMATION: Variable amino acid
<220> FEATURE:
<221> NAME/KEY: MOD_RES
<222> LOCATION: (35)..(36)
<223> OTHER INFORMATION: Variable amino acid
<220> FEATURE:
<221> NAME/KEY: MOD_RES
<222> LOCATION: (38)..(42)
<223> OTHER INFORMATION: Variable amino acid
<220> FEATURE:
<221> NAME/KEY: MOD_RES
<222> LOCATION: (47)..(49)
<223> OTHER INFORMATION: Variable amino acid
<220> FEATURE:
<221> NAME/KEY: MOD_RES
<222> LOCATION: (54)..(55)
<223> OTHER INFORMATION: Variable amino acid
<220> FEATURE:
<221> NAME/KEY: MOD_RES
<222> LOCATION: (58)..(58)
```

```
<223> OTHER INFORMATION: Variable amino acid
<220> FEATURE:
<221> NAME/KEY: MOD_RES
<222> LOCATION: (65)..(66)
<223> OTHER INFORMATION: Variable amino acid
<220> FEATURE:
<221> NAME/KEY: MOD_RES
<222> LOCATION: (69)..(71)
<223> OTHER INFORMATION: Variable amino acid
<220> FEATURE:
<221> NAME/KEY: MOD_RES
<222> LOCATION: (73)..(74)
<223> OTHER INFORMATION: Variable amino acid
<220> FEATURE:
<221> NAME/KEY: MOD_RES
<222> LOCATION: (76)..(76)
<223> OTHER INFORMATION: Variable amino acid
<220> FEATURE:
<221> NAME/KEY: MOD_RES
<222> LOCATION: (80)..(80)
<223> OTHER INFORMATION: Variable amino acid
<220> FEATURE:
<221> NAME/KEY: MOD_RES
<222> LOCATION: (82)..(85)
<223> OTHER INFORMATION: Variable amino acid
<220> FEATURE:
<221> NAME/KEY: MOD_RES
<222> LOCATION: (88)..(88)
<223> OTHER INFORMATION: Variable amino acid
<220> FEATURE:
<221> NAME/KEY: MOD_RES
<222> LOCATION: (90)..(90)
<223> OTHER INFORMATION: Variable amino acid
<220> FEATURE:
<221> NAME/KEY: MOD_RES
<222> LOCATION: (92)..(92)
<223> OTHER INFORMATION: Variable amino acid
<220> FEATURE:
<221> NAME/KEY: MOD_RES
<222> LOCATION: (97)..(97)
<223> OTHER INFORMATION: Variable amino acid

<400> SEQUENCE: 130

Gly Ser Gly Thr Met Xaa Xaa Arg Xaa Thr Xaa Xaa Asp Xaa Ser Xaa
1               5                   10                  15

Val Gly Arg Arg Arg Asn Xaa Lys Val Xaa Val Xaa Xaa Xaa Xaa Gly
                20                  25                  30

Xaa Asp Xaa Xaa Thr Xaa Xaa Xaa Xaa Xaa Gly Thr Gly Glu Xaa Xaa
            35                  40                  45

Xaa Val Ser Glu Glu Xaa Xaa Arg Thr Xaa Leu Pro Lys Ser Gly Leu
        50                  55                  60

Xaa Xaa Asp Thr Xaa Xaa Xaa Ser Xaa Xaa Gly Xaa Ser Glu Cys Xaa
65                  70                  75                  80

Asn Xaa Xaa Xaa Xaa Val Tyr Xaa Asn Xaa Lys Xaa Gly His Leu Leu
                85                  90                  95

Xaa Glu Glu Ser Ser Gln Ile Thr
            100

<210> SEQ ID NO 131
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Variable amino acid

<400> SEQUENCE: 131

Asp Asp Leu Xaa Trp Gly Pro Val Ala Ser Ile
1               5                   10
```

```
<210> SEQ ID NO 132
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Variable amino acid

<400> SEQUENCE: 132

Glu Asp Trp Phe Gly Arg His Xaa Cys Ser Leu Leu Thr His Ile Leu
1               5                   10                  15

Leu Pro

<210> SEQ ID NO 133
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Variable amino acid

<400> SEQUENCE: 133

Ser Asp Thr Ile Xaa Cys Pro Ser Ser
1               5

<210> SEQ ID NO 134
<211> LENGTH: 231
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (17)..(17)
<223> OTHER INFORMATION: Variable amino acid
<220> FEATURE:
<221> NAME/KEY: MOD_RES
<222> LOCATION: (48)..(48)
<223> OTHER INFORMATION: Variable amino acid
<220> FEATURE:
<221> NAME/KEY: MOD_RES
<222> LOCATION: (53)..(53)
<223> OTHER INFORMATION: Variable amino acid
<220> FEATURE:
<221> NAME/KEY: MOD_RES
<222> LOCATION: (65)..(65)
<223> OTHER INFORMATION: Variable amino acid
<220> FEATURE:
<221> NAME/KEY: MOD_RES
<222> LOCATION: (118)..(118)
<223> OTHER INFORMATION: Variable amino acid
<220> FEATURE:
<221> NAME/KEY: MOD_RES
<222> LOCATION: (123)..(123)
<223> OTHER INFORMATION: Variable amino acid
<220> FEATURE:
<221> NAME/KEY: MOD_RES
<222> LOCATION: (126)..(126)
<223> OTHER INFORMATION: Variable amino acid
<220> FEATURE:
<221> NAME/KEY: MOD_RES
<222> LOCATION: (144)..(144)
<223> OTHER INFORMATION: Variable amino acid
<220> FEATURE:
<221> NAME/KEY: MOD_RES
<222> LOCATION: (148)..(148)
<223> OTHER INFORMATION: Variable amino acid
<220> FEATURE:
```

```
<221> NAME/KEY: MOD_RES
<222> LOCATION: (155)..(155)
<223> OTHER INFORMATION: Variable amino acid
<220> FEATURE:
<221> NAME/KEY: MOD_RES
<222> LOCATION: (164)..(164)
<223> OTHER INFORMATION: Variable amino acid
<220> FEATURE:
<221> NAME/KEY: MOD_RES
<222> LOCATION: (205)..(205)
<223> OTHER INFORMATION: Variable amino acid

<400> SEQUENCE: 134

Xaa Xaa Ala Val Met Leu Met Arg Phe Ala Tyr Asp Gly Thr Arg Asp
1               5                   10                  15

Xaa Cys Tyr Ser Arg Arg Met Lys Val Ser Arg Val Gly Val Ser Gly
            20                  25                  30

Gly Glu Lys Leu Trp Thr Trp Arg Thr Arg Asp Ser Arg Arg Lys Xaa
        35                  40                  45

Pro Gln Leu Ala Xaa Ser Phe Gly Ser Asp Pro Asp Thr Gly Ser Ser
    50                  55                  60

Xaa Glu Leu Ser Pro Ser Leu Ala Gly Trp Leu Arg Asn Ala Trp Thr
65                  70                  75                  80

Phe Ser Ser Pro Leu Asp Lys Leu Gly Val Trp Arg Cys Gly Pro Gly
                85                  90                  95

Ile Val Gly Leu Cys Gly Leu Ile Ser Ser Ile Leu Ser Ile Leu Thr
            100                 105                 110

Leu Ile Cys Pro Trp Xaa Arg Leu Lys Pro Xaa Leu Thr Xaa Trp Tyr
        115                 120                 125

Lys Ile Arg Arg Glu Pro Arg Trp Val Arg Trp Lys Leu Arg Trp Xaa
130                 135                 140

Thr Val Cys Xaa Pro His Cys Asn Ser Thr Xaa Leu Thr Glu Val Lys
145                 150                 155                 160

Ile Gln Ile Xaa Arg Asp Glu Gly Lys Asn Leu Pro Lys Thr Gly Gln
            165                 170                 175

Glu Gly Ser Ala Lys Gly Arg Leu Leu Gln Ala Ser Ala Val Gly Leu
        180                 185                 190

His Ser Val Pro Leu Pro Glu Ser His Ser Ser Xaa Tyr Leu Ser
    195                 200                 205

Val Leu Ser Leu Val Lys Asn Leu Leu Pro Glu Thr Glu Phe Ser Phe
    210                 215                 220

Leu Ala Ser Trp Pro Asp Ile
225                 230

<210> SEQ ID NO 135
<211> LENGTH: 16
<212> TYPE: PRT
<213> ORGANISM: Homo sapiens

<400> SEQUENCE: 135

Lys Glu Gly Gly Gly Leu Leu Phe Gly Arg Gly Ser Leu Ser Tyr Gly
1               5                   10                  15

<210> SEQ ID NO 136
<211> LENGTH: 9
<212> TYPE: PRT
<213> ORGANISM: Homo sapiens

<400> SEQUENCE: 136

Gln Ser Ala Asn Cys Ile Leu Phe Phe
```

```
<210> SEQ ID NO 137
<211> LENGTH: 69
<212> TYPE: PRT
<213> ORGANISM: Homo sapiens

<400> SEQUENCE: 137

His Phe Ser Ser Leu Pro Pro Ser Ile Leu Ser Gln Ala Phe Ser His
 1               5                  10                  15

Ala Arg Arg Leu Phe Ala His Thr Ala Ala Gly Cys Leu Arg Leu Leu
            20                  25                  30

Pro Trp Val Cys Leu Ser Arg Leu Pro Pro His Phe Pro Val Ser Ala
        35                  40                  45

Tyr Thr Leu Ile Leu Glu Phe Pro Ser Pro Leu Gly Ser Cys Ser Phe
50                  55                  60

Ser Asp Tyr Pro Gly
65

<210> SEQ ID NO 138
<211> LENGTH: 12
<212> TYPE: PRT
<213> ORGANISM: Homo sapiens

<400> SEQUENCE: 138

Cys His Val Trp Pro Leu Pro Val Asn Thr Val Gln
 1               5                  10

<210> SEQ ID NO 139
<211> LENGTH: 17
<212> TYPE: PRT
<213> ORGANISM: Homo sapiens

<400> SEQUENCE: 139

Phe Tyr Val Asn Asn Trp Ser Leu Pro Thr Glu Gln Ala Ser Leu Leu
 1               5                  10                  15

Gly

<210> SEQ ID NO 140
<211> LENGTH: 36
<212> TYPE: PRT
<213> ORGANISM: Homo sapiens

<400> SEQUENCE: 140

Gln Ile Lys Asp Gln Val Cys Ser Leu Thr Phe Leu Phe Asn Ser Arg
 1               5                  10                  15

Trp Arg Gly Val Gly Trp Gly Gly Leu Pro Val Phe Thr Val Val
            20                  25                  30

Pro Arg Gln Gly
        35

<210> SEQ ID NO 141
<211> LENGTH: 14
<212> TYPE: PRT
<213> ORGANISM: Homo sapiens

<400> SEQUENCE: 141

Ser Ser Glu Leu Pro Cys Phe Arg Leu Leu Ser Ser Leu Gln
 1               5                  10

<210> SEQ ID NO 142
```

```
<211> LENGTH: 8
<212> TYPE: PRT
<213> ORGANISM: Homo sapiens

<400> SEQUENCE: 142

Val Leu Leu Cys Pro Ala Ala Arg
1               5

<210> SEQ ID NO 143
<211> LENGTH: 23
<212> TYPE: PRT
<213> ORGANISM: Homo sapiens

<400> SEQUENCE: 143

His Leu Val Ser His Gly Leu Val Ile Val Ser Leu Ser Ser Leu Thr
1               5                   10                  15

Val Asp Gly Phe Pro Trp Arg
            20

<210> SEQ ID NO 144
<211> LENGTH: 58
<212> TYPE: PRT
<213> ORGANISM: Homo sapiens

<400> SEQUENCE: 144

Gln Leu Thr Trp Leu Gln Asp Phe Thr Glu Asn Leu Asn Val Gly Gly
1               5                   10                  15

Lys Val Arg Thr His His Asn Gly Pro Asn Ser Lys Gln Ser Val Lys
            20                  25                  30

Gln Pro Gln Val Arg Gly Glu Met Phe Ser Thr Lys Val Ile Ile Leu
        35                  40                  45

Thr Pro Gln Ser Thr Pro Val Tyr Arg Gln
    50                  55

<210> SEQ ID NO 145
<211> LENGTH: 5
<212> TYPE: PRT
<213> ORGANISM: Homo sapiens

<400> SEQUENCE: 145

Leu Pro Lys Ser Tyr
1               5

<210> SEQ ID NO 146
<211> LENGTH: 23
<212> TYPE: PRT
<213> ORGANISM: Homo sapiens

<400> SEQUENCE: 146

Thr His Asn Lys His Asp His Asn Ser Val Asp Trp Gln Gly His Thr
1               5                   10                  15

Val Gly Leu Pro Phe Thr Gln
            20

<210> SEQ ID NO 147
<211> LENGTH: 40
<212> TYPE: PRT
<213> ORGANISM: Homo sapiens

<400> SEQUENCE: 147

Val Gly Lys Cys Cys Cys His Cys Cys Gln Leu Leu Phe Cys Ile Ser
1               5                   10                  15
```

His Val Lys Ile Asn Lys Ala Lys Asn Ile Val Ser Lys Ser Tyr Phe
                20                  25                  30

Leu Phe Gln Thr Gly Gly Asn Tyr
            35                  40

<210> SEQ ID NO 148
<211> LENGTH: 21
<212> TYPE: PRT
<213> ORGANISM: Homo sapiens

<400> SEQUENCE: 148

Ile Asn Lys Pro Cys Ile Lys Val Ala Ser Glu Arg Val Lys Ile Cys
1               5                   10                  15

Val Phe Phe Glu Tyr
            20

<210> SEQ ID NO 149
<211> LENGTH: 40
<212> TYPE: PRT
<213> ORGANISM: Homo sapiens

<400> SEQUENCE: 149

Leu Arg Pro Pro Gly Gly Ser Thr Lys Val Glu Ser Trp Thr Lys Ala
1               5                   10                  15

Ala Leu Cys Ser Cys Pro Gly Leu Pro Thr Ala Pro Phe His His His
                20                  25                  30

Ser His Ser Ile Gln Leu Tyr Phe
            35                  40

<210> SEQ ID NO 150
<211> LENGTH: 121
<212> TYPE: PRT
<213> ORGANISM: Homo sapiens
<220> FEATURE:
<221> NAME/KEY: MOD_RES
<222> LOCATION: (49)..(49)
<223> OTHER INFORMATION: Variable amino acid
<220> FEATURE:
<221> NAME/KEY: MOD_RES
<222> LOCATION: (79)..(79)
<223> OTHER INFORMATION: Variable amino acid

<400> SEQUENCE: 150

Leu Pro Val Gly Gly Arg Ile Gly Gly Lys Val Thr Lys Thr Ala
1               5                   10                  15

Lys Glu Arg Asp Arg Ala Thr Gln Ser Leu Ser Asp Trp Thr Gly Gln
                20                  25                  30

Ala Pro Met Glu Ser Leu Ser Ile Pro His Leu Leu Leu Pro Leu Ala
                35                  40                  45

Xaa Leu Thr Gly Glu Gly Ser Lys Leu Gly Phe Cys Trp Glu Trp Lys
    50                  55                  60

Leu Cys Gly Leu Phe Ile Ile Gly Thr Ile Met Ala Lys Ile Xaa Arg
65                  70                  75                  80

Ala Leu Arg Ser Glu Val Asn Thr Asp Ala Ile Phe Pro Val Cys Thr
                85                  90                  95

His Val Leu Arg His Pro Asn Gly Ser Gly Gln Asn Phe Leu Trp Leu
                100                 105                 110

Val Pro His Tyr Leu Asn Leu Cys Thr
            115                 120

<210> SEQ ID NO 151

```
<211> LENGTH: 46
<212> TYPE: PRT
<213> ORGANISM: Homo sapiens

<400> SEQUENCE: 151

Leu Ser Lys Thr Leu Val Leu Asn Ser Thr Asp Met Arg Ala Gln Lys
1               5                   10                  15

Arg Asp Val Ser Leu Ile Phe His Ser Val Thr Leu Ile Pro Thr Phe
                20                  25                  30

Pro Ala Ser Pro Cys His Trp Cys Ser Leu Val Pro Glu Ala
            35                  40                  45

<210> SEQ ID NO 152
<211> LENGTH: 46
<212> TYPE: PRT
<213> ORGANISM: Homo sapiens

<400> SEQUENCE: 152

Leu Pro Tyr Tyr Val Arg Thr Leu Gly Ser Pro Asn Asp Arg Ala
1               5                   10                  15

Thr Val Ser Gly Leu Ile Ala Leu Pro Ile Ser Trp Ile Lys Lys
                20                  25                  30

Arg Leu Thr Tyr Lys Ile Pro Phe Leu Lys Met Ser Thr Val
            35                  40                  45

<210> SEQ ID NO 153
<211> LENGTH: 44
<212> TYPE: PRT
<213> ORGANISM: Homo sapiens

<400> SEQUENCE: 153

Val Glu Val Arg Phe Trp Gly Met Glu Gly Cys Leu Asp Ala Lys Ser
1               5                   10                  15

Lys Thr Val Glu Lys Arg Ile Met Gly Gly Ile Arg Gly Trp Asn Phe
                20                  25                  30

Ser Leu Leu Val Pro Tyr Asn Leu Cys Phe Leu Lys
            35                  40

<210> SEQ ID NO 154
<211> LENGTH: 35
<212> TYPE: PRT
<213> ORGANISM: Homo sapiens

<400> SEQUENCE: 154

Phe Tyr Gly Asn Trp Gly Gln Glu Lys Gly Ile Ser Arg His Arg Trp
1               5                   10                  15

Asp Pro Lys Arg Gly Leu Lys Phe Glu Glu Thr Met Gly Val Gly Lys
                20                  25                  30

Gly Cys Leu
            35

<210> SEQ ID NO 155
<211> LENGTH: 106
<212> TYPE: PRT
<213> ORGANISM: Homo sapiens

<400> SEQUENCE: 155

Asp Glu Glu Ile Val Val Gly Gly Ser Leu Gly Gly Asp Arg Thr Leu
1               5                   10                  15

Asn Arg Asp Arg Trp Gln Thr Val Cys Gly Gln Ala Gly Gly Ser Thr
                20                  25                  30
```

His Leu Ile Ser Val Glu Val Gly Arg Ala Gly Arg Ser Gln His Ser
             35                  40                  45

Gln Pro Trp Arg Lys Cys Lys Cys Asp Lys Lys Gln Lys Glu Glu
    50                  55                  60

Thr Pro Gly Gln Gly Ala Pro Cys His Arg Phe Phe Pro Trp Pro Trp
65                  70                  75                  80

Leu Trp Glu Glu Leu Gly Lys Gly Gly Asp Ser Ala Ser Ser Glu Lys
                85                  90                  95

Pro Ser Leu Pro Leu Trp Thr Leu Glu Ala
            100                 105

<210> SEQ ID NO 156
<211> LENGTH: 12
<212> TYPE: PRT
<213> ORGANISM: Homo sapiens

<400> SEQUENCE: 156

Arg Gly Glu Cys Val Gly Met Met Trp Lys Glu
1               5                   10

<210> SEQ ID NO 157
<211> LENGTH: 9
<212> TYPE: PRT
<213> ORGANISM: Homo sapiens

<400> SEQUENCE: 157

Leu Asp Leu Ser Arg Cys Val Cys Glu
1               5

<210> SEQ ID NO 158
<211> LENGTH: 18
<212> TYPE: PRT
<213> ORGANISM: Homo sapiens

<400> SEQUENCE: 158

Asp Phe Arg Asn Glu Asn Gly Asn Thr Ala Val Leu Gln His Gly Arg
1               5                   10                  15

Gly Pro

<210> SEQ ID NO 159
<211> LENGTH: 19
<212> TYPE: PRT
<213> ORGANISM: Homo sapiens

<400> SEQUENCE: 159

Asp Pro Ser Pro Pro His Arg Lys Arg Ile Ile Gln Ser Ser His
1               5                   10                  15

Leu Gly Phe

<210> SEQ ID NO 160
<211> LENGTH: 10
<212> TYPE: PRT
<213> ORGANISM: Homo sapiens

<400> SEQUENCE: 160

Gly His Asp Ile Asp Thr Glu Gln Glu Ser
1               5                   10

<210> SEQ ID NO 161
<211> LENGTH: 11
<212> TYPE: PRT

-continued

<213> ORGANISM: Homo sapiens

<400> SEQUENCE: 161

Asp Arg Asn Thr Pro Ser Cys Leu Val Ser His
1               5                   10

<210> SEQ ID NO 162
<211> LENGTH: 6
<212> TYPE: PRT
<213> ORGANISM: Homo sapiens

<400> SEQUENCE: 162

Ala Ser Pro Val Leu His
1               5

<210> SEQ ID NO 163
<211> LENGTH: 5
<212> TYPE: PRT
<213> ORGANISM: Homo sapiens

<400> SEQUENCE: 163

Leu Ile Gly Gly Cys
1               5

<210> SEQ ID NO 164
<211> LENGTH: 10
<212> TYPE: PRT
<213> ORGANISM: Homo sapiens

<400> SEQUENCE: 164

Ser Ser Pro Leu Arg Ser Leu Leu Pro Leu
1               5                   10

<210> SEQ ID NO 165
<211> LENGTH: 61
<212> TYPE: PRT
<213> ORGANISM: Homo sapiens

<400> SEQUENCE: 165

Thr Pro Pro Thr Thr Leu His Arg Ala Thr Arg Gly Arg Ile Trp Ile
1               5                   10                  15

Gln Cys Leu Thr Ala Cys Trp Gly Trp Thr Ala Met Val Arg Gly Lys
                20                  25                  30

Thr Glu Asp Arg Gly Ile Gly Thr Met His Ser Leu Ile Lys Gly Arg
            35                  40                  45

Thr Gly Pro Ser Trp Pro Leu Lys Val Pro Gly Ala Pro
        50                  55                  60

<210> SEQ ID NO 166
<211> LENGTH: 37
<212> TYPE: PRT
<213> ORGANISM: Homo sapiens

<400> SEQUENCE: 166

Arg Leu Met His Ser Pro Ser His Tyr Thr Lys Asp His Ala His Arg
1               5                   10                  15

Ile Phe Ile Ser Ile Phe Ser Phe Gln Asp Ala Gly Gly Cys Pro Leu
                20                  25                  30

Gly Trp Ala Ile Arg
        35

<210> SEQ ID NO 167

-continued

```
<211> LENGTH: 24
<212> TYPE: PRT
<213> ORGANISM: Homo sapiens

<400> SEQUENCE: 167

Pro Glu Arg Gly Cys Leu Ser Leu Leu Tyr Arg Gly Ile Pro Gln Cys
1               5                   10                  15

Ser Met Tyr Gln Arg Pro Pro Gly
            20

<210> SEQ ID NO 168
<211> LENGTH: 4
<212> TYPE: PRT
<213> ORGANISM: Homo sapiens

<400> SEQUENCE: 168

Pro Phe Pro Cys
1

<210> SEQ ID NO 169
<211> LENGTH: 40
<212> TYPE: PRT
<213> ORGANISM: Homo sapiens

<400> SEQUENCE: 169

Phe Leu Met Leu Thr Ser Ser Asn Ser Asp Pro Leu Asp Leu Val Phe
1               5                   10                  15

Asn Asp Pro Glu Leu Lys Lys Pro Asn Tyr Asp Pro Met Thr Ser Phe
            20                  25                  30

Ser Ser Thr Leu Pro Pro Thr Arg
        35                  40

<210> SEQ ID NO 170
<211> LENGTH: 24
<212> TYPE: PRT
<213> ORGANISM: Homo sapiens

<400> SEQUENCE: 170

Leu Ser Thr Trp Lys Phe Leu Ser Ala Cys Cys Glu Tyr Ala Pro Arg
1               5                   10                  15

Asp Val Ser Thr Arg Asp Arg Cys
            20

<210> SEQ ID NO 171
<211> LENGTH: 42
<212> TYPE: PRT
<213> ORGANISM: Homo sapiens

<400> SEQUENCE: 171

Trp Gly Ile His Gly Glu Leu Lys Glu Gly Pro Gln Lys Val His Ser
1               5                   10                  15

Arg Glu Glu Ser Ile Met Val Ser Gly Gln Trp Trp Leu Gly Pro Phe
            20                  25                  30

Ile Pro Val Phe Trp Arg Gln Ser Gln Ala
        35                  40

<210> SEQ ID NO 172
<211> LENGTH: 13
<212> TYPE: PRT
<213> ORGANISM: Homo sapiens

<400> SEQUENCE: 172
```

```
Ala Pro Gly Gln Pro Arg Leu Cys Arg Glu Thr Leu Phe
1               5                   10
```

<210> SEQ ID NO 173
<211> LENGTH: 6
<212> TYPE: PRT
<213> ORGANISM: Homo sapiens

<400> SEQUENCE: 173

```
Lys Thr Gln Asn Gln Asn
1               5
```

<210> SEQ ID NO 174
<211> LENGTH: 41
<212> TYPE: PRT
<213> ORGANISM: Homo sapiens

<400> SEQUENCE: 174

```
Pro Asn Asn Asn Arg Lys Ser Thr Val Arg Glu Ile Ser Leu
1               5                   10                  15

Tyr Arg Arg Asp Lys Glu Phe Lys Thr Leu Glu Ser Lys Ala Gly Phe
            20                  25                  30

Pro Met Glu Trp Ser Pro Ser Leu Phe
        35                  40
```

<210> SEQ ID NO 175
<211> LENGTH: 13
<212> TYPE: PRT
<213> ORGANISM: Homo sapiens

<400> SEQUENCE: 175

```
Leu Gly Val Cys Ser Glu Arg Pro Ser Gln Ala Trp Gly
1               5                   10
```

<210> SEQ ID NO 176
<211> LENGTH: 66
<212> TYPE: PRT
<213> ORGANISM: Homo sapiens

<400> SEQUENCE: 176

```
Leu Phe Leu Leu Ser Thr Gln Ala Cys Ala Pro Leu Trp Ser Arg Ala
1               5                   10                  15

Cys Gly Ser Ser Val Phe Ser Ser Gly Ile Cys Ala Arg Val Asp Ala
            20                  25                  30

Ser Phe Arg Pro Gln Gly Ser Leu Ala Pro Thr Ala Gln Arg Glu Pro
        35                  40                  45

Val Glu Gly Pro Trp Lys Leu Ser Ser Gln Ile Gly Met Leu Gly Gly
    50                  55                  60

Lys Asn
65
```

<210> SEQ ID NO 177
<211> LENGTH: 27
<212> TYPE: PRT
<213> ORGANISM: Homo sapiens

<400> SEQUENCE: 177

```
Asp Lys Asp Leu Val Glu Gly Leu His Gly Tyr Pro His His Ser Gln
1               5                   10                  15

Val Cys Leu Gln Lys Arg Leu Leu Phe Ala Asn
            20                  25
```

```
<210> SEQ ID NO 178
<211> LENGTH: 19
<212> TYPE: PRT
<213> ORGANISM: Homo sapiens

<400> SEQUENCE: 178

Leu Glu Phe Arg Leu Leu Arg Arg Ala Ser Arg His Gln Asp Leu Val
1               5                   10                  15

Leu Pro Thr

<210> SEQ ID NO 179
<211> LENGTH: 58
<212> TYPE: PRT
<213> ORGANISM: Homo sapiens

<400> SEQUENCE: 179

Lys Gln Asn Lys Thr Ala Tyr Pro Val His Ser Leu Ser Leu Ile His
1               5                   10                  15

His Val Ser Ser Ile Ser Tyr Phe Cys Gly Ser Tyr Arg Cys Gln Val
            20                  25                  30

Ser Thr Gln Leu Leu Gly Ser Pro Leu Met Pro Phe Ile Tyr Phe Leu
        35                  40                  45

Ile Tyr Cys Leu Leu Gly Asp Ser Leu Met
    50                  55

<210> SEQ ID NO 180
<211> LENGTH: 31
<212> TYPE: PRT
<213> ORGANISM: Homo sapiens

<400> SEQUENCE: 180

Pro Arg Leu Ser Leu Ile Leu Glu Phe Ala Cys Leu Ser Phe Ser Val
1               5                   10                  15

Ser Ser Thr Gly Ile Ile Gly Met His Cys Leu Pro Gly Leu Cys
            20                  25                  30

<210> SEQ ID NO 181
<211> LENGTH: 28
<212> TYPE: PRT
<213> ORGANISM: Homo sapiens

<400> SEQUENCE: 181

Thr Cys Pro Leu Trp Pro Leu Val Gly His Glu Ser Asn Thr Ala Leu
1               5                   10                  15

Pro His Asn Thr His Thr Asn Glu Ser Glu Ala Leu
            20                  25

<210> SEQ ID NO 182
<211> LENGTH: 6
<212> TYPE: PRT
<213> ORGANISM: Homo sapiens

<400> SEQUENCE: 182

Val Phe His Ser Thr Gly
1               5

<210> SEQ ID NO 183
<211> LENGTH: 22
<212> TYPE: PRT
<213> ORGANISM: Homo sapiens

<400> SEQUENCE: 183
```

```
Cys Ile Phe His Ser Phe Thr Leu Pro Ile Ser Ser Phe Asp Phe
1               5                  10                  15

His Thr Gly Asp Leu Ala
            20
```

<210> SEQ ID NO 184
<211> LENGTH: 5
<212> TYPE: PRT
<213> ORGANISM: Homo sapiens

<400> SEQUENCE: 184

```
Tyr Phe Pro Gly Asn
1               5
```

<210> SEQ ID NO 185
<211> LENGTH: 5
<212> TYPE: PRT
<213> ORGANISM: Homo sapiens

<400> SEQUENCE: 185

```
Glu Arg Ile Pro Phe
1               5
```

<210> SEQ ID NO 186
<211> LENGTH: 132
<212> TYPE: PRT
<213> ORGANISM: Homo sapiens

<400> SEQUENCE: 186

```
Val Pro Ala Leu Gln Arg Pro Gly Thr Phe Ser Leu Ala Asp Tyr
1               5                  10                  15

Thr Pro His Pro Ser Met Phe Phe Val Ser His His Tyr Ala Pro Leu
            20                  25                  30

Leu Gly Cys Pro Thr Tyr Met Asp Val Val Ile Val Leu Asp Gly Ser
        35                  40                  45

Asn Ser Ile Tyr Pro Trp Ser Glu Val Gln Thr Phe Leu Arg Arg Leu
    50                  55                  60

Val Gly Arg Leu Phe Ile Asp Pro Glu Gln Ile Gln Val Arg Glu Arg
65                  70                  75                  80

Tyr Val Asp Arg Ile Gly Gly Lys Glu Val Asn Thr Pro Gly Pro Leu
                85                  90                  95

Asp Val Ser Ser His Val Gln Pro Leu Asp Asp Thr Leu Gly His Cys
            100                 105                 110

Leu Leu Gln Asn Ser Cys Ser Arg Thr Val Gln Leu Thr Tyr Lys Val
        115                 120                 125

Thr Lys Ile Ser
    130
```

<210> SEQ ID NO 187
<211> LENGTH: 46
<212> TYPE: PRT
<213> ORGANISM: Homo sapiens

<400> SEQUENCE: 187

```
Val Tyr Asp Cys Val Gly Gly His Thr Gln Ser Phe Pro Leu Leu Leu
1               5                  10                  15

Val Val Ala Trp Ala Met His Ala Met Ser Cys Lys Leu Asp Thr Pro
            20                  25                  30

Val His Phe Pro Phe Ile Val Leu Gln Val Gly His Thr Cys
```

35                  40                  45

<210> SEQ ID NO 188
<211> LENGTH: 29
<212> TYPE: PRT
<213> ORGANISM: Homo sapiens

<400> SEQUENCE: 188

Gly Phe Thr Ser Pro Ser Ser Phe Val Leu His Leu Leu Tyr Ala Leu
1               5                   10                  15

His Thr Ser His Val Gly Thr Trp Ser Ile Val Leu Arg
            20                  25

<210> SEQ ID NO 189
<211> LENGTH: 24
<212> TYPE: PRT
<213> ORGANISM: Homo sapiens

<400> SEQUENCE: 189

Asp Trp Tyr Ser Thr Gly Arg Thr Leu Cys Met Ser Gly Pro Trp Glu
1               5                   10                  15

Thr Ser Glu Gln Arg Lys Lys Leu
            20

<210> SEQ ID NO 190
<211> LENGTH: 5
<212> TYPE: PRT
<213> ORGANISM: Homo sapiens

<400> SEQUENCE: 190

Glu Gln Gln Gly Thr
1               5

<210> SEQ ID NO 191
<211> LENGTH: 21
<212> TYPE: PRT
<213> ORGANISM: Homo sapiens

<400> SEQUENCE: 191

Val Gly Gly Lys Gly Glu Lys Arg Glu Pro Pro Lys Arg Ser Trp Trp
1               5                   10                  15

His Gly Glu Thr Leu
            20

<210> SEQ ID NO 192
<211> LENGTH: 19
<212> TYPE: PRT
<213> ORGANISM: Homo sapiens

<400> SEQUENCE: 192

Arg Gly Arg Val Arg Glu Glu Glu Gly Ser Ala Gly Arg Gly Arg Gly
1               5                   10                  15

Ser Gly Val

<210> SEQ ID NO 193
<211> LENGTH: 92
<212> TYPE: PRT
<213> ORGANISM: Homo sapiens

<400> SEQUENCE: 193

Cys Ile His His Lys Met Leu Trp Ala Leu Ile Phe Ile Cys Met Pro
1               5                   10                  15

```
Glu Val Arg Gly Gly Arg Leu Gly Cys Cys His His Thr Leu Ser Tyr
                 20                  25                  30

Cys Ile Cys Ile Leu Trp Cys Leu Trp Val Tyr Leu Ser Leu Ser Val
             35                  40                  45

Leu Phe Leu His Thr Glu Leu His Leu Ser Ser Ser Thr Pro Ala Ser
 50                  55                  60

Ile Leu Ile Pro Ser Phe Ser Thr Thr His Ala Leu Val Phe Phe Ser
 65                  70                  75                  80

Asn Met Thr Leu Asn Leu Trp Gly Gly Tyr Met Thr
                 85                  90
```

<210> SEQ ID NO 194
<211> LENGTH: 17
<212> TYPE: PRT
<213> ORGANISM: Homo sapiens

<400> SEQUENCE: 194

```
Leu Ser Leu Phe Ser Ser Ser Leu Ile Leu Ser Thr Gln Val Phe Ala
 1               5                  10                  15

Glu
```

<210> SEQ ID NO 195
<211> LENGTH: 19
<212> TYPE: PRT
<213> ORGANISM: Homo sapiens

<400> SEQUENCE: 195

```
Ile Met Leu Val His Ile Tyr Thr Asp Asp Arg Leu Phe Tyr Met Phe
 1               5                  10                  15

Arg Ala Ile
```

<210> SEQ ID NO 196
<211> LENGTH: 4
<212> TYPE: PRT
<213> ORGANISM: Homo sapiens

<400> SEQUENCE: 196

```
Thr Val Lys Leu
 1
```

<210> SEQ ID NO 197
<211> LENGTH: 14
<212> TYPE: PRT
<213> ORGANISM: Homo sapiens

<400> SEQUENCE: 197

```
Leu Cys Ala Ser Leu His Ala Arg Tyr Cys Trp Gly Met Val
 1               5                  10
```

<210> SEQ ID NO 198
<211> LENGTH: 45
<212> TYPE: PRT
<213> ORGANISM: Homo sapiens

<400> SEQUENCE: 198

```
Lys Thr Ser Asp Leu Ser Glu Leu Leu Thr Val Leu Ile His Tyr Thr
 1               5                  10                  15

Gly Met Pro Ala Cys Lys Pro Val Cys Met Cys Met His Met His Thr
                 20                  25                  30

His Thr Tyr Asp His Ile Ala Phe Tyr Leu Ser Ser
             35                  40                  45
```

<210> SEQ ID NO 199
<211> LENGTH: 15
<212> TYPE: PRT
<213> ORGANISM: Homo sapiens

<400> SEQUENCE: 199

His Arg Arg Val Gln Ser Val Pro Gly Gly Thr Thr Arg Gly Arg
1               5                   10                  15

<210> SEQ ID NO 200
<211> LENGTH: 6
<212> TYPE: PRT
<213> ORGANISM: Homo sapiens

<400> SEQUENCE: 200

Ala Ala Gly Ser Cys His
1               5

<210> SEQ ID NO 201
<211> LENGTH: 4
<212> TYPE: PRT
<213> ORGANISM: Homo sapiens

<400> SEQUENCE: 201

Trp Arg Val Pro
1

<210> SEQ ID NO 202
<211> LENGTH: 11
<212> TYPE: PRT
<213> ORGANISM: Homo sapiens

<400> SEQUENCE: 202

Trp Arg Gly Thr Ser Ser Ser Ala Lys Gly Leu
1               5                   10

<210> SEQ ID NO 203
<211> LENGTH: 13
<212> TYPE: PRT
<213> ORGANISM: Homo sapiens

<400> SEQUENCE: 203

Gly Trp Gln Ser Asp Thr Leu Trp Asp Cys Gly Glu Thr
1               5                   10

<210> SEQ ID NO 204
<211> LENGTH: 70
<212> TYPE: PRT
<213> ORGANISM: Homo sapiens

<400> SEQUENCE: 204

Ser Ser Pro Val Val Leu Phe Cys Val Ser Cys Val Cys Val Cys
1               5                   10                  15

Val Cys Val Cys Val Cys Val Cys Val Cys Met Cys Asp Met Cys Ala
                20                  25                  30

Cys Ile Ser Ala His Thr Ile Val Cys Ile Cys Gly Ser Glu Asn Asn
            35                  40                  45

Leu Arg Cys Trp Ser Ser Pro Ser Ile Leu Phe Gln Thr Gly Tyr Leu
        50                  55                  60

Val His Phe Gly Ile Gln
65                  70

```
<210> SEQ ID NO 205
<211> LENGTH: 21
<212> TYPE: PRT
<213> ORGANISM: Homo sapiens

<400> SEQUENCE: 205

Ala Arg Leu Ala Asp Pro Gln Val Leu Gly Arg Ser Ser Val Ser Ala
1               5                   10                  15

Ser Cys Leu Leu Val
            20

<210> SEQ ID NO 206
<211> LENGTH: 29
<212> TYPE: PRT
<213> ORGANISM: Homo sapiens

<400> SEQUENCE: 206

Gly Ile Leu Glu Phe Thr Asp Lys Leu Asp Ile Glu Phe Leu Gln Pro
1               5                   10                  15

Gly Gly Ser Thr Ser Ser Arg Ala Ala Ala Thr Lys Gly
            20                  25

<210> SEQ ID NO 207
<211> LENGTH: 8
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid

<400> SEQUENCE: 207

Gln Ser Xaa Xaa Lys Xaa Glu Val
1               5

<210> SEQ ID NO 208
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(8)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid

<400> SEQUENCE: 208

Pro Val Gly Xaa Asp Xaa Xaa Xaa Ala Xaa Xaa
1               5                   10

<210> SEQ ID NO 209
<211> LENGTH: 110
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Variable amino acid
```

-continued

```
<220> FEATURE:
<221> NAME/KEY: MOD_RES
<222> LOCATION: (7)..(11)
<223> OTHER INFORMATION: Variable amino acid
<220> FEATURE:
<221> NAME/KEY: MOD_RES
<222> LOCATION: (13)..(15)
<223> OTHER INFORMATION: Variable amino acid
<220> FEATURE:
<221> NAME/KEY: MOD_RES
<222> LOCATION: (18)..(19)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid
<220> FEATURE:
<221> NAME/KEY: MOD_RES
<222> LOCATION: (29)..(30)
<223> OTHER INFORMATION: Variable amino acid
<220> FEATURE:
<221> NAME/KEY: MOD_RES
<222> LOCATION: (34)..(34)
<223> OTHER INFORMATION: Variable amino acid
<220> FEATURE:
<221> NAME/KEY: MOD_RES
<222> LOCATION: (36)..(36)
<223> OTHER INFORMATION: Variable amino acid
<220> FEATURE:
<221> NAME/KEY: MOD_RES
<222> LOCATION: (38)..(40)
<223> OTHER INFORMATION: Variable amino acid
<220> FEATURE:
<221> NAME/KEY: MOD_RES
<222> LOCATION: (42)..(43)
<223> OTHER INFORMATION: Variable amino acid
<220> FEATURE:
<221> NAME/KEY: MOD_RES
<222> LOCATION: (47)..(49)
<223> OTHER INFORMATION: Variable amino acid
<220> FEATURE:
<221> NAME/KEY: MOD_RES
<222> LOCATION: (54)..(54)
<223> OTHER INFORMATION: Variable amino acid
<220> FEATURE:
<221> NAME/KEY: MOD_RES
<222> LOCATION: (56)..(56)
<223> OTHER INFORMATION: Variable amino acid
<220> FEATURE:
<221> NAME/KEY: MOD_RES
<222> LOCATION: (58)..(63)
<223> OTHER INFORMATION: Variable amino acid
<220> FEATURE:
<221> NAME/KEY: MOD_RES
<222> LOCATION: (65)..(66)
<223> OTHER INFORMATION: Variable amino acid
<220> FEATURE:
<221> NAME/KEY: MOD_RES
<222> LOCATION: (69)..(69)
<223> OTHER INFORMATION: Variable amino acid
<220> FEATURE:
<221> NAME/KEY: MOD_RES
<222> LOCATION: (71)..(73)
<223> OTHER INFORMATION: Variable amino acid
<220> FEATURE:
<221> NAME/KEY: MOD_RES
<222> LOCATION: (77)..(77)
<223> OTHER INFORMATION: Variable amino acid
<220> FEATURE:
<221> NAME/KEY: MOD_RES
<222> LOCATION: (79)..(80)
<223> OTHER INFORMATION: Variable amino acid
<220> FEATURE:
<221> NAME/KEY: MOD_RES
<222> LOCATION: (84)..(84)
<223> OTHER INFORMATION: Variable amino acid
<220> FEATURE:
<221> NAME/KEY: MOD_RES
<222> LOCATION: (86)..(86)
```

```
<223> OTHER INFORMATION: Variable amino acid
<220> FEATURE:
<221> NAME/KEY: MOD_RES
<222> LOCATION: (89)..(89)
<223> OTHER INFORMATION: Variable amino acid
<220> FEATURE:
<221> NAME/KEY: MOD_RES
<222> LOCATION: (93)..(93)
<223> OTHER INFORMATION: Variable amino acid
<220> FEATURE:
<221> NAME/KEY: MOD_RES
<222> LOCATION: (96)..(97)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid
<220> FEATURE:
<221> NAME/KEY: MOD_RES
<222> LOCATION: (104)..(105)
<223> OTHER INFORMATION: Variable amino acid
<220> FEATURE:
<221> NAME/KEY: MOD_RES
<222> LOCATION: (107)..(107)
<223> OTHER INFORMATION: Variable amino acid

<400> SEQUENCE: 209

Arg Thr Met Xaa Xaa Pro Xaa Xaa Xaa Xaa Arg Xaa Xaa Xaa Ser
1               5                   10                  15

Lys Xaa Xaa Ser Gln Glu Pro Thr Xaa Trp Leu Ala Xaa Xaa Arg Asp
            20                  25                  30

Gln Xaa Arg Xaa Leu Xaa Xaa Xaa Leu Xaa Xaa Ile Asn Arg Xaa Xaa
        35                  40                  45

Xaa Gly Gly Gly Ile Xaa Lys Xaa Trp Xaa Xaa Xaa Xaa Xaa Met
    50                  55                  60

Xaa Xaa Arg Leu Xaa Arg Xaa Xaa Xaa Val Gln Ala Xaa Thr Xaa Xaa
65                  70                  75                  80

Cys Leu Arg Xaa Ser Xaa Gly Gln Xaa Cys Arg Ser Xaa Asp Leu Xaa
                85                  90                  95

Xaa Ile Arg Xaa Xaa Asp Leu Xaa Xaa Gly Xaa Ala Ser Ala
            100                 105                 110

<210> SEQ ID NO 210
<211> LENGTH: 15
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid

<400> SEQUENCE: 210

Thr Xaa Xaa Gly Xaa Ser Thr Xaa Thr Pro Xaa Xaa Asp Ile Tyr
1               5                   10                  15

<210> SEQ ID NO 211
<211> LENGTH: 11
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid

<400> SEQUENCE: 211

Xaa Arg Arg Val Ala Arg Ser Xaa Glu Met Ile
1               5                   10

<210> SEQ ID NO 212
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Variable amino acid

<400> SEQUENCE: 212

Xaa Gly Val Pro Leu Pro Val Tyr Glu Arg Thr Gly Ser Ala Asp Ile
1               5                   10                  15

Asp Ala Leu Cys
            20

<210> SEQ ID NO 213
<211> LENGTH: 22
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (14)..(14)
<223> OTHER INFORMATION: Variable amino acid
<220> FEATURE:
<221> NAME/KEY: MOD_RES
<222> LOCATION: (20)..(21)
<223> OTHER INFORMATION: Variable amino acid

<400> SEQUENCE: 213

Leu Thr Tyr Cys Cys Xaa Glu Xaa Asp Gln Ile Arg Ser Xaa Val Pro
1               5                   10                  15

His His Glu Xaa Xaa Pro
            20

<210> SEQ ID NO 214
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Variable amino acid

<400> SEQUENCE: 214

Asp Ser Pro Met Met Glu Gln Glu Thr Xaa Ala Thr Ala Gly Glu
1               5                   10                  15
```

```
<210> SEQ ID NO 215
<211> LENGTH: 4
<212> TYPE: PRT
<213> ORGANISM: Homo sapiens

<400> SEQUENCE: 215

Arg Phe Leu Glu
1

<210> SEQ ID NO 216
<211> LENGTH: 59
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Variable amino acid
<220> FEATURE:
<221> NAME/KEY: MOD_RES
<222> LOCATION: (25)..(25)
<223> OTHER INFORMATION: Variable amino acid
<220> FEATURE:
<221> NAME/KEY: MOD_RES
<222> LOCATION: (33)..(33)
<223> OTHER INFORMATION: Variable amino acid
<220> FEATURE:
<221> NAME/KEY: MOD_RES
<222> LOCATION: (37)..(37)
<223> OTHER INFORMATION: Variable amino acid

<400> SEQUENCE: 216

Glu Ser Gln Glu Glu Arg Asn Cys Gly Pro Gly Gly Pro Thr Pro
1               5                   10                  15

Gly Gly Ser Xaa His Asn Trp Leu Xaa Val Ser Ala Pro Ile Leu Ile
            20                  25                  30

Xaa Ala Arg Pro Xaa Ser Tyr Pro Pro Leu Leu Leu Asp Gly Ser Glu
        35                  40                  45

Met Pro Gly Pro Phe His Pro His Trp Thr Asn
    50                  55

<210> SEQ ID NO 217
<211> LENGTH: 24
<212> TYPE: PRT
<213> ORGANISM: Homo sapiens

<400> SEQUENCE: 217

Ala Ser Gly Val Val Ala Leu Gly Leu Trp Gly Cys Val Ala Ser Tyr
1               5                   10                  15

Pro Pro Phe Cys Leu Phe Ser Pro
            20

<210> SEQ ID NO 218
<211> LENGTH: 10
<212> TYPE: PRT
<213> ORGANISM: Homo sapiens

<400> SEQUENCE: 218

Ser Val Pro Gly Tyr Asp Ser Ser Pro Asp
1               5                   10

<210> SEQ ID NO 219
<211> LENGTH: 5
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: Variable amino acid

<400> SEQUENCE: 219

Xaa Cys Gly Thr Arg
1               5

<210> SEQ ID NO 220
<211> LENGTH: 6
<212> TYPE: PRT
<213> ORGANISM: Homo sapiens

<400> SEQUENCE: 220

Gly Gly Ser Pro Gly Gly
1               5

<210> SEQ ID NO 221
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 221

Asp Gly Xaa Leu Cys Ala Xaa Leu Ile Val Ile Gln Leu Pro
1               5                   10

<210> SEQ ID NO 222
<211> LENGTH: 53
<212> TYPE: PRT
<213> ORGANISM: Homo sapiens
<220> FEATURE:
<221> NAME/KEY: MOD_RES
<222> LOCATION: (49)..(49)
<223> OTHER INFORMATION: Variable amino acid

<400> SEQUENCE: 222

Leu Lys Leu Lys Ser Arg Ser Leu Gly Met Arg Gly Arg Thr Cys Gln
1               5                   10                  15
Arg Arg Val Arg Lys Ala Val Leu Arg Glu Gly Ser Cys Arg Pro Leu
            20                  25                  30
Gln Leu Asp Phe Ile Gln Ser His Cys Gln Asn Leu Ile Ala Leu Pro
        35                  40                  45
Xaa Ile Ser Leu Ser
    50

<210> SEQ ID NO 223
<211> LENGTH: 12
<212> TYPE: PRT
<213> ORGANISM: Homo sapiens

<400> SEQUENCE: 223

Leu Arg Ile Cys Tyr Arg Arg Gln Asn Ser Leu Ser
1               5                   10

<210> SEQ ID NO 224
<211> LENGTH: 19
<212> TYPE: PRT
<213> ORGANISM: Homo sapiens
```

```
<400> SEQUENCE: 224

Pro Pro Gly Gln Ile Phe Lys Arg Arg Gly Val Gly Tyr Phe Leu Val
1               5                   10                  15

Gly Glu Ala

<210> SEQ ID NO 225
<211> LENGTH: 46
<212> TYPE: PRT
<213> ORGANISM: Homo sapiens

<400> SEQUENCE: 225

Val Met Asp Ser Lys Val Leu Ile Val Phe Phe Ser Glu Thr Ser
1               5                   10                  15

Cys Ser Ile Phe Leu Pro Phe His Pro Pro Tyr Pro Arg Leu His
                20                  25                  30

Phe Met Pro Gly Val Ser Ser Leu Thr Pro Leu Gln Ala Val
                35                  40                  45

<210> SEQ ID NO 226
<211> LENGTH: 21
<212> TYPE: PRT
<213> ORGANISM: Homo sapiens

<400> SEQUENCE: 226

Gly Phe Ser Pro Gly Ser Ala Ser Ala Asp Cys Leu His Thr Phe Gln
1               5                   10                  15

Phe Leu Arg Thr Arg
                20

<210> SEQ ID NO 227
<211> LENGTH: 24
<212> TYPE: PRT
<213> ORGANISM: Homo sapiens

<400> SEQUENCE: 227

Ser Phe Leu Pro His Leu Ala Leu Ala Leu Ser Leu Thr Thr Gln Ala
1               5                   10                  15

Asp Ala Met Ser Gly Leu Phe Leu
                20

<210> SEQ ID NO 228
<211> LENGTH: 7
<212> TYPE: PRT
<213> ORGANISM: Homo sapiens

<400> SEQUENCE: 228

Ile Leu Tyr Asn Asp Ser Met
1               5

<210> SEQ ID NO 229
<211> LENGTH: 12
<212> TYPE: PRT
<213> ORGANISM: Homo sapiens

<400> SEQUENCE: 229

Ile Thr Gly Pro Cys Pro Gln Ser Lys Gln Ala Phe
1               5                   10

<210> SEQ ID NO 230
<211> LENGTH: 10
<212> TYPE: PRT
<213> ORGANISM: Homo sapiens
```

```
<400> SEQUENCE: 230

Ala Asn Lys Leu Lys Ile Lys Phe Ala His
1               5                   10

<210> SEQ ID NO 231
<211> LENGTH: 37
<212> TYPE: PRT
<213> ORGANISM: Homo sapiens

<400> SEQUENCE: 231

Leu Phe Tyr Ser Ile Gln Asp Gly Gly Trp Gly Gly Ala Asp
1               5                   10                  15

Cys Leu Phe Ser Leu Trp Tyr Leu Gly Arg Ala Glu Ala Leu Ser Ser
            20                  25                  30

Pro Ala Leu Gly Phe
        35

<210> SEQ ID NO 232
<211> LENGTH: 23
<212> TYPE: PRT
<213> ORGANISM: Homo sapiens

<400> SEQUENCE: 232

Val Ala Tyr Ser Glu Cys Tyr Cys Val Gln Leu Leu Val Asp Ile Trp
1               5                   10                  15

Ser Leu Met Val Trp Ser Leu
            20

<210> SEQ ID NO 233
<211> LENGTH: 4
<212> TYPE: PRT
<213> ORGANISM: Homo sapiens

<400> SEQUENCE: 233

Ala Leu Ala Leu
1

<210> SEQ ID NO 234
<211> LENGTH: 10
<212> TYPE: PRT
<213> ORGANISM: Homo sapiens

<400> SEQUENCE: 234

Leu Trp Met Ala Phe Leu Gly Val Ser Ser
1               5                   10

<210> SEQ ID NO 235
<211> LENGTH: 9
<212> TYPE: PRT
<213> ORGANISM: Homo sapiens

<400> SEQUENCE: 235

His Gly Tyr Arg Ile Ser Leu Lys Ile
1               5

<210> SEQ ID NO 236
<211> LENGTH: 18
<212> TYPE: PRT
<213> ORGANISM: Homo sapiens

<400> SEQUENCE: 236

Met Leu Gly Glu Arg Cys Gly His Thr Ile Met Val Pro Ile Gln Asn
```

```
            1               5               10              15
Asn Pro

<210> SEQ ID NO 237
<211> LENGTH: 13
<212> TYPE: PRT
<213> ORGANISM: Homo sapiens

<400> SEQUENCE: 237

Asn Ser Leu Lys Leu Gly Val Arg Cys Phe Gln Pro Lys
1               5                   10

<210> SEQ ID NO 238
<211> LENGTH: 33
<212> TYPE: PRT
<213> ORGANISM: Homo sapiens

<400> SEQUENCE: 238

His His Lys Ala His Leu Ser Thr Gly Ser Asp Ser Pro Lys Ala Ile
1               5                   10                  15

Arg His Thr Thr Ser Met Thr Ile Thr Gln Trp Ile Gly Lys Val Thr
            20                  25                  30

Gln

<210> SEQ ID NO 239
<211> LENGTH: 7
<212> TYPE: PRT
<213> ORGANISM: Homo sapiens

<400> SEQUENCE: 239

Asp Cys Pro Ser His Ser Arg
1               5

<210> SEQ ID NO 240
<211> LENGTH: 40
<212> TYPE: PRT
<213> ORGANISM: Homo sapiens

<400> SEQUENCE: 240

Glu Asn Ala Ala Val Thr Ala Val Ser Cys Tyr Phe Ala Tyr Pro Met
1               5                   10                  15

Leu Arg Leu Ile Arg Gln Lys Ile Leu Ser Leu Ser Pro Thr Phe Cys
            20                  25                  30

Ser Lys Leu Glu Glu Ile Ile Glu
        35                  40

<210> SEQ ID NO 241
<211> LENGTH: 4
<212> TYPE: PRT
<213> ORGANISM: Homo sapiens

<400> SEQUENCE: 241

Ile Asn Arg Ala
1

<210> SEQ ID NO 242
<211> LENGTH: 14
<212> TYPE: PRT
<213> ORGANISM: Homo sapiens

<400> SEQUENCE: 242

Pro Gln Lys Gly Ser Lys Phe Val Phe Ser Leu Asn Ile Ser
```

```
1               5                   10
```

<210> SEQ ID NO 243
<211> LENGTH: 8
<212> TYPE: PRT
<213> ORGANISM: Homo sapiens

<400> SEQUENCE: 243

```
Gly Leu Gln Gly Ala Ala Pro Arg
1               5
```

<210> SEQ ID NO 244
<211> LENGTH: 38
<212> TYPE: PRT
<213> ORGANISM: Homo sapiens

<400> SEQUENCE: 244

```
Arg Ala Gly Leu Arg Leu Leu Cys Val Pro Val Leu Gly Ser Pro Gln
1               5                   10                  15

Leu Pro Ser Thr Thr Thr Pro Ile Pro Ser Asn Phe Ile Phe Ser Cys
            20                  25                  30

Gln Trp Glu Gly Ala Gly
        35
```

<210> SEQ ID NO 245
<211> LENGTH: 37
<212> TYPE: PRT
<213> ORGANISM: Homo sapiens
<220> FEATURE:
<221> NAME/KEY: MOD_RES
<222> LOCATION: (37)..(37)
<223> OTHER INFORMATION: Variable amino acid

<400> SEQUENCE: 245

```
Arg Lys Gln Pro Arg Gly Thr Glu Gln Leu Arg Ala Ser Arg Thr
1               5                   10                  15

Gly Pro Asp Lys Arg Pro Trp Ser Leu Ser Pro Ser Leu Thr Cys Ser
            20                  25                  30

Cys Pro Trp Arg Xaa
        35
```

<210> SEQ ID NO 246
<211> LENGTH: 19
<212> TYPE: PRT
<213> ORGANISM: Homo sapiens

<400> SEQUENCE: 246

```
Gln Val Arg Glu Ala Asn Leu Val Ser Ala Gly Asn Gly Ser Tyr Val
1               5                   10                  15

Asp Cys Leu
```

<210> SEQ ID NO 247
<211> LENGTH: 46
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Variable amino acid

<400> SEQUENCE: 247

```
Leu Gly Pro Leu Trp Leu Lys Ser Xaa Gly Arg Ser Gly Arg Arg Leu
1               5                   10                  15
```

```
Ile Pro Met Leu Tyr Phe Leu Cys Ala Leu Met Phe Leu Asp Thr Gln
            20                  25                  30

Met Ala Val Ala Lys Thr Ser Ser Gly Leu Tyr Leu Ile Ile
        35                  40                  45
```

<210> SEQ ID NO 248
<211> LENGTH: 11
<212> TYPE: PRT
<213> ORGANISM: Homo sapiens

<400> SEQUENCE: 248

```
Thr Phe Val Pro Asn Tyr Leu Lys Pro Trp Ser
1               5                   10
```

<210> SEQ ID NO 249
<211> LENGTH: 4
<212> TYPE: PRT
<213> ORGANISM: Homo sapiens

<400> SEQUENCE: 249

```
Thr Pro Gln Thr
1
```

<210> SEQ ID NO 250
<211> LENGTH: 15
<212> TYPE: PRT
<213> ORGANISM: Homo sapiens

<400> SEQUENCE: 250

```
Gly His Arg Lys Glu Thr Cys Leu Ser Ser Ile Arg Leu His
1               5                   10                  15
```

<210> SEQ ID NO 251
<211> LENGTH: 40
<212> TYPE: PRT
<213> ORGANISM: Homo sapiens

<400> SEQUENCE: 251

```
Phe Leu Pro Ser Leu Leu Leu Pro Ala Ile Gly Ala Pro Trp Cys Leu
1               5                   10                  15

Arg His Asn Cys Leu Thr Met Trp Ser Glu Leu Trp Val Arg Leu Thr
            20                  25                  30

Thr Glu Leu Gln Phe Leu Val Ser
        35                  40
```

<210> SEQ ID NO 252
<211> LENGTH: 18
<212> TYPE: PRT
<213> ORGANISM: Homo sapiens

<400> SEQUENCE: 252

```
Pro Cys Gln Phe Pro Gly Leu Lys Lys Gly Ser His Ile Lys Tyr
1               5                   10                  15

Leu Phe
```

<210> SEQ ID NO 253
<211> LENGTH: 22
<212> TYPE: PRT
<213> ORGANISM: Homo sapiens

<400> SEQUENCE: 253

```
Ala Gln Cys Glu Leu Lys Leu Asp Phe Gly Gly Trp Arg Val Ala Trp
1               5                   10                  15
```

Met Gln Arg Ala Arg Gln
            20

<210> SEQ ID NO 254
<211> LENGTH: 7
<212> TYPE: PRT
<213> ORGANISM: Homo sapiens

<400> SEQUENCE: 254

Arg Arg Glu Ser Trp Glu Gly
1               5

<210> SEQ ID NO 255
<211> LENGTH: 7
<212> TYPE: PRT
<213> ORGANISM: Homo sapiens

<400> SEQUENCE: 255

Glu Ala Gly Ile Phe Pro Cys
1               5

<210> SEQ ID NO 256
<211> LENGTH: 7
<212> TYPE: PRT
<213> ORGANISM: Homo sapiens

<400> SEQUENCE: 256

Cys Pro Ile Ile Phe Val Ser
1               5

<210> SEQ ID NO 257
<211> LENGTH: 26
<212> TYPE: PRT
<213> ORGANISM: Homo sapiens

<400> SEQUENCE: 257

Asn Asn Ser Ser Asp Phe Met Gly Ile Gly Val Arg Arg Lys Glu Ser
1               5                   10                  15

Val Gly Thr Asp Gly Thr Pro Ser Val Asp
            20                  25

<210> SEQ ID NO 258
<211> LENGTH: 7
<212> TYPE: PRT
<213> ORGANISM: Homo sapiens

<400> SEQUENCE: 258

Ser Leu Arg Lys Leu Trp Glu
1               5

<210> SEQ ID NO 259
<211> LENGTH: 42
<212> TYPE: PRT
<213> ORGANISM: Homo sapiens

<400> SEQUENCE: 259

Ala Arg Gly Val Cys Lys Val Asp Glu Met Arg Arg Leu Trp Trp Gly
1               5                   10                  15

Gly Val Leu Gly Val Ile Gly Pro Leu Thr Gly Ile Asp Gly Lys Leu
            20                  25                  30

Cys Val Gly Arg Pro Val Val Pro Pro Thr
            35                  40

<210> SEQ ID NO 260
<211> LENGTH: 50
<212> TYPE: PRT
<213> ORGANISM: Homo sapiens

<400> SEQUENCE: 260

Leu Ala Leu Arg Leu Ala Gly Leu Glu Gly Ala Ser Thr Leu Asn Leu
1               5                   10                  15

Gly Glu Ser Ala Ser Val Thr Arg Arg Asn Arg Lys Arg His Pro
            20                  25                  30

Gly Arg Glu Leu Leu Ala Ile Val Ser Ser His Gly Pro Gly Phe Gly
        35                  40                  45

Lys Asn
    50

<210> SEQ ID NO 261
<211> LENGTH: 26
<212> TYPE: PRT
<213> ORGANISM: Homo sapiens

<400> SEQUENCE: 261

Glu Arg Val Val Thr Leu His Pro Gln Lys Ser Pro Leu Ser Leu Phe
1               5                   10                  15

Gly Leu Ser Arg Leu Arg Glu Glu Asn Val
            20                  25

<210> SEQ ID NO 262
<211> LENGTH: 84
<212> TYPE: PRT
<213> ORGANISM: Homo sapiens

<400> SEQUENCE: 262

Cys Gly Lys Ser Asn Leu Thr Tyr Pro Asp Val Ser Val Asn Glu Ile
1               5                   10                  15

Ser Gly Met Arg Met Glu Ile Gln Leu Cys Phe Ser Met Ala Glu Gly
            20                  25                  30

Leu Arg Ile Pro His Pro His Pro Thr Gly Arg Glu Ser Ser Asn His
        35                  40                  45

Pro Thr Trp Gly Ser Glu Asp Met Thr Leu Thr Gln Ser Arg Arg Ala
    50                  55                  60

Glu Ile Glu Thr Leu Pro Pro Val Leu Ser Pro Thr Lys Pro His Gln
65                  70                  75                  80

Ser Phe Ile Asn

<210> SEQ ID NO 263
<211> LENGTH: 49
<212> TYPE: PRT
<213> ORGANISM: Homo sapiens

<400> SEQUENCE: 263

Leu Val Asp Ala Asn Tyr Asp Pro His Pro Ser Gly Leu Cys Ser Pro
1               5                   10                  15

Phe Asn Leu Asp Glu His His Pro Arg Leu Phe Thr Gly Pro Pro Glu
            20                  25                  30

Ala Glu Phe Gly Tyr Ser Val Leu Gln His Val Gly Gly Gln Arg
        35                  40                  45

Trp

-continued

<210> SEQ ID NO 264
<211> LENGTH: 14
<212> TYPE: PRT
<213> ORGANISM: Homo sapiens

<400> SEQUENCE: 264

Glu Gly Lys Gln Arg Thr Val Gly Ser Gly Leu Cys Thr His
1               5                   10

<210> SEQ ID NO 265
<211> LENGTH: 9
<212> TYPE: PRT
<213> ORGANISM: Homo sapiens

<400> SEQUENCE: 265

Arg Gly Gly Pro Val Gln Ala Gly Leu
1               5

<210> SEQ ID NO 266
<211> LENGTH: 80
<212> TYPE: PRT
<213> ORGANISM: Homo sapiens

<400> SEQUENCE: 266

Lys Cys Leu Gly Leu His Asp Val Ser Cys Thr Leu Pro Leu Thr Ile
1               5                   10                  15

Leu Arg Thr Met Leu Thr Gly Ser Leu Tyr Pro Tyr Ser Pro Ser Arg
            20                  25                  30

Met Leu Val Gly Ala Pro Trp Asp Gly Pro Ser Gly Asp Arg Arg Gly
        35                  40                  45

Asp Val Tyr Arg Cys Ser Ile Gly Gly Phe His Ser Ala Pro Cys Thr
    50                  55                  60

Lys Gly His Leu Gly Lys Lys Pro Asp Leu Ser Pro Ala Asn Ser
65                  70                  75                  80

<210> SEQ ID NO 267
<211> LENGTH: 16
<212> TYPE: PRT
<213> ORGANISM: Homo sapiens

<400> SEQUENCE: 267

His Leu Val Thr Leu Thr Pro Trp Thr Leu Ser Ser Met Thr Leu Asn
1               5                   10                  15

<210> SEQ ID NO 268
<211> LENGTH: 7
<212> TYPE: PRT
<213> ORGANISM: Homo sapiens

<400> SEQUENCE: 268

Arg Ser Arg Thr Met Thr Pro
1               5

<210> SEQ ID NO 269
<211> LENGTH: 43
<212> TYPE: PRT
<213> ORGANISM: Homo sapiens

<400> SEQUENCE: 269

Leu His Ser Leu Leu Pro Phe Leu Gln Pro Gly Asp Tyr Gln Leu Gly
1               5                   10                  15

Asn Ser Ser Gln Pro Ala Val Asn Met His Leu Gly Met Ser Leu Leu
            20                  25                  30

Glu Thr Asp Ala Asp Gly Gly Phe Met Val Ser
            35                  40

<210> SEQ ID NO 270
<211> LENGTH: 71
<212> TYPE: PRT
<213> ORGANISM: Homo sapiens

<400> SEQUENCE: 270

Lys Lys Gly Leu Arg Arg Phe Thr Ala Gly Lys Arg Ala Leu Trp Tyr
1               5                   10                  15

Leu Gly Ser Gly Gly Leu Gly Leu Ser Ser Gln Cys Ser Gly Gly Arg
            20                  25                  30

Val Arg Pro Asp Leu Gln Ser Glu Leu Gln Asp Ser Gln Gly Tyr Ala
        35                  40                  45

Glu Lys Pro Cys Phe Glu Lys Pro Lys Thr Lys Thr Asn Gln Thr Thr
    50                  55                  60

Thr Thr Glu Lys Ala Pro Trp
65                  70

<210> SEQ ID NO 271
<211> LENGTH: 14
<212> TYPE: PRT
<213> ORGANISM: Homo sapiens

<400> SEQUENCE: 271

Gly Lys Leu Val Cys Ile Glu Glu Thr Arg Asn Ser Lys Pro
1               5                   10

<210> SEQ ID NO 272
<211> LENGTH: 16
<212> TYPE: PRT
<213> ORGANISM: Homo sapiens

<400> SEQUENCE: 272

Arg Ala Arg Gln Gly Ser Pro Trp Ser Gly Leu His Leu Ser Phe Asn
1               5                   10                  15

<210> SEQ ID NO 273
<211> LENGTH: 71
<212> TYPE: PRT
<213> ORGANISM: Homo sapiens

<400> SEQUENCE: 273

Val Cys Val Pro Arg Gly Pro Leu Lys Pro Gly Asp Asn Tyr Phe Ser
1               5                   10                  15

Tyr Pro Pro Arg Pro Val Pro Leu Phe Gly Leu Val Pro Ala Ala Ala
            20                  25                  30

Leu Ser Ser Val Leu Glu Tyr Val Pro Val Trp Met Leu His Ser Gly
        35                  40                  45

Pro Arg Glu Ala Trp His Pro Pro Asn Val Ser Gln Trp Lys Gly
    50                  55                  60

Pro Gly Ser Ser Val Pro Arg
65                  70

<210> SEQ ID NO 274
<211> LENGTH: 118
<212> TYPE: PRT
<213> ORGANISM: Homo sapiens

<400> SEQUENCE: 274

Gly Cys Trp Val Gly Lys Thr Arg Thr Lys Thr Trp Trp Arg Val Cys
1               5                   10                  15

Met Ala Ile Leu Ile Ile Pro Lys Cys Ala Cys Arg Arg Gly Ser Cys
                20                  25                  30

Leu Leu Thr Asp Asn Ser Asp Ser Leu Gly Glu Pro Gln Asp Thr Arg
            35                  40                  45

Ile Trp Phe Tyr Gln Leu Lys Asn Lys Thr Lys Gln His Ile Leu Cys
    50                  55                  60

Thr Ala Tyr Pro Ser Ser Ile Thr Cys Pro Pro Tyr Leu Ile Phe Val
65                  70                  75                  80

Gly Leu Ile Asp Ala Lys Ser Ala Leu Ser Tyr Trp Val Leu Pro Ser
                85                  90                  95

Cys Leu Ser Tyr Thr Phe Leu Ser Thr Ala Phe Trp Glu Ile Val Leu
                100                 105                 110

Cys Ser Pro Gly Cys Pro
            115

<210> SEQ ID NO 275
<211> LENGTH: 15
<212> TYPE: PRT
<213> ORGANISM: Homo sapiens

<400> SEQUENCE: 275

Ser Trp Asn Leu Leu Ala Ser Ala Ser Gln Ser Gln Val Leu Gly
1               5                   10                  15

<210> SEQ ID NO 276
<211> LENGTH: 17
<212> TYPE: PRT
<213> ORGANISM: Homo sapiens

<400> SEQUENCE: 276

Ala Cys Ile Val Cys Leu Ala Phe Ala Glu His Ala Leu Cys Gly His
1               5                   10                  15

Trp

<210> SEQ ID NO 277
<211> LENGTH: 101
<212> TYPE: PRT
<213> ORGANISM: Homo sapiens

<400> SEQUENCE: 277

Gly Met Ser Gln Ile Leu Pro Ser Pro Thr Thr His Thr Gln Thr Lys
1               5                   10                  15

Val Arg Leu Ser Lys Cys Ser Ile Ala Gln Gly Ser Gly Arg Pro Leu
                20                  25                  30

Ala Ser Ala Tyr Phe Ile Leu Leu Leu Cys Pro Ser Leu Leu Ser Leu
            35                  40                  45

Ile Ser Thr Leu Gly Thr Trp His Ser Thr Phe Leu Val Ile Lys Arg
    50                  55                  60

Glu Phe Pro Phe Lys Cys Leu His Cys Ser Val Leu Leu Gly His Ser
65                  70                  75                  80

Pro Leu Leu Thr Thr Pro His Ile Leu Pro Cys Phe Leu Phe Pro Ile
                85                  90                  95

Thr Met Pro Pro Phe
            100

<210> SEQ ID NO 278
<211> LENGTH: 31
<212> TYPE: PRT
<213> ORGANISM: Homo sapiens

<400> SEQUENCE: 278

Ala Val Pro His Thr Trp Met Ser Ser Leu Phe Trp Met Ala Pro Thr
1               5                   10                  15

Val Ser Ile Pro Gly Gln Lys Phe Arg Leu Ser Phe Gly Gly Trp
            20                  25                  30

<210> SEQ ID NO 279
<211> LENGTH: 11
<212> TYPE: PRT
<213> ORGANISM: Homo sapiens

<400> SEQUENCE: 279

Glu Asp Cys Ser Ser Ile Arg Ser Arg Tyr Arg
1               5                   10

<210> SEQ ID NO 280
<211> LENGTH: 12
<212> TYPE: PRT
<213> ORGANISM: Homo sapiens

<400> SEQUENCE: 280

Glu Lys Asp Met Trp Ile Gly Leu Glu Gly Lys Lys
1               5                   10

<210> SEQ ID NO 281
<211> LENGTH: 7
<212> TYPE: PRT
<213> ORGANISM: Homo sapiens

<400> SEQUENCE: 281

Thr Leu Leu Asp Pro Trp Met
1               5

<210> SEQ ID NO 282
<211> LENGTH: 25
<212> TYPE: PRT
<213> ORGANISM: Homo sapiens

<400> SEQUENCE: 282

Ala Ala Met Ser Ser Leu Leu Met Thr Pro Trp Asp Ile Val Phe Tyr
1               5                   10                  15

Arg Thr His Ala Gln Glu Leu Cys Asn
            20                  25

<210> SEQ ID NO 283
<211> LENGTH: 11
<212> TYPE: PRT
<213> ORGANISM: Homo sapiens

<400> SEQUENCE: 283

Leu Thr Lys Lys Ser Gln Lys Phe His Asn Val
1               5                   10

<210> SEQ ID NO 284
<211> LENGTH: 18
<212> TYPE: PRT
<213> ORGANISM: Homo sapiens

<400> SEQUENCE: 284

Ser Lys Phe Met Ile Val Trp Gly Ala Thr Leu Arg Ala Ser Leu Cys
1               5                   10                  15

Cys Leu

<210> SEQ ID NO 285
<211> LENGTH: 7
<212> TYPE: PRT
<213> ORGANISM: Homo sapiens

<400> SEQUENCE: 285

Leu Leu Gly Gln Cys Met Pro
1               5

<210> SEQ ID NO 286
<211> LENGTH: 58
<212> TYPE: PRT
<213> ORGANISM: Homo sapiens

<400> SEQUENCE: 286

Thr His Leu Phe Thr Ser Pro Ser Cys Cys Arg Leu Asp Thr Pro
1               5                   10                  15

Val Arg Gly Ser Leu Pro Leu His Pro Leu Cys Ser Ile Phe Ser Thr
            20                  25                  30

Leu Phe Ile His Pro Met Trp Ala His Gly Leu Leu Phe Ser Gly Arg
        35                  40                  45

Thr Gly Thr Val Arg Gly Glu Pro Cys Ala
    50                  55

<210> SEQ ID NO 287
<211> LENGTH: 45
<212> TYPE: PRT
<213> ORGANISM: Homo sapiens

<400> SEQUENCE: 287

Val Val Pro Gly Arg Leu Pro Asn Lys Gly Arg Ser Cys Glu Ser Ser
1               5                   10                  15

Lys Glu Pro Lys Ser Glu Gly Arg Ala Arg Asn Glu Asn Arg Pro Ser
            20                  25                  30

Asp His Gly Gly Met Val Arg His Cys Lys Gly Val Val
        35                  40                  45

<210> SEQ ID NO 288
<211> LENGTH: 38
<212> TYPE: PRT
<213> ORGANISM: Homo sapiens

<400> SEQUENCE: 288

Gly Arg Arg Lys Asp Gln Gln Gly Glu Gly Glu Gly Leu Glu Cys Ser
1               5                   10                  15

Val Tyr Ile Thr Arg Cys Ser Gly Arg Leu Ser Leu Ser Ala Cys Gln
            20                  25                  30

Lys Phe Val Glu Glu Gly
        35

<210> SEQ ID NO 289
<211> LENGTH: 42
<212> TYPE: PRT
<213> ORGANISM: Homo sapiens

```
<400> SEQUENCE: 289

Val Ala Val Thr Ile Leu Ser Leu Thr Val Phe Ala Phe Tyr Gly Val
1               5                   10                  15

Cys Gly Cys Ile Ser Pro Cys Leu Phe Cys Phe Cys Thr Gln Asn Ser
            20                  25                  30

Ile Phe Pro Leu Leu Leu Leu Arg Gln Phe
            35                  40

<210> SEQ ID NO 290
<211> LENGTH: 9
<212> TYPE: PRT
<213> ORGANISM: Homo sapiens

<400> SEQUENCE: 290

Tyr Leu Ala Ser Gln Pro Leu Thr Pro
1               5

<210> SEQ ID NO 291
<211> LENGTH: 5
<212> TYPE: PRT
<213> ORGANISM: Homo sapiens

<400> SEQUENCE: 291

Tyr Ser Phe Gln Thr
1               5

<210> SEQ ID NO 292
<211> LENGTH: 6
<212> TYPE: PRT
<213> ORGANISM: Homo sapiens

<400> SEQUENCE: 292

Thr Ser Gly Glu Ala Thr
1               5

<210> SEQ ID NO 293
<211> LENGTH: 9
<212> TYPE: PRT
<213> ORGANISM: Homo sapiens

<400> SEQUENCE: 293

Pro Asp Cys Leu Tyr Ser Pro Val Pro
1               5

<210> SEQ ID NO 294
<211> LENGTH: 14
<212> TYPE: PRT
<213> ORGANISM: Homo sapiens

<400> SEQUENCE: 294

Ser Cys Gln Pro Lys Cys Leu Leu Asn Glu Ser Ile Asn Lys
1               5                   10

<210> SEQ ID NO 295
<211> LENGTH: 47
<212> TYPE: PRT
<213> ORGANISM: Homo sapiens
```

-continued

<400> SEQUENCE: 295

Cys Leu Tyr Ile Phe Thr Leu Met Thr Asp Tyr Phe Ile Cys Ser Val
1               5                   10                  15

Pro Ser Lys Gln Ser Ser Cys Asp Ser Val Pro Val Cys Met Leu Asp
            20                  25                  30

Thr Val Gly Glu Trp Cys Arg Arg His Leu Thr Ser Val Asn Cys
        35                  40                  45

<210> SEQ ID NO 296
<211> LENGTH: 25
<212> TYPE: PRT
<213> ORGANISM: Homo sapiens

<400> SEQUENCE: 296

Tyr Thr Ile Arg Ala Cys Leu His Ala Ser Leu Cys Val Cys Ala Cys
1               5                   10                  15

Ile Cys Thr His Ile His Met Thr Ile
            20                  25

<210> SEQ ID NO 297
<211> LENGTH: 100
<212> TYPE: PRT
<213> ORGANISM: Homo sapiens

<400> SEQUENCE: 297

His Ser Phe Ile Ser Leu Leu Ser Thr Glu Gly Phe Ser Gln Ser Arg
1               5                   10                  15

Gly Gly Arg Pro Glu Ala Ala Arg Leu Leu Val Val Thr Asp Gly
            20                  25                  30

Glu Ser His Asp Gly Glu Glu Leu Pro Ala Ala Leu Lys Ala Cys Glu
        35                  40                  45

Ala Gly Arg Val Thr Arg Tyr Gly Ile Ala Val Arg Leu Asp Gln Val
    50                  55                  60

Gln Leu Phe Cys Phe Val Leu Tyr Arg Val Cys Val Cys Val Cys Val
65                  70                  75                  80

Cys Val Cys Val Cys Val Cys Val Ile Cys Val His Ala Ser
                85                  90                  95

Val His Ile Pro
            100

<210> SEQ ID NO 298
<211> LENGTH: 34
<212> TYPE: PRT
<213> ORGANISM: Homo sapiens

<400> SEQUENCE: 298

Cys Val Tyr Ala Gly Gln Arg Thr Thr Ser Asp Val Gly Pro His Leu
1               5                   10                  15

Pro Ser Cys Ser Lys Leu Asp Ile Leu Phe Thr Ser Ala Tyr Asn Lys
            20                  25                  30

Pro Asp

<210> SEQ ID NO 299
<211> LENGTH: 48
<212> TYPE: PRT
<213> ORGANISM: Homo sapiens

```
<400> SEQUENCE: 299

Leu Thr His Lys Ser Trp Ala Gly Leu Leu Ser Gln Pro Pro Val Ser
1               5                   10                  15

Trp Phe Glu Ala Phe Trp Asn Leu Gln Ile Ser Leu Ile Ser Asn Ser
                20                  25                  30

Cys Ser Pro Gly Asp Pro Leu Val Leu Glu Arg Pro Pro Arg Glu
            35                  40                  45
```